(12) United States Patent
Hale et al.

(10) Patent No.: US 7,125,887 B2
(45) Date of Patent: Oct. 24, 2006

(54) PYRROLIDINE MODULATORS OF CCR5 CHEMOKINE RECEPTOR ACTIVITY

(75) Inventors: Jeffrey J. Hale, Westfield, NJ (US); Charles G. Caldwell, Scotch Plains, NJ (US); Dooseop Kim, Westfield, NJ (US); Dong-Ming Shen, Edison, NJ (US); Sander G. Mills, Scotch Plains, NJ (US); Kevin T. Chapman, Scotch Plains, NJ (US); Liya Chen, East Brunswick, NJ (US); Malcolm MacCoss, Freehold, NJ (US); Amy Gentry, London (GB); Christopher L. Lynch, Scotch Plains, NJ (US); Christopher A. Willoughby, deceased, late of Newsbury Park, CA (US); by Yuan Cheng, legal representative, Newbury Park, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/399,084

(22) PCT Filed: Oct. 9, 2001

(86) PCT No.: PCT/US01/42562

§ 371 (c)(1),
(2), (4) Date: Jul. 17, 2003

(87) PCT Pub. No.: WO02/34716

PCT Pub. Date: May 2, 2002

(65) Prior Publication Data

US 2004/0087552 A1    May 6, 2004

(51) Int. Cl.
*A61K 31/44*    (2006.01)
*C07D 221/02*    (2006.01)

(52) U.S. Cl. ........... 514/300; 514/252.13; 514/253.01; 514/253.04; 514/253.09; 514/254.01; 514/254.04; 514/254.05; 514/319; 514/320; 514/321; 514/326; 514/333; 514/362; 514/364; 514/366; 514/372; 514/373; 514/374; 546/112; 546/193; 546/198; 546/200; 546/201; 546/208; 546/209; 546/256; 546/268.4; 546/276.4

(58) Field of Classification Search ................ 514/319, 514/320, 252.13, 253.04, 253.09, 253.01, 514/254.04, 254.05, 254.01, 299, 321, 326, 514/333, 362, 364, 366, 372, 373, 374, 300; 546/256, 268.4, 276.4, 193, 198, 200, 201, 546/208, 209, 112

See application file for complete search history.

(56) References Cited

U.S. PATENT DOCUMENTS

| | | | |
|---|---|---|---|
| 6,124,319 A | 9/2000 | MacCoss et al. | |
| 6,136,827 A | 10/2000 | Caldwell et al. | |
| 6,140,349 A | 10/2000 | Caldwell et al. | |
| 6,166,037 A | 12/2000 | Budhu et al. | |
| 6,248,755 B1 * | 6/2001 | Chapman et al. | 514/320 |
| 6,265,434 B1 | 7/2001 | Caldwell et al. | |
| 6,358,979 B1 | 3/2002 | Finke et al. | |
| 6,399,619 B1 | 6/2002 | Berk et al. | |
| 6,432,981 B1 | 8/2002 | Finke et al. | |
| 6,472,410 B1 | 10/2002 | Finke et al. | |
| 6,498,161 B1 | 12/2002 | Caldwell et al. | |
| 6,500,844 B1 | 12/2002 | Finke et al. | |
| 6,506,777 B1 | 1/2003 | Finke et al. | |
| 6,511,994 B1 | 1/2003 | Kim et al. | |
| 6,531,484 B1 | 3/2003 | Willoughby et al. | |
| 6,538,002 B1 | 3/2003 | Finke et al. | |
| 2002/0094989 A1 * | 7/2002 | Hale et al. | 514/253.04 |

OTHER PUBLICATIONS

Search result 1.*
Search result 2.*
T.J. Schall, "Biology of the Rantes/SIS Cytokine Family", Cytokine, vol. 3. No. 3, pp. 165-183 (1991).
P.M. Murphy et al., "The Molecular Biology of Leukocyte Chemoattractant Receptors", Annu. Rev. Immunol., vol. 12, pp. 593-655 (1994).

(Continued)

*Primary Examiner*—Celia Chang
(74) *Attorney, Agent, or Firm*—Kenneth R. Walton; Valerie J. Camara

(57) ABSTRACT

Pyrrolidine compounds of Formula (I), (wherein $R^1$, $R^2$, $R^3$, $R^4$, $R^5$, $R^{6a}$, $R^{6b}$, $R^7$ and $R^8$ are defined herein) are described. The compounds are modulators of CCR5 chemokine receptor activity. The compounds are useful, for example, in the prevention or treatment of infection by HIV and the treatment of AIDS, as compounds or pharmaceutically acceptable salts, or as ingredients in pharmaceutical compositions, optionally in combination with other antivirals, immunomodulators, antibiotics or vaccines. Methods of treating AIDS and methods of preventing or treating infection by HIV are also described

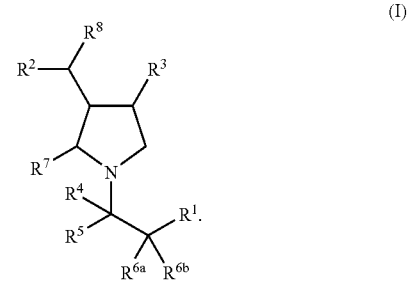

27 Claims, No Drawings

OTHER PUBLICATIONS

H. Deng et al., "Identification of a Major Co-Receptor for Primary Isolates of HIV-1", Nature, vol. 381, pp. 661-666 (1996).

R. Horuk, "Molecular Properties of the Chemokine Receptor Family", Trends, Pharm. Sci., vol. 15, pp. 159-165 (1994).

A Ben-Baruch et al., "Monocyte Chemotactic Protein-3 (MCP3) Interacts with Multiple Leukocyte Receptors", J. Biol. Chem., vol. 270, No. 38, pp. 22123-22128 (1995).

K. Neote et al., "Molecular Cloning, Functional Expression, and Signaling Characteristics of a C-C Chemokine Receptor", Cell, vol. 72, pp. 415-425 (1993).

C. Combadiere et al., "Cloning and Functional Expression of a Human Eosinophil CC Chemokine Receptor", J. Biol. Chem., vol. 270, pp. 16491-16494 (1995).

C.A. Power et al., "Molecular Cloning and Functional Expression of a Novel CC Chemokine Receptor cDNA from a Human Basophilic Cell Line", J. Biol. Chem., vol. 270, pp. 19495-19500 (1995).

M. Samson et al., "Molecular Cloning and Functional Expression of a New Human CC-Chemokine Receptor Gene", Biochemistry, vol. 35, pp. 3362-3367 (1996).

A. Chaudhuri et al., "Expression of the Duffy Antigen in K562 Cells", J. Biol. Chem, vol. 269, No. 11, pp. 7835-7838 (1994).

H. Kita et al., "Chemokines Active on Eosinophils: Potential Roles in Allergic Inflammation", J. Exp. Med, vol. 183, pp. 2421-2426 (1996).

D.H. Smith et al., "Blocking of HIV-1 Infectivity by a Soluble, Secreted Form of the CD4 Antigen", Science, vol. 238, pp. 1704-1707 (1987).

T. Dragic et al., "HIV-1 entry into CD4 Cells is Mediated by the Chemokine Receptor CC-CKR-5", Nature, vol. 381, pp. 667-668 (1996).

L. Wu, "CD4-Induced Interaction of Primary HIV-1 GP120 Glycoproteins with the Chemokine Receoptor CCR-5", Nature, vol. 384, pp. 179-183 (1996).

A. Trkola et al . . . , "CD4-Dependent, Antibody-Sensitive Interactions Between HIV-1 and its co-receptor CCR-5,", Nature, vol. 384, pp. 184-187 (1996).

M. Samson et al., "Resistance to HIV-1 Infection in Caucasian Individuals Bearing Mutant Alleles of the CCR-5 Chemokine Receptor Gene", Nature, vol. 382, pp. 722-725 (1996).

L. Zhang et al., "HIV-1 Subtype and Second-Receptor Use", Nature, vol. 383, pp. 768 (1996).

Y. Huang et al., "The Role of a Mutuant CCR5 Allele in HIV-1 Transmission and Disease Progression", Nature Medicine, vol. 2, pp. 1240-1241 (1996).

J.A. Levy, "Infection by Human Immunodeficiency Virus, CD4 is Not Enough", The New England Journal of Medicine, vol. 335, pp. 1528-1530 (1996).

* cited by examiner

PYRROLIDINE MODULATORS OF CCR5 CHEMOKINE RECEPTOR ACTIVITY

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C—X—C ($\alpha$) and C—C ($\beta$), depending on whether the first two cysteines are separated by a single amino acid (C—X—C) or are adjacent (C—C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least sixteen human chemokine receptors that bind or respond to $\beta$-chemokines with the following characteristic pattern: CCR1 (or "CKR-1" or "CC-CKR-1") [MIP-1$\alpha$, MIP-1$\beta$, MCP-3, RANTES] (Ben-Barruch, et al., *J. Biol. Chem.*, 270, 22123–22128 (1995); Beote, et al, *Cell*, 72, 415–425 (1993)); CCR2A and CCR2B (or "CKR-2A"/ "CKR-2A" or "CC-CKR-2A"/"CC-CKR-2A") [MCP-1, MCP-3, MCP-4]; CCR3 (or "CKR-3" or "CC-CKR-3") [eotaxin, RANTES, MCP-3] (Combadiere, et al., *J. Biol. Chem.*, 270, 16491–16494 (1995); CCR4 (or "CKR-4" or "CC-CKR-4") [MIP-1$\alpha$, RANTES, MCP-1] (Power, et al., *J. Biol. Chem.*, 270, 19495–19500 (1995)); CCR5 (or "CKR-5" or "CC-CKR-5") [MIP-1$\alpha$, RANTES, MIP-1$\beta$] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR1, CCR2, CCR2A, CCR2B, CCR3, CCR4, CCR5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., *J. Exp. Med.* 183, 2421–2426 (1996). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require a chemokine receptors, most probably CCR5 or CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that $\beta$-chemokine ligands prevent HIV-1 from fusing with the cell (Dragic, et al., *Nature*, 381, 667–673 (1996)). It has further been demonstrated that a complex of gp120 and soluble CD4 interacts specifically with CCR5 and inhibits the binding of the natural CCR5 ligands MIP-1$\alpha$ and MIP-1$\beta$ (Wu, et al., *Nature*, 384, 179–183 (1996); Trkola, et al., *Nature*, 384, 184–187 (1996)).

Humans who are homozygous for mutant CCR5 receptors which are not expressed on the cell surface appear to be unusually resistant to HIV-1 infection and are not immunocompromised by the presence of this genetic variant (*Nature*, 382, 722–725 (1996)). Absence of CCR5 appears to confer substantial protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR5 or fusin, some can use both as well as the related CCR2B and CCR3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β.

SUMMARY OF THE INVENTION

The present invention is directed to compounds which inhibit the entry of human immunodeficiency virus (HIV) into target cells and are of value in the prevention of infection by HIV, the treatment of infection by HIV, the prevention and/or treatment of the resulting acquired immune deficiency syndrome (AIDS), and the delay in the onset of AIDS. The present invention also relates to pharmaceutical compositions containing the compounds and to a method of use of the present compounds and other agents for the prevention and treatment of AIDS and viral infection by HIV.

The present invention is further directed to compounds which are modulators of CCR5 chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention includes compounds of Formula I:

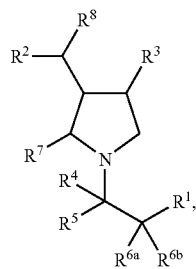

(I)

wherein:

$R^1$ is:
(1) —$CO_2H$,
(2) —$NO_2$,
(3) -tetrazolyl,
(4) -hydroxyisoxazole,
(5) —$SO_2NHCO$—($C_{0-3}$ alkyl)—$R^a$, or
(6) —$P(O)(OH)(OR^a)$;
wherein $R^a$ is independently selected from hydrogen, $C_{1-6}$ alkyl, $C_{5-6}$ cycloalkyl, benzyl and phenyl, where any one of which except hydrogen is optionally substituted with 1–3 substituents where the substituents are independently selected from halo, $C_{1-3}$ alkyl, —O—$C_{1-3}$ alkyl, and —$CF_3$, $R^2$ is:

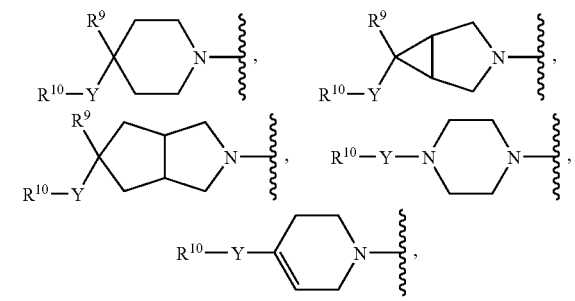

wherein "⁓⁓⁓" denotes the point of attachment;
$R^9$ is selected from:
(1) hydrogen,
(2) $C_{1-6}$ alkyl, which is unsubstituted or substituted with 1–4 substituents where the substituents are independently selected from hydroxy, cyano, and halo,
(3) cyano,
(4) hydroxy, and
(5) halo; and
Y is:
(1) a direct single bond;
(2) —$C_{1-10}$ alkyl- or —($C_{0-6}$ alkyl)$C_{3-6}$cycloalkyl($C_{0-6}$ alkyl)-, either of which is optionally substituted with 1–7 substituents independently selected from:
(a) halo,
(b) hydroxy,
(c) —O—$C_{1-3}$ alkyl,
(d) —$CF_3$,
(e) —($C_{1-3}$ alkyl)hydroxy, and
(f) ethylenedioxy;
(3) —($C_{0-6}$ alkyl)-$Z^1$-($C_{0-6}$ alkyl)-, wherein each alkyl is optionally substituted with 1–7 substituents independently selected from:
(a) halo,
(b) hydroxy,
(c) —O—$C_{1-3}$ alkyl, and
(d) —$CF_3$;
and where $Z^1$ is selected from —$SO_2$—, —$N(R^u)$—, —$N(R^u)C(=CHR^s)N(R^u)$—, —$N(R^u)C(=NR^s)N(R^u)$—, —S—, —O—, —SO—, —$SO_2N(R^u)$—, —$N(R^u)SO_2$—, and —$PO_2$—;
$R_u$ is hydrogen, $C_{1-6}$ alkyl, $C_{2-6}$ alkenyl, benzyl, phenyl, (CO)$C_{1-6}$ alkyl, —$SO_2$—$C_{1-6}$ alkyl, —$SO_2$-phenyl, —$SO_2$-heterocycle, or $C_{1-6}$ alkyl-$C_{3-6}$ cycloalkyl; wherein any of which except hydrogen is optionally substituted with 1–3 substituents independently selected from halo, $C_{1-3}$ alkyl, —O—$C_{1-3}$ alkyl, and —$CF_3$;
$R^s$ is hydrogen, $C_{1-4}$ alkyl, —$NO_2$ or —CN;
(4) —($C_{0-6}$ alkyl)-$Z^2$-($C_{0-6}$ alkyl)-, wherein each alkyl is optionally substituted with 1–7 substituents independently selected from:
(a) halo,
(b) hydroxy,
(c) —O—$C_{1-3}$ alkyl, and
(d) —$CF_3$;
and where:
$Z^2$ is selected from —C(=O)—, —C(=O)O—, —OC(=O)—, —C(=O)$NR^v$—, —$NR^vC(=O)$—, —OC(=O)$NR^v$—, —$NR^vC(=O)O$—, and —$NR^wC(=O)NR^v$—;

R$^v$ is hydrogen, C$_{1-6}$ alkyl, C$_{2-6}$ alkenyl, C$_{2-6}$ alkynyl, benzyl, phenyl, or C$_{1-6}$ alkyl-C$_{3-6}$ cycloalkyl; wherein any of which except hydrogen is optionally substituted with 1–3 substituents independently selected from halo, C$_{1-3}$ alkyl, —O—C$_{1-3}$ alkyl, and —CF$_3$; and R$^w$ is hydrogen or C$_{1-6}$ alkyl;

R$^{10}$ is:

(1) a heterocycle selected from pyrazolyl and imidazolyl, wherein the pyrazolyl or imidazolyl is substituted with three of R$^d$, wherein each R$^d$ is independently selected from the group consisting of:
  (a) halo,
  (b) cyano,
  (c) hydroxy,
  (d) C$_{1-6}$ alkyl, which is unsubstituted or substituted with 1–5 of R$^e$ where R$^e$ is independently selected from halo, cyano, hydroxy, —O—C$_{1-6}$ alkyl, —C$_{3-6}$ cycloalkyl, —CO$_2$H, —CO$_2$—(C$_{1-6}$ alkyl), —CF$_3$, —SO$_2$R$^a$, —NR$^a$R$^b$ (where R$^a$ is independently as defined above and R$^b$ is independently selected from the definitions of R$^a$), phenyl, naphthyl, biphenyl, and heterocycle;
    wherein phenyl, naphthyl, biphenyl, or heterocycle is unsubstituted or substituted with 1–7 of R$^f$ where R$^f$ is independently selected from halo, cyano, hydroxy, C$_{1-6}$ alkyl, C$_{1-6}$ haloalkyl, —O—C$_{1-6}$ alkyl, —O—C$_{1-6}$ haloalkyl, —CO$_2$H, —CO$_2$(C$_{1-6}$ alkyl), —NR$^a$R$^b$, —(C$_{1-6}$ alkyl)—NR$^a$R$^b$, —SO$_2$R$^a$, —N(R$^a$)SO$_2$R$^b$, —N(R$^a$)COR$^b$, —(C$_{1-6}$ alkyl)hydroxy, —O—C$_{3-6}$ cycloalkyl, benzyloxy, phenoxy, and —NO$_2$,
  (e) —O—C$_{1-6}$ alkyl, which is unsubstituted or substituted with 1–5 of R$^e$,
  (f) —O-phenyl, which is unsubstituted or substituted with 1–5 of R$^f$,
  (g) —O-heterocycle, which is unsubstituted or substituted with 1–5 of R$^f$,
  (h) —NO$_2$,
  (i) phenyl,
  (j) —CO$_2$R$^a$,
  (k) tetrazolyl,
  (l) —NR$^a$R$^b$,
  (m) —NR$^a$—COR$^b$,
  (n) —NR$^a$—CO$_2$R$^b$,
  (o) —CO—NR$^a$R$^b$,
  (p) —OCO—NR$^a$R$^b$,
  (q) —NR$^a$CO—NR$^a$R$^b$,
  (r) —S(O)$_m$—R$^a$, wherein m is an integer selected from 0, 1, and 2,
  (s) —S(O)$_2$—NR$^a$R$^b$,
  (t) —NR$^a$S(O)$_2$—R$^b$,
  (u) —NR$^a$S(O)$_2$—NR$^a$R$^b$,
  (v) C$_{2-6}$ alkenyl,
  (w) furanyl, which is unsubstituted or substituted with benzyl which is unsubstituted or substituted with 1–7 of R$_f$ wherein R$_f$ is independently as defined above,
  (x) —C$_{3-6}$ cycloalkyl, and
  (y) —O—C$_{3-6}$ cycloalkyl; or (2) a heterocycle selected from:

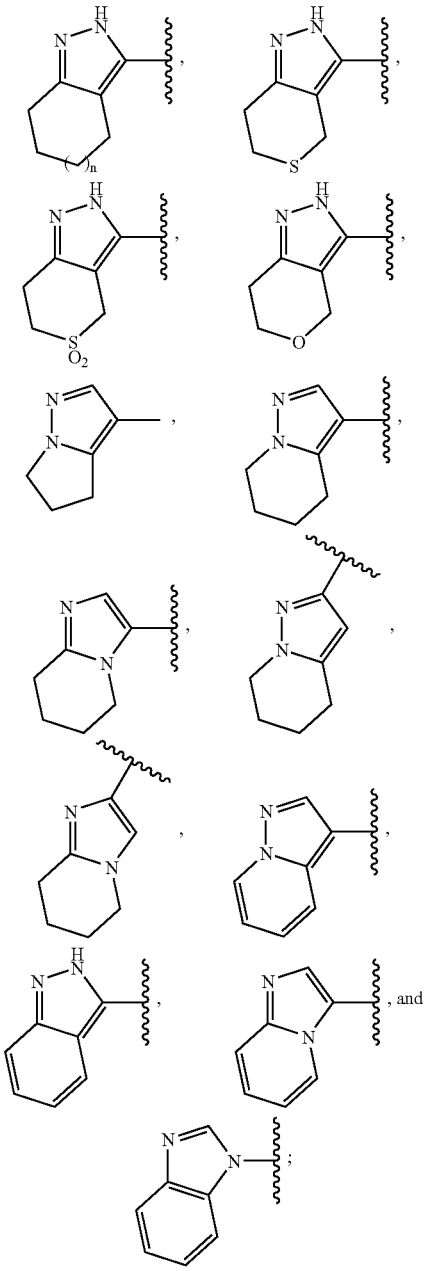

wherein n is an integer equal to zero or 1, and
the heterocycle is mono-substituted in the pyrazolyl or imidazolyl ring with any one of R$^d$ as defined above, and is either unsubstituted in the other ring or is substituted with 1 or more substituents where each substituent is independently selected from (a) to (y) of R$^d$ as defined above;

R$^3$ is phenyl, naphthyl, or heterocycle, any one of which is unsubstituted or substituted with 1–7 substituents where the substituents are independently selected from:
  (a) halo,
  (b) C$_{1-4}$ alkyl,
  (c) C$_{1-4}$ haloalkyl,
  (d) hydroxy, (e) —O—$C_{1-4}$ alkyl,
(f) —O—$C_{1-4}$ haloalkyl,
(g) —$CO_2R^a$,
(h) —$NR^aR^b$, and
(i) —$CONR^aR^b$;

$R^4$ is hydrogen, $C_{1-10}$ alkyl, $C_{3-8}$ cycloalkyl, —($C_{1-3}$ alkyl)—$C_{3-8}$ cycloalkyl, —($C_{0-2}$ alkyl)—($C_{3-8}$ cycloalkylidenyl)—($C_{1-2}$ alkyl), $C_{2-10}$ alkenyl, $C_{2-10}$ alkynyl, cyclohexenyl, phenyl, —($C_{1-6}$ alkyl)-phenyl, naphthyl, dihydronaphthyl, tetrahydronaphthyl, octahydronaphthyl, biphenyl, or heterocycle; wherein any one of which except for hydrogen is unsubstituted or substituted with 1–7 of $R^d$ where $R^d$ is independently as defined above;

$R^5$ is hydrogen or $C_{1-6}$ alkyl, wherein the alkyl is unsubstituted or substituted with 1–7 substituents where the substituents are independently selected from:
(a) halo,
(b) —$CF_3$,
(c) hydroxy,
(d) $C_{1-3}$ alkyl,
(e) —O—$C_{1-13}$ alkyl,
(f) —$CO_2R^a$,
(g) —$NR^aR^b$, and
(h) —$CONR^aR^b$;

or alternatively $R^4$ and $R^5$ together with the carbon atom to which they are attached form a $C_{3-8}$ cycloalkyl ring which may be unsubstituted or substituted with 1–7 of $R^d$;

$R^{6a}$ and $R^{6b}$ are each independently $C_{1-6}$ alkyl, $C_{2-6}$ alkenyl, $C_{2-6}$ alkynyl, $C_{3-8}$ cycloalkyl, phenyl, naphthyl, or heterocycle; wherein any one of which is unsubstituted or substituted with 1–7 substituents where the substituents are independently selected from:
(a) halo,
(b) $C_{1-4}$ haloalkyl,
(c) hydroxy,
(d) $C_{1-4}$ alkyl,
(e) —O—$C_{1-4}$ alkyl,
(f) —O—$C_{1-4}$ haloalkyl,
(g) $C_{3-8}$ cycloalkyl,
(h) —$CO_2R^a$,
(i) —$NR^aR^b$, and
(j) —$CONR^aR^b$;

or alternatively $R^{6a}$ and $R^{6b}$ together with the carbon atom to which they are attached form:
(a) a 3- to 8-membered saturated carbocyclic ring, in which one of the ling carbons is optionally a member of a 3- to 8-membered spiro ring containing carbon atoms and optionally 1 or 2 heteroatoms independently selected from nitrogen, oxygen and sulfur;
(b) a 4- to 8-membered monocyclic heterocycle containing from 1 to 3 heteroatoms independently selected from nitrogen, oxygen and sulfur, in which one of the ring carbons is optionally a member of a 3- to 8-membered spiro ring containing carbon atoms and optionally 1 or 2 heteroatoms independently selected from nitrogen, oxygen and sulfur;
(c) a 5- to 8-membered saturated carbocyclic ring to which is fused a $C_{3-8}$ cycloalkyl, or
(d) a 5- to 8-membered heterocyclic ring containing from 1 to 3 heteroatoms selected from nitrogen, oxygen and sulfur, to which is fused a $C_{3-8}$ cycloalkyl,
wherein the ring system of (a), (b), (c) or (d) is optionally substituted with from 1 to 3 substituents selected from halo, $C_{1-4}$ alkyl, $C_{1-4}$ haloalkyl, —O—$C_{1-4}$ alkyl, —O—$C_{1-14}$ haloalkyl, and hydroxy;

$R^7$ is hydrogen or $C_{1-6}$ alkyl; and
$R^8$ is hydrogen or $C_{1-6}$ alkyl;

or a pharmaceutically acceptable salt thereof.

An aspect of the present invention is a compound of Formula I as just defined, except that the choice of heterocycles in part (2) of the definition of $R^{10}$ does not include

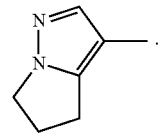

A first embodiment of the present invention is a compound of Formula I, wherein $R^1$ is:
(1) —$CO_2H$,
(2) —$P(O)(OH)_2$, or
(3) -tetrazolyl;

and all other variables are as originally defined;

or a pharmaceutically acceptable salt thereof.

In one aspect of the first embodiment, $R^1$ is:
(1) —$CO_2H$, or
(2) -tetrazolyl.

In another aspect of the first embodiment, $R^1$ is —$CO_2H$.

A second embodiment of the present invention is a compound of Formula I, $R^2$ is:

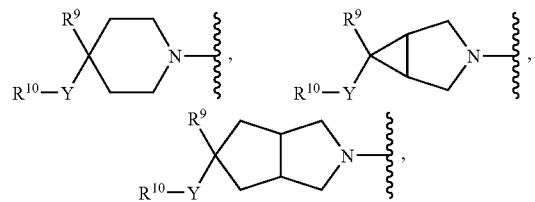

and all other variables are as originally defined;

or a pharmaceutically acceptable salt thereof.

In an aspect of the second embodiment, $R^2$ is:

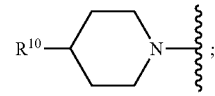

A third embodiment of the present invention is a compound of Formula I, wherein $R^3$ is phenyl, thienyl, pyrazolyl, thiazolyl, thiadiazolyl, furanyl, oxadiazolyl, pyrazinyl, pyrimidinyl, or pyridyl, any one of which is unsubstituted or substituted with 1–5 substituents where the substituents are independently selected from:
(a) halo,
(b) —$CF_3$,
(c) hydroxy,
(d) $C_{1-3}$ alkyl, and
(e) —O—$C_{1-3}$ alkyl;

and all other variables are as originally defined;

or a pharmaceutically acceptable salt thereof.

In an aspect of the third embodiment, $R^3$ is phenyl or thienyl, either of which is unsubstituted or substituted with 1–5 substituents where the substituents are independently selected from:

(a) halo,
(b) —$CF_3$,
(c) hydroxy, and
(d) $C_{1-3}$ alkyl.

In another aspect of the third embodiment, $R^3$ is phenyl or thienyl, wherein the phenyl is optionally substituted with 1–5 substituents independently selected from fluoro and chloro.

In still another aspect of the third embodiment, $R^3$ is unsubstituted phenyl, 3-fluorophenyl, or 3-thienyl.

A fourth embodiment of the present invention is a compound of Formula I, wherein $R^4$ and $R^5$ are both hydrogen;

and all other variables are as originally defined;

or a pharmaceutically acceptable salt thereof.

A fifth embodiment of the present invention is a compound of Formula I, wherein $R^{6a}$ and $R^{6b}$ are each independently $C_{1-6}$ alkyl or $C_{3-6}$ cycloalkyl, either of which is unsubstituted or substituted with 1–7 substituents independently selected from:
(a) halo,
(b) —$CF_3$,
(c) hydroxy, and
(d) —O—$C_{1-3}$ alkyl;

or $R^{6a}$ and $R^{6b}$ together with the carbon atom to which they are attached form:
(a) a 3- to 6-membered saturated carbocyclic ring,
(b) a 4- to 6-membered saturated heterocyclic ring containing one oxygen atom, or
(c) a 5- or 6-membered saturated carbocyclic ring to which is fused a $C_{3-6}$ cycloalkyl;

wherein the ring system of (a), (b), or (c) is optionally substituted with from 1 to 3 substituents selected from halo, $C_{1-4}$ alkyl, $C_{1-4}$ haloalkyl, —O—$C_{1-4}$ alkyl, —O—$C_{1-4}$ haloalkyl, or hydroxy;

and all other variables are as originally defined;

or a pharmaceutically acceptable salt thereof.

In one aspect of the fifth embodiment, $R^{6a}$ and $R^{6b}$ are each $C_{1-3}$ alkyl;

or one of $R^{6a}$ and $R^{6b}$ is $C_{1-3}$ alkyl, and the other of $R^{6a}$ and $R^{6b}$ is $C_{3-6}$ cycloalkyl;

or $R^{6a}$ and $R^{6b}$ together with the carbon atom to which they are attached form cyclpropylidenyl, cyclobutylidenyl, cyclopentylidenyl, cyclohexylidenyl, bicyclo[3.1.0]cyclohexylidenyl, tetrahydropyranylidenyl, or tetrahydrofuranylidenyl.

In another aspect of the fifth embodiment, $R^{6a}$ and $R^{6b}$ are just as defined in the preceding aspect, except that cyclopropylidenyl is not included among the choice of rings formed by $R^{6a}$ and $R^{6b}$ together with the carbon atom to which they are attached.

A sixth embodiment of the present invention is a compound of Formula I, wherein $R^7$ is hydrogen;

and all other variables are as originally defined;

or a pharmaceutically acceptable salt thereof.

A seventh embodiment of the present invention is a compound of Formula I, wherein $R^8$ is hydrogen;

and all other variables are as originally defined;

or a pharmaceutically acceptable salt thereof.

An eighth embodiment of the present invention is a compound of Formula I, wherein $R^8$ is methyl;

and all other variables are as originally defined;

or a pharmaceutically acceptable salt thereof.

A ninth embodiment of the present invention is a compound of Formula I, wherein $R^9$ is hydrogen, fluoro, hydroxy or $C_{1-6}$ alkyl;

and all other variables are as originally defined;

or a pharmaceutically acceptable salt thereof.

In an aspect of the ninth embodiment, $R^9$ is hydrogen or fluoro. In another aspect of the ninth embodiment, $R^9$ is hydrogen.

A tenth embodiment of the present invention is a compound of Formula I, wherein Y is a direct single bond;

and all other variables are as originally defined;

or a pharmaceutically acceptable salt thereof.

An eleventh embodiment of the present invention is a compound of Formula I, wherein $R^{10}$ is:
(1) a heterocycle selected from pyrazolyl and imidazolyl, wherein the pyrazolyl or imidazolyl is substituted with three substituents independently selected from the group consisting of:
(a) halo,
(b) cyano,
(c) hydroxy,
(d) $C_{1-6}$ alkyl, which is unsubstituted or substituted with 1–5 of $R^e$ where $R^e$ is independently selected from halo, cyano, hydroxy, —O—$C_{1-16}$ alkyl, —$C_{3-5}$ cycloalkyl, —$CO_2H$, —$CO_2(C_{1-6}$ alkyl), —$CF_3$, —$SO_2R^a$, —$NR^aR^b$,
where $R^a$ and $R^b$ are independently selected from hydrogen, $C_{1-6}$ alkyl, $C_{5-6}$ cycloalkyl, benzyl or phenyl, which is unsubstituted or substituted with 1–3 substituents where the substituents are independently selected from halo, $C_{1-3}$ alkyl, —O—$C_{1-3}$ alkyl, $C_{1-3}$ fluoroalkyl, and —O—$C_{1-3}$ fluoroalkyl,
phenyl, naphthyl, biphenyl, and heterocycle, wherein the phenyl, naphthyl, biphenyl or heterocycle is unsubstituted or substituted with 1–7 of $R^f$ where $R^f$ is independently selected from halo, cyano, hydroxy, $C_{1-4}$ alkyl, —O—$C_{1-4}$ alkyl, —O—$C_{3-5}$ cycloalkyl, —$CO_2H$, —$CO_2(C_{1-6}$ alkyl), —$CF_3$, —$OCF_3$, —$SO_2R^a$, —$N(R^a)SO_2R^b$ and —$NR^aR^b$,
(e) —O—$C_{1-6}$ alkyl, which is unsubstituted or substituted with 1–5 of $R^e$,
(f) —$NO_2$,
(g) phenyl,
(h) —$CO_2R^a$,
(i) tetrazolyl,
(j) —$NR^aR^b$,
(k) —$NR^a$—$COR^b$,
(l) —$NR^a$—$CO_2R^b$,
(m) —CO—$NR^aR^b$,
(n) —OCO—$NR^aR^b$,
(o) —$NR^aCO$—$NR^aR^b$,
(p) —$S(O)_m$—$R^a$, wherein m is an integer selected from 0, 1, and 2,
(q) —$S(O)_2$—$NR^aR^b$,
(r) —$NR^aS(O)_2$—$R^b$,
(s) —$NR^aS(O)_2$—$NR^aR^b$,
(t) —$C_{2-3}$ alkenyl,
(u) —$C_{3-6}$ cycloalkyl, and
(v) —O—$C_{3-6}$ cycloalkyl; or (2) a heterocycle selected from:

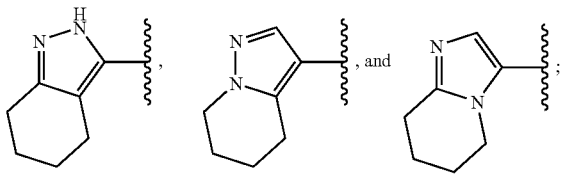

wherein the heterocycle is mono-substituted in the pyrazolyl or imidazolyl ring with any one of $R^d$ as defined above, and is either unsubstituted in the other ring or substituted with 1 to 3 substituents independently selected from:
(a) halo,
(b) $C_{1-4}$ alkyl,
(c) $C_{1-4}$ haloalkyl,
(d) —OH,
(e) —O—$C_{1-14}$ alkyl,
(f) —O—$C_{1-4}$ haloalkyl, and
(g) —CN;

and all other variables are as originally defined;

or a pharmaceutically acceptable salt thereof.

In an aspect of the eleventh embodiment, $R^{10}$ is:
(1) a heterocycle selected from pyrazolyl and imidazolyl, wherein the pyrazolyl or imidazolyl is substituted with three substituents independently selected from the group consisting of:
(a) halo,
(b) cyano,
(c) —$NO_2$,
(d) —$CF_3$,
(e) —$CHF_2$,
(f) —$CH_2F$,
(g) —$CH_2OH$,
(h) —$CH_2OCH_3$,
(i) —$(CH_2)_{1-2}SO_2$—($C_{1-2}$ alkyl)
(j) phenyl,
(k) $C_{1-6}$ alkyl, which is unsubstituted or substituted with phenyl,
which is unsubstituted or substituted with 1–4 of $R^f$ where $R^f$ is independently selected from halo, cyano, hydroxy, —$C_{1-4}$ alkyl, —O—$C_{1-4}$ alkyl, —O—$C_{3-5}$ cycloalkyl, —$CO_2H$, —$CO_2(C_{1-6}$ alkyl), —$CF_3$, —$OCF_3$, —$SO_2$—($C_{1-3}$ alkyl), and —N($R_a$)$SO_2$—($C_{1-13}$ alkyl),
(l) —O—$C_{1-6}$ alkyl,
(m) —$C_{3-5}$ cycloalkyl,
(n) —$CH_2$—($C_{3-5}$ cycloalkyl), and
(o) —O—$C_{3-5}$ cycloalkyl; or
(2) a heterocycle selected from:

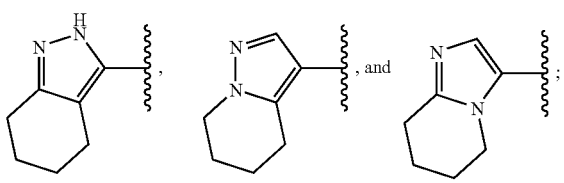

wherein the heterocycle is mono-substituted in the pyrazolyl or imidazolyl ring with any one of $R^d$ as defined above, and is either unsubstituted in the other ring or substituted with 1 to 3 substituents independently selected from:
(a) halo,
(b) $C_{1-4}$ alkyl,
(c) —$CF_3$,
(d) —OH,
(e) —O—$C_{1-4}$ alkyl,
(f) —$OCF_3$, and
(g) —CN.

In another aspect of the eleventh embodiment, $R^{10}$ is:
(1) pyrazolyl substituted with three substituents independently selected from the group consisting of:
(a) fluoro,
(b) chloro,
(c) $C_{1-6}$ alkyl,
(d) —$CH_2$-phenyl, wherein the phenyl is unsubstituted or substituted with 1 or 2 substituents independently selected from chloro, fluoro, —CN, —$C_{1-3}$ alkyl, —O—$C_{1-3}$ alkyl, —O-cyclopropyl, —O-cyclobutyl, —$CF_3$, —$OCF_3$, —$SO_2$—($C_{1-3}$ alkyl), and —N(H)$SO_2$—($C_{1-3}$ alkyl),
(e) —$CH_2CH_2$-phenyl, and
(f) phenyl; or
(2) a heterocycle selected from:

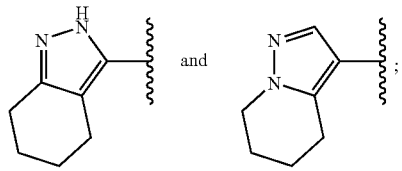

wherein the heterocycle is mono-substituted in the pyrazolyl ring with any one of $R^d$ as defined above, and is either unsubstituted in the other ring or substituted with 1 to 3 substituents independently selected from:
(a) fluoro,
(b) chloro,
(b) $C_{1-4}$ alkyl,
(c) —$CF_3$,
(d) —OH,
(e) —O—$C_{1-4}$ alkyl,
(f) —$OCF_3$, and
(g) —CN.

In still another aspect of the eleventh embodiment, $R^{10}$ is as defined in the eleventh embodiment, except that (t) —$C_{2-3}$ alkenyl is not included as a possible substituent(s) on the heterocycle (1) selected from pyrazolyl and imidazolyl.

It is to be understood that additional embodiments of the present invention include, but are not limited to, compounds of Formula I wherein each of two or three or more of $R^1$, $R^2$, $R^3$, $R^4$, $R^5$, $R^{6a}$, $R^{6b}$, $R^7$, $R^8$, $R^9$, $R^{10}$ and Y is independently defined in accordance with one of the foregoing embodiments or aspects thereof as set forth above. Any and all possible combinations of these variables in Formula I are within the scope of the present invention.

The compounds of the instant invention have at least two asymmetric centers at the ring junction of the substituents bearing $R^2$ and $R^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention.

A first class of compounds of the present invention are compounds having the trans orientation, depicted as:

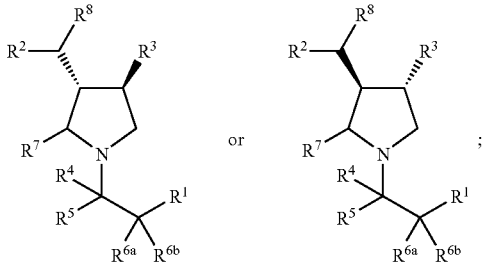

and pharmaceutically acceptable salts thereof.

A second class of the present invention is compounds of Formula (II):

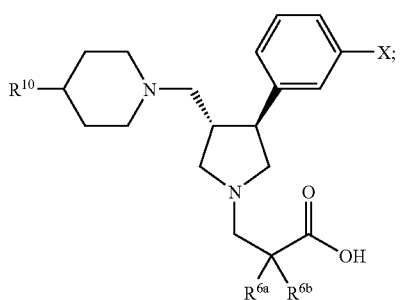

wherein $R^{6a}$ and $R^{6b}$ are each $C_{1-3}$ alkyl;

or one of $R^{6a}$ and $R^{6b}$ is $C_{1-3}$ alkyl, and the other of $R^{6a}$ and $R^{6b}$ is $C_{3-6}$ cycloalkyl;

or $R^{6a}$ and $R^{6b}$ together with the carbon atom to which they are attached form:

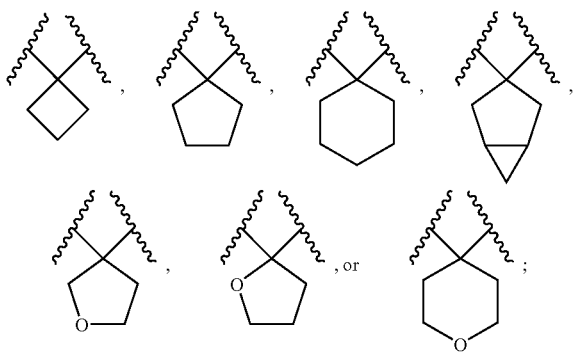

$R^{10}$ is:

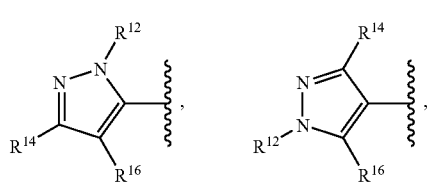

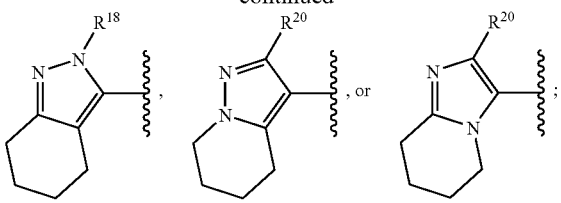

$R^{12}$ is $C_{1-3}$ alkyl, $C_{1-3}$ fluoroalkyl, or —$CH_2$-phenyl wherein the phenyl is optionally substituted with 1 or 2 substituents independently selected from chloro, fluoro, —CN, —$C_{1-3}$ alkyl, —O—$C_{1-3}$ alkyl, —O-cyclopropyl, —O-cyclobutyl, —$CF_3$, —$OCF_3$, —$SO_2$—($C_{1-3}$ alkyl), and —$NHSO_2$—($C_{1-3}$ alkyl);

each of $R^{14}$ and $R^{16}$ is independently —$C_{1-3}$ alkyl, $C_{1-3}$ fluoroalkyl, —O—$C_{1-3}$ alkyl, —O—$C_{1-3}$ fluoroalkyl, cyclopropyl, cyclobutyl, or —$CH_2$-phenyl wherein the phenyl is optionally substituted with 1 or 2 substituents independently selected from chloro, fluoro, —CN, —$C_{1-3}$ alkyl, —O—$C_{1-3}$ alkyl, —O-cyclopropyl, —O-cyclobutyl, —$CF_3$, —$OCF_3$, and —$SO_2$—($C_{1-3}$ alkyl);

$R^{18}$ is $C_{1-3}$ alkyl;

$R^{20}$ is —$C_{1-3}$ alkyl; and

X is hydrogen or fluoro;

or a pharmaceutically acceptable salt thereof.

A first sub-class of the present invention is a compound of Formula II, wherein $R^{10}$ is:

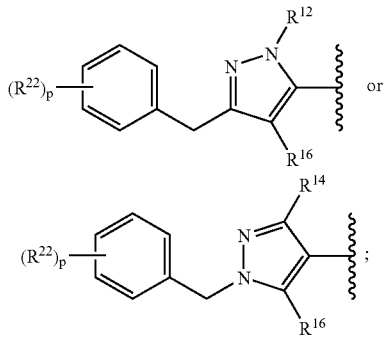

$R^{12}$ is methyl or ethyl;
$R^{14}$ is methyl or ethyl;
$R^{16}$ is halo, methyl, or ethyl;
each $R^{22}$ is independently chloro, fluoro, —CN, —$C_{1-3}$ alkyl, —O—$C_{1-3}$ alkyl, —O-cyclopropyl, —O-cyclobutyl, —$CF_3$, —$OCF_3$, or —$SO_2$—($C_{1-3}$ alkyl); and
p is an integer from zero to 3;

and all other variables are as defined for the second class;

or a pharmaceutically acceptable salt thereof.

A second sub-class of the present invention is a compound of Formula II, wherein $R^{10}$ is:

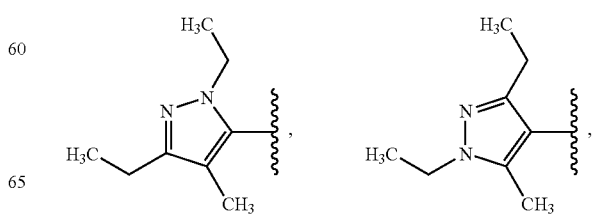

-continued

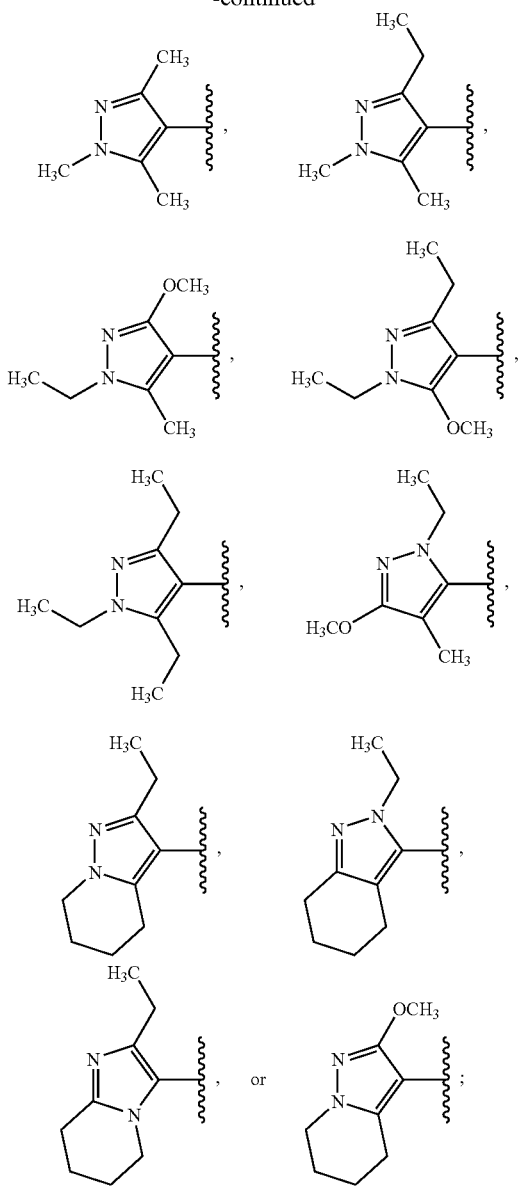

and all other variables are as defined for the second class;

or a pharmaceutically acceptable salt thereof.

A third sub-class of the present invention is a compound of Formula II, wherein $R^{10}$ is:

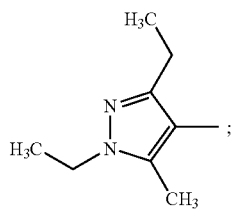

and all other variables are as defined in the second class;

or a pharmaceutically acceptable salt thereof.

A fourth sub-class of the present invention is a compound of Formula II, wherein $R^{10}$ is:

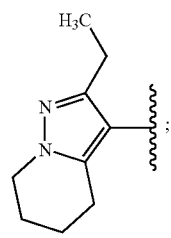

and all other variables are as defined in the second class;

or a pharmaceutically acceptable salt thereof.

The independent syntheses of the diastereomers described above or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

Other embodiments of the present invention include the following:

(a) A pharmaceutical composition comprising a compound of Formula (I) and a pharmaceutically acceptable carrier.

(b) The pharmaceutical composition of (a), further comprising at least one antiviral selected from the group consisting of HIV protease inhibitors, non-nucleoside HIV reverse transcriptase inhibitors, and nucleoside HIV reverse transcriptase inhibitors.

(c) A method for modulating (e.g., inhibiting) CCR5 chemokine receptor activity in a subject which comprises administering to the subject an effective amount of the compound of Formula (I).

(d) A method of preventing or treating infection by HIV in a subject in need thereof which comprises administering to the subject a therapeutically effective amount of a compound of Formula (I).

(e) The method of (d), wherein the compound of Formula (I) is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.

(f) A method of delaying the onset or AIDS or treating AIDS in a subject in need thereof which comprises administering to the subject a therapeutically effective amount of a compound of Formula (I).

(g) The method of (f), wherein the compound is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors (h) A method of modulating (e.g., inhibiting) CCR5 chemokine receptor acitivity in a subject in need thereof which comprises administering to the subject a therapeutically effective amount of the composition of (a) or (b).

(i) A method of preventing or treating infection by HIV in a subject in need thereof which comprises administering to the subject a therapeutically effective amount of the composition of (a) or (b).

(j) A method of treating AIDS or delaying the onset of AIDS in a subject in need thereof which comprises administering to the subject a therapeutically effective amount of the composition of (a) or (b).

Still other embodiments of the present invention include the following:

(k) A pharmaceutical composition which comprises the product prepared by combining (e.g., mixing) an effective amount of a compound of Formula (I) and a pharmaceutically acceptable carrier.

(l) A combination useful for inhibiting HIV integrase, for treating or preventing infection by HIV, or for preventing, treating or delaying the onset of AIDS, which is a therapeutically effective amount of a compound of Formula (I) and a therapeutically effective amount of an HIV infection/AIDS treatment agent selected from the group consisting of HIV/AIDS antiviral agents, immunomodulators, and anti-infective agents.

(m) The combination of (l), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

Additional embodiments of the invention include the pharmaceutical compositions and methods set forth in (a)–(j) above and the compositions and combinations set forth in (k)–(m), wherein the compound employed therein is a compound of one of the embodiments, classes, sub-classes, or aspects of compounds described above. In all of these embodiments, the compound may optionally be used in the form of a pharmaceutically acceptable salt.

As used herein, the term "$C_{1-6}$ alkyl" (or "$C_1$–$C_6$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. Similar terms such as "$C_{1-10}$ alkyl" have analogous meanings.

The term "$C_0$" as employed in expressions such as "$C_{0-6}$ alkyl" means a direct covalent bond.

The term "$C_{2-6}$ alkenyl" (or "$C_2$–$C_6$ alkenyl") means linear or branched chain alkenyl groups having from 2 to 6 carbon atoms and includes all of the hexenyl and pentenyl isomers as well as 1-butenyl, 2-butenyl, 3-butenyl, isobutenyl, 1-propenyl, 2-propenyl, and ethenyl (or vinyl). Similar terms such as "$C_{2-10}$ alkenyl" have analogous meanings.

The term "$C_{2-6}$ alkynyl" (or "$C_2$–$C_6$ alkynyl") means linear or branched chain alkynyl groups having from 2 to 6 carbon atoms and includes all of the hexynyl and pentynyl isomers as well as 1-butynyl, 2-butynyl, 3-butynyl, 1-propynyl, 2-propynyl, and ethynyl (or acetylenyl). Similar terms such as "$C_{2-10}$ alkynyl" have analogous meanings.

The term "$C_{3-8}$ cycloalkyl" (or "$C_3$–$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The term "$C_{3-6}$ cycloalkyl" refers to a cyclic ring selected from cyclopropyl, cyclobutyl, cyclopentyl, and cyclohexyl. Similar terms such as "$C_{5-6}$ cycloalkyl" have analogous meanings.

The term "halogen" (or "halo") refers to fluorine, chlorine, bromine and iodine (alternatively, fluoro, chloro, bromo, and iodo).

The term "$C_{1-6}$ haloalkyl" (which may alternatively be referred to as "$C_1$–$C_6$ haloalkyl" or "halogenated $C_1$–$C_6$ alkyl") means a $C_1$ to $C_6$ linear or branched alkyl group as defined above with one or more halogen substituents. The term "$C_{1-4}$ haloalkyl" has an analogous meaning. Similarly, "$C_{1-6}$ fluoroalkyl" means a $C_1$ to $C_6$ linear or branched alkyl group as defined above with one or more fluorine substituents. Representative examples of suitable fluoroalkyls include the series $(CH_2)_{0-4}CF_3$ (i.e., trifluoromethyl, 2,2,2-trifluoroethyl, 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "—($C_{1-6}$ alkyl)hydroxy" refers to a $C_{1-6}$ alkyl group as defined above which is substituted on one its carbons by a hydroxy group. Exemplary groups include hydroxymethyl, hydroxyethyl, 3-hydroxy-n-propyl, 2-hydroxy-n-propyl, and so forth.

The term "$C_{3-8}$ cycloalkylidenyl" refers to a $C_{3-8}$ cycloalkyl group as defined above in which one of the ring carbons is attached to each of two carbon atoms not in the ring such that the three carbon atoms form a carbon chain or part of a carbon chain. Thus, "—($C_{0-2}$ alkyl)—($C_{3-8}$ cycloalkylidenyl)—($C_{1-2}$ alkyl)" refers to and encompasses such groups as:

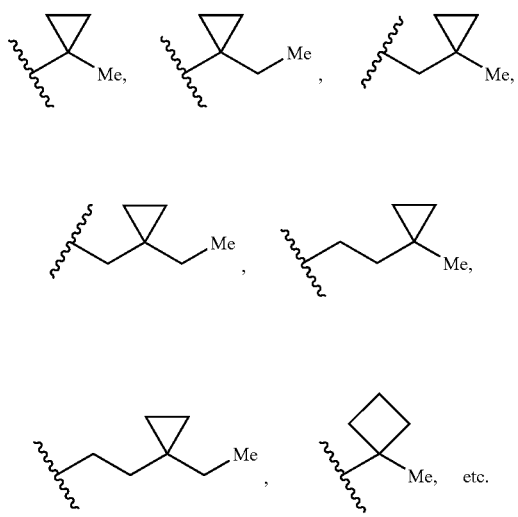

The term "carbocycle" (and variations thereof such as "carbocyclic" or "carbocyclyl") as used herein broadly refers to a $C_3$ to $C_8$ monocyclic, saturated or unsaturated ring or a $C_7$ to $C_{14}$ bicyclic ring system in which the rings are independent or fused and in which each ring is saturated or unsaturated.

The term "aryl" refers to aromatic mono- and polycarbocyclic ring systems, wherein the individual carbocyclic rings in the polyring systems may be fused or attached to each other via a single bond. Suitable aryl groups include, but are not limited to, phenyl, naphthyl, and biphenylenyl.

The term "heterocycle" (and variations thereof such as "heterocyclic" or "heterocyclyl") broadly refers to a 4- to 8-membered monocyclic ring, 7- to 14-membered bicyclic ring system, or an 11 to 16-membered tricyclic ring system, any ring of which is saturated or unsaturated, and which consists of carbon atoms and one or more heteroatoms (e.g., from 1 to 4 heteroatoms) selected from N, O and S, and wherein the nitrogen and sulfur heteroatoms may optionally be oxidized, and the nitrogen heteroatom may optionally be quaternized. The heterocyclic ring may be attached at any heteroatom or carbon atom, provided that attachment results in the creation of a stable structure.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, methylenedioxybenzyl, tetrahydrofuranyl, and tetrahydrothienyl, and N-oxides thereof.

The term "heterocycle" as used herein is also intended to include, but is not limited to, the following groups: methylenedioxyphenyl, imidazopyridyl, imidazopyrimidinyl, imidazopyridazinyl, imidazopyrazinyl, imidazotriazinyl, imidazothiopheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrinmidyl, tetrahydropyrazolopyrazinyl, imidazothiazolyl, and imidazothiadiazolyl.

The term "heterocycle" as used herein is also intended to include, but is not limited to, oxopyridinyl (e.g., 2-oxopyridinyl), oxopiperidinyl, and oxopyrazolyl.

The terms "thiophenyl" and "thienyl" have the same meaning herein and are used interchangeably. Similarly, the following pairs of terms have the same meaning: "indazolyl" and "benzopyrazolyl"; "pyridinyl" and "pyridyl".

Unless expressly set forth to the contrary, an "unsaturated" ring is a partially or fully unsaturated ring.

The term "substituted" in reference to substitution on alkyl, cycloalkyl, phenyl, heterocycle, or some other chemical group is intended to include mono- and poly-substitution by a named substituent to the extent such single and multiple substitution is chemically allowed in any of the named chemical groups.

It is understood that the definition of a substituent at a particular location in a molecule is independent of its definition at other locations in the molecule. Thus, for example, when $Z^1 = -N(R^u)C(=CHR^s)N(R^u)-$, the value of $R^u$ (defined elsewhere) on one of the nitrogens is independent of the value of $R^u$ at the other nitrogen; i.e., they can be the same or different.

Exemplifying the invention are the compounds disclosed in the Examples and the use of these compounds as disclosed herein (e.g., for treating HIV infection or AIDS).

An aspect of the present invention is a compound selected from the group consisting of:

1-{[(3S,4S)-3-{[4-(2-ethyl-4,5,6,7-tetrahydropyrazolo[1,5-a]pyridin-3-yl)piperidin-1-yl]methyl}-4-(3-fluorophenyl)pyrrolidin-1-yl]methyl}cyclopentanecarboxylic acid;

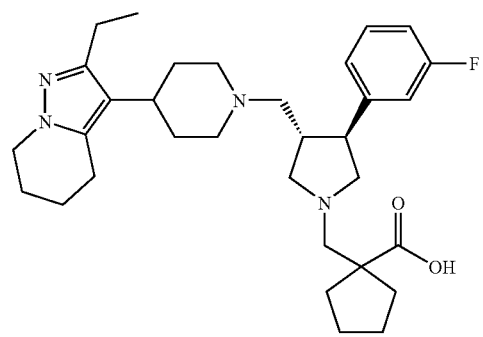

1-{[(3S,4S)-3-{[4-(2-ethyl-4,5,6,7-tetrahydropyrazolo[1,5-a]pyridin-3-yl)piperidin-1-yl]methyl}-4-(3-fluorophenyl)pyrrolidin-1-yl]methyl}cyclohexanecarboxylic acid;

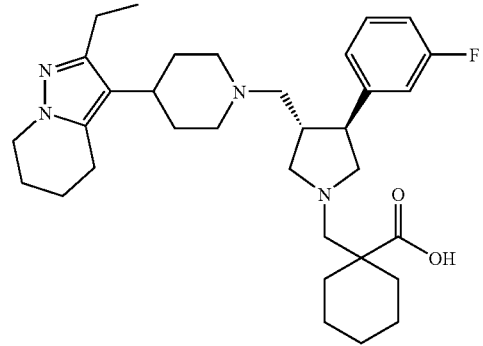

1-{[(3R,4S)-3-{(1R)-1-[4-(1,3-diethyl-5-methyl-1H-pyrazol-4-yl)piperidin-1-yl]ethyl}-4-(3-fluorophenyl)pyrrolidin-1-yl]methyl}cyclobutanecarboxylic acid;

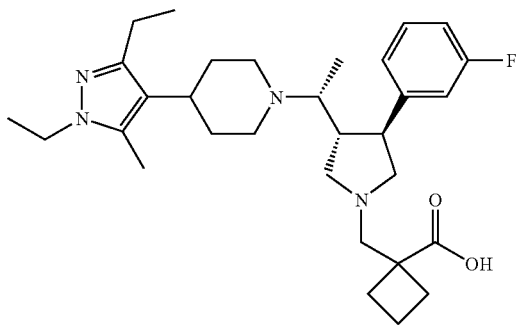

(1R,5R)-3-[((3S,4S)-3-(3,5-difluorophenyl)-4-{[4-(2-ethyl-4,5,6,7-tetrahydropyrazolo[1,5-a]pyridin-3-yl)piperidin-1-yl]methyl}pyrrolidin-1-yl)methyl]bicyclo[3.1.0]hexane-3-carboxylic acid;

1-{[(3R,4S)-3-{(1R)-1-[4-(1,3-diethyl-4-methyl-1H-pyrazol-5-yl)piperidin-1-yl]ethyl}-4-(3-fluorophenyl)pyrrolidin-1-yl]methyl}cyclohexanecarboxylic acid;

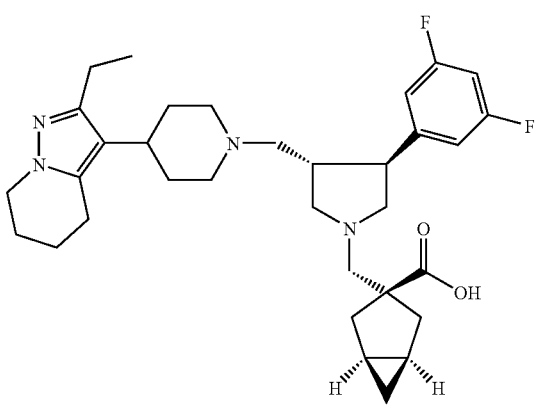

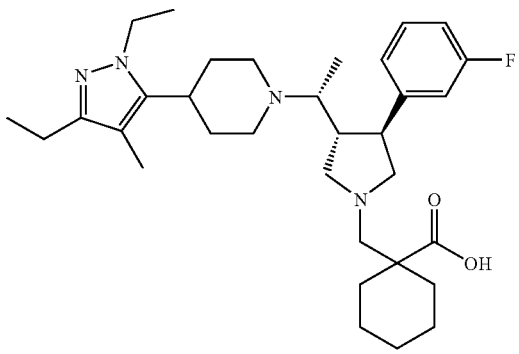

1-{[(3S,4S)-3-{[4-(2-ethyl-4,5,6,7-tetrahydropyrazolo[1,5-a]pyridin-3-yl)piperidin-1-yl]methyl}-4-(3-fluorophenyl)pyrrolidin-1-yl]methyl}cyclobutanecarboxylic acid;

3-[(3R,4S)-3-{(1R)-1-[4-(2-ethyl-4,5,6,7-tetrahydropyrazolo[1,5-a]pyridin-3-yl)piperidin-1-yl]ethyl}-4-(3-fluorophenyl)pyrrolidin-1-yl]-2,2-dimethylpropanoic acid;

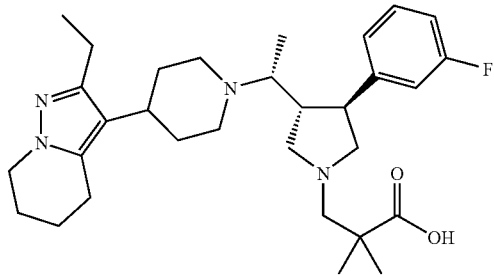

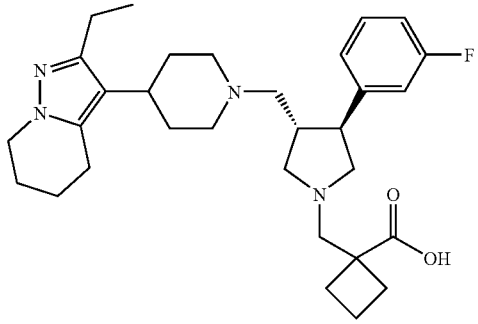

1-{[(3R,4S)-3-{(1R)-1-[4-(1,3-diethyl-4-methyl-1H-pyrazol-5-yl)piperidin-1-yl]ethyl}-4-(3-fluorophenyl)pyrrolidin-1-yl]methyl}cyclopentanecarboxylic acid;

1-{[(3S,4S)-3-{[4-(1,3-diethyl-4-methyl-1H-pyrazol-5-yl)piperidin-1-yl]methyl}-4-(3-fluorophenyl)pyrrolidin-1-yl]methyl}cyclohexanecarboxylic acid;

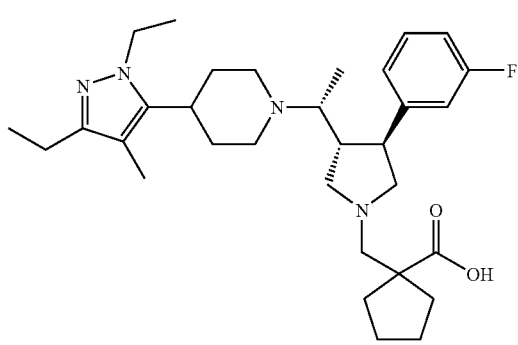

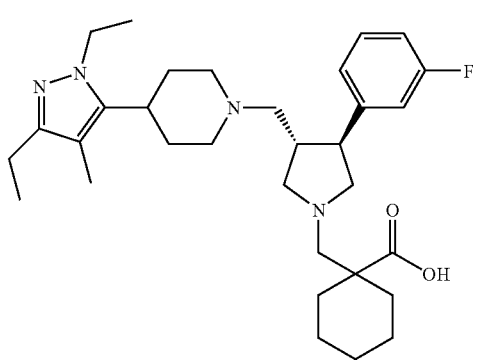

1-{[(3S,4S)-3-{[4-(1,3-diethyl-4-methyl-1H-pyrazol-5-yl)
piperidin-1-yl]methyl}-4-(3-fluorophenyl)pyrrolidin-1-
yl]methyl}cyclopentanecarboxylic acid;

2-ethyl-2-{[(3S,4S)-3-{[4-(2-ethyl-4,5,6,7-tetrahydropyra-
zolo[1,5-a]pyridin-3-yl)piperidin-1-yl]methyl}-4-(3-fluo-
rophenyl)pyrrolidin-1-yl]methyl}butanoic acid;

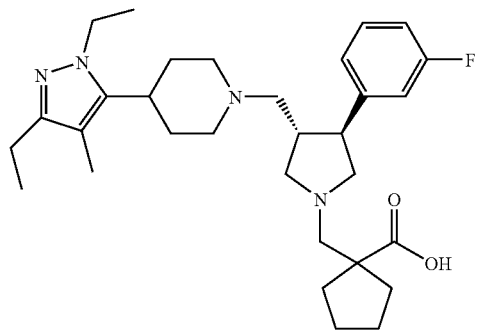

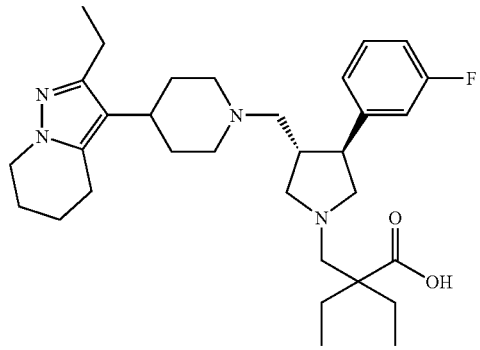

1-{[(3S,4S)-3-{[4-(2-ethyl-4,5,6,7-tetrahydro-2H-indazol-
3-yl)piperidin-1-yl]methyl}-4-(3-fluorophenyl)pyrroli-
din-1-yl]methyl}cyclopentanecarboxylic acid;

2-{[(3S,4S)-3-{[4-(1,3-diethyl-5-methyl-1H-pyrazol-4-yl)
piperidin-1-yl]methyl}-4-(3-fluorophenyl)pyrrolidin-1-
yl]methyl}-2-ethylbutanoic acid;

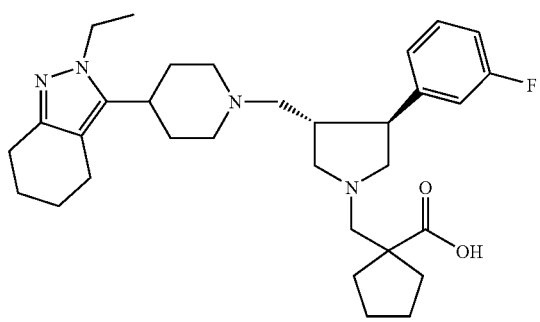

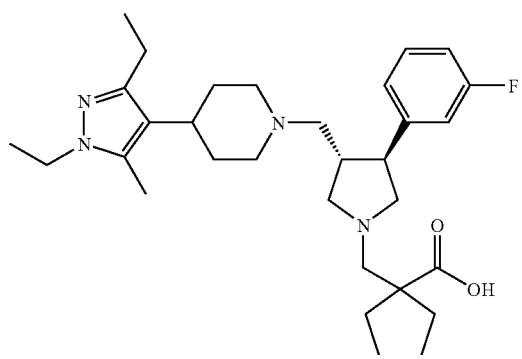

1-{[(3S,4S)-3-{[4-(2-ethyl-4,5,6,7-tetrahydro-2H-indazol-
3-yl)piperidin-1-yl]methyl}-4-(3-fluorophenyl)pyrroli-
din-1-yl]methyl}cyclohexanecarboxylic acid;

(1R,5S)-3-{[(3S,4S)-3-{[4-(1,3-diethyl-4-methyl-1H-pyra-
zol-5-yl)piperidin-1-yl]methyl}-4-(3-fluorophenyl)pyrro-
lidin-1-yl]methyl}bicyclo[3.1.0]hexane-3-carboxylic
acid;

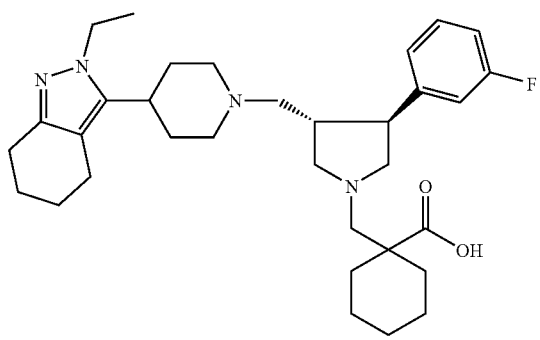

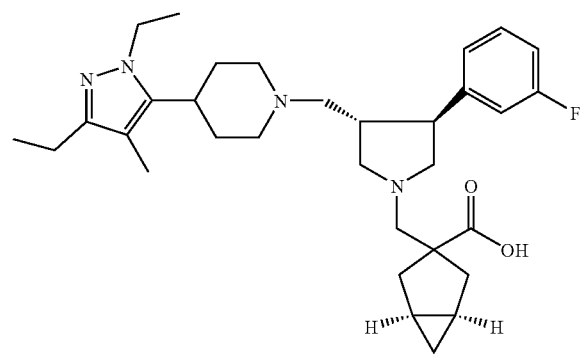

(1R,5S)-3-{[(3S,4S)-3-{[4-(1,3-diethyl-5-methyl-1H-pyrazol-4-yl)piperidin-1-yl]methyl}-4-(3-fluorophenyl)pyrrolidin-1-yl]methyl}bicyclo[3.1.0]hexane-3-carboxylic acid;

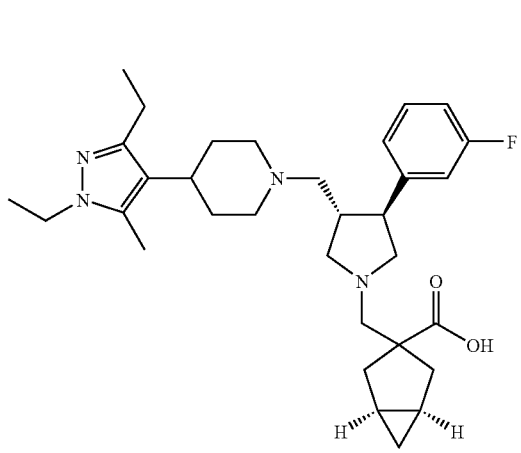

3-[(3S,4S)-3-{[4-(1,3-diethyl-5-methyl-1H-pyrazol-4-yl)piperidin-1-yl]methyl}-4-(3-fluorophenyl)pyrrolidin-1-yl]-2,2-dimethylpropanoic acid;

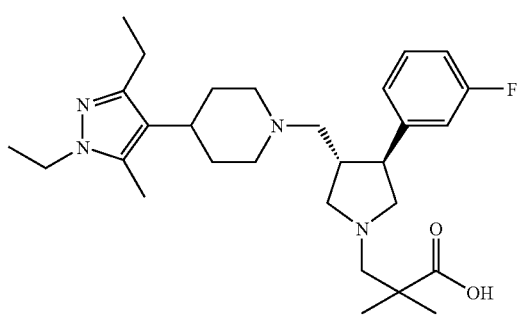

(1R,5S)-3-{[(3R,4S)-3-{(1R)-1-[4-(1,3-diethyl-5-methyl-1H-pyrazol-4-yl)piperidin-1-yl]ethyl}-4-(3-fluorophenyl)pyrrolidin-1-yl]methyl}bicyclo[3.1.0]hexane-3-carboxylic acid;

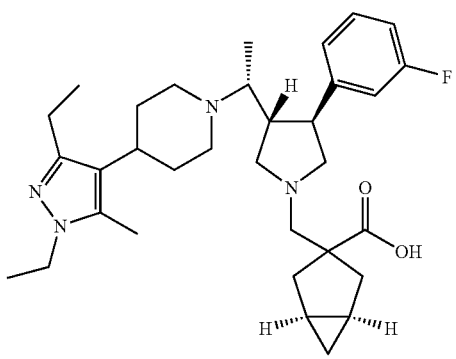

3-[(3R,4S)-3-{(1R)-1-[4-(1,3-diethyl-5-methyl-1H-pyrazol-4-yl)piperidin-1-yl]ethyl}-4-(3-fluorophenyl)pyrrolidin-1-yl]-2,2-dimethylpropanoic acid;

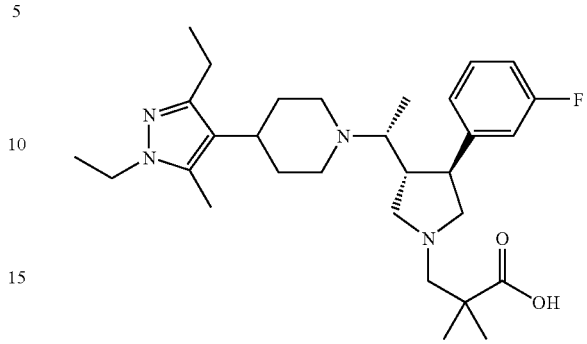

(1R,5R)-3-{[(3S,4S)-3-{[4-(2-ethyl-4,5,6,7-tetrahydropyrazolo[1,5-a]pyridin-3-yl)piperidin-1-yl]methyl}-4-(3-fluorophenyl)pyrrolidin-1-yl]methyl}bicyclo[3.1.0]hexane-3-carboxylic acid;

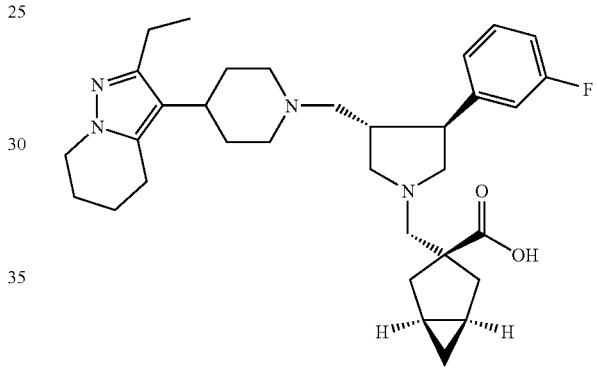

and pharmaceutically acceptable salts thereof.

The subject compounds are useful in a method of modulating (e.g., inhibiting) CCR5 chemokine receptor activity in a patient in need of such modulation (inhibition) comprising the administration of an effective amount of the compound.

The present invention is directed to the use of the foregoing compounds as modulators (inhibitors) of CCR5 chemokine receptor activity.

The utility of the compounds in accordance with the present invention as modulators of CCR5 chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR5 binding. Cell lines for expressing the receptor of interest include those naturally expressing the receptor, such as EOL-3 or THP-1, or a cell engineered to express a recombinant receptor, such as CHO, RBL-2H3, HEK-293. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

In particular, the compounds of the following examples had activity in binding to the CCR5 receptor in the aforementioned assays, generally with an $IC_{50}$ of less than about 5 µM. Such a result is indicative of the intrinsic activity of the compounds in use as modulators of CCR5 chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migrans (e.g., Toxocara), eosinophilic gastroenteritis (e.g., *Anisaki* spp., *Phocanema* ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of CCR5 chemokine receptors. Accordingly, the present invention is directed to the use of these compounds in the preparation and execution of screening assays for compounds which modulate the activity of CCR5 chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the CCR5 chemokine receptors. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating CCR5 chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In an aspect of the present invention, a subject compound may be used in a method of inhibiting the binding of a chemokine to a CCR5 chemokine receptor of a target cell, which comprises contacting the target cell with an amount of the compound which is effective at inhibiting the binding of the chemokine to the CCR5 chemokine receptor.

The subject treated in the methods above is a mammal, preferably a human being, male or female, in whom modulation of CCR5 chemokine receptor activity is desired. "Modulation" as used herein is intended to encompass antagonism, agonism, partial antagonism, inverse agonism and/or partial agonism. In an aspect of the present invention, modulation refers to antagonism of CCR5 chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The term "subject," (alternatively referred to herein as "patient") as used herein refers to an animal, preferably a mammal, most preferably a human, who has been the object of treatment, observation or experiment.

Combined therapy to modulate CCR5 chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR-4, CCR1, CCR2, CCR3 and CCR5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the antiviral agents, immunomodulators, anti-infectives, or vaccines suitable for treating HIV infection and AIDS, and known to those of ordinary skill in the art, including those listed in the following Table:

Antivirals

| Drug Name | Manufacturer | Indication |
|---|---|---|
| Amprenavir<br>141 W94<br>GW 141 | Glaxo Wellcome | HIV infection, AIDS,<br>ARC<br>(protease inhibitor) |
| Abacavir<br>GW 1592<br>1592U89 | Glaxo Welcome | HIV infection, AIDS,<br>ARC<br>(reverse transcriptase<br>inhibitor) |
| Acemannan | Carrington Labs<br>(Irving, TX) | ARC |
| Acyclovir | Burroughs Wellcome | HIV infection, AIDS, ARC,<br>in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen<br>(Los Angeles, CA) | ARC, PGL, HIV positive, AIDS |
| Alpha Interferon | Glaxo Wellcome | Kaposi's sarcoma, HIV, in<br>combination w/Retrovir |
| Ansamycin<br>LM 427 | Adria Laboratories<br>(Dublin, OH)<br>Erbamont<br>(Stamford, CT) | ARC |
| Antibody which<br>neutralizes pH<br>labile alpha aberrant<br>Interferon | Advanced Biotherapy<br>Concepts<br>(Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623<br>(CGP-73547) | Bristol-Myers Squibb/<br>Novartis | HIV infection, AIDS,<br>ARC<br>(protease inhibitor) |
| BMS-234475<br>(CGP-61755) | Bristol-Myers Squibb/<br>Novartis | HIV infection, AIDS,<br>ARC<br>(protease inhibitor) |
| CI-1012 | Warner-Lambert | HIV-1 infection |
| Cidofovir | Gilead Science | CMV retinitis, herpes,<br>papillomavirus |
| Curdlan sulfate | AJI Pharma USA | HIV infection |
| Cytomegalovirus immune<br>globin | MedImmune | CMV retinitis |
| Cytovene<br>Ganciclovir | Syntex | sight threatening CMV<br>peripheral CMV<br>retinitis |
| Delaviridine | Pharmacia-Upjohn | HIV infection, AIDS,<br>ARC<br>(protease inhibitor) |
| Dextran Sulfate | Ueno Fine Chem.<br>Ind. Ltd. (Osaka, Japan) | AIDS, ARC, HIV<br>positive asymptomatic |
| ddC<br>Dideoxycytidine | Hoffman-La Roche | HIV infection, AIDS, ARC |
| ddI<br>Dideoxyinosine | Bristol-Myers Squibb | HIV infection, AIDS, ARC;<br>combination with AZT/d4T |

-continued

| Drug Name | Manufacturer | Indication |
|---|---|---|
| mozenavir (DMP-450) | AVID (Camden, NJ) | HIV infection, AIDS, ARC (protease inhibitor) |
| EL10 | Elan Corp, PLC (Gainesville, GA) | HIV infection |
| Efavirenz (DMP 266) (−) 6-Chloro-4(S)-cyclopropylethynyl-4(S)-trifluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir (ABT-538) | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma in combination with other therapies (reverse transcriptase inhibitor) |

-continued

| Drug Name | Manufacturer | Indication |
| --- | --- | --- |
| ABT-378; Lopinavir | Abbott | HIV infection, AIDS, ARC (protease inhibitor) |
| ABT-378/r; contains lopinavir and ritonavir; Kaletra | Abbott | HIV infection, AIDS, ARC (protease inhibitor) |
| JE2147/AG1776 | Agouron | HIV infection, AIDS, ARC (protease inhibitor) |
| T-20 | Trimeris | HIV infection, AIDS, ARC (fusion inhibitor) |
| T-1249 | Trimeris | HIV infection, AIDS, ARC (fusion inhibitor) |
| atazanavir (BMS 232632) | Bristol-Myers-Squibb | HIV infection, AIDS, ARC (protease inhibitor) |
| PRO 542 | Progenics | HIV infection, AIDS, ARC (attachment inhibitor) |
| PRO 140 | Progenics | HIV infection, AIDS, ARC (CCR5 co-receptor inhibitor) |
| TAK-779 | Takeda | HIV infection, AIDS, ARC (injectable CCR5 receptor antagonist) |
| DPC 681 & DPC 684 | DuPont | HIV infection, AIDS, ARC (protease inhibitors) |
| DPC 961 & DPC 083 | DuPont | HIV infection AIDS, ARC (nonnucleoside reverse transcriptase inhibitors) |
| Trizivir (contains abacavir, lamivudine, and zidovudine) | GlaxoSmithKline | HIV infection, AIDS, ARC (reverse transcriptase inhibitors) |
| tipranavir (PNU-140690) | Boehringer Ingelheim (purchased from Pharmacia & Upjohn) | HIV infection, AIDS, ARC (protease inhibitor) |
| tenofovir disoproxil fumarate | Gilead | HIV infection, AIDS, ARC (reverse transcriptase inhibitor) |
| TMC-120 & TMC-125 | Tibotec | HIV infections, AIDS, ARC (non-nucleoside reverse transcriptase inhibitors) |
| TMC-126 | Tibotec | HIV infection, AIDS, ARC (protease inhibitor) |

Immuno-Modulators

| Drug Name | Manufacturer | Indication |
| --- | --- | --- |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |

-continued

| Drug Name | Manufacturer | Indication |
| --- | --- | --- |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |

Anti-Infectives

| Drug Name | Manufacturer | Indication |
| --- | --- | --- |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidia diarrhea |
| Intraconazole-R51211 | Janssen Pharm. | histoplasmosis; cryptococcal meningitis |
| Trimetrexate | Warner-Lambert | PCP |

Other

| Drug Name | Manufacturer | Indication |
| --- | --- | --- |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption, related to AIDS |

It will be understood that the scope of combinations of the compounds of this invention with HIV/AIDS antivirals, immunomodulators, anti-infectives or vaccines is not limited to the list in the above Table, but includes in principle any combination with any pharmaceutical composition useful for the treatment of HIV infection or AIDS. When employed in combination with the compounds of the invention, the HIV/AIDS antivirals and other agents are typically employed in their conventional dosage ranges and regimens as reported in the art, including the dosages described in the *Physicians' Desk Reference*, 54$^{th}$ edition, Medical Economics Company, 2000. The dosage ranges for a compound of the invention in these combinations are the same as those set forth above just before the above Table.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1(S)-indanyl)-2 (R)-phenylmethyl-4-(S)-hydroxy-5-(1-(4-(2-benzo[b]furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−)6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−)6-chloro-4(S)-cyclopropylethynyl-4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

Compound A in the foregoing Table is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido)-piperazinyl))pentaneamide, preferably administered as the sulfate salt. Compound A can be prepared as described in U.S. Pat. No. 5,646,148.

In such combinations the compound of the present invention and other active agents may be administered separately or in conjunction. In addition, the administration of one element may be prior to, concurrent to, or subsequent to the administration of other agent(s).

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethylamine, diethylamine, piperazine, tris(hydroxymethyl) aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Abbreviations used in the instant specification, particularly the Schemes and Examples, include the following:

Ac=acetyl
Bn=benzyl
BOC or Boc=t-butyloxycarbonyl
Bu=butyl
i-Bu=isobutyl
t-Bu=tert-butyl
n-BuLi=n-butyl lithium
DDQ=2,3-dichloro-5,6-dicyano-1,4-benzoquinone
DIBAL=diisobutylaluminum hydride
DIEA or DIPEA=diisopropylethylamine
DMAP=dimethylaminopyridine
DMF=N,N-dimethylformamide
DMSO=dimethylsulfoxide
EDC or EDAC=1-ethyl-3-(3-dimethylaminopropyl) carbodiimide
Et=ethyl
ether=diethyl ether
h=hour(s)
HMDS=hexamethyldisilazyl
LDA=lithium diisopropylamide
LHMDS or LiIMDS=lithium hexamethyldisilazide
Me=methyl
min=minute(s)
Ph=phenyl
Pr=propyl
i-Pr=isopropyl
PMB=p-methoxybenzyl
rt=room temperature
sat'd=saturated aqueous
TBSO=t-butyldimethylsiloxy
TEA=triethylamine
TFA=trifluoroacetic acid The compounds of the present invention can be readily prepared according to the following reaction schemes and examples, or modifications thereof. Starting materials can be made from procedures known in the art or as illustrated. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, the variables are as defined above.

SCHEME 1

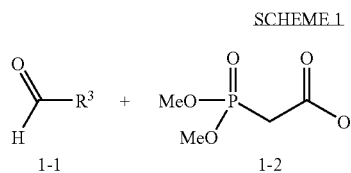

The preparation of cinnamate esters such as 1–3 (wherein $R^3$=an aromatic group) as intermediates that can be used for the synthesis of compounds within the scope of the instant invention is detailed in Scheme 1. Cinnamate esters of structure 1–3 can be obtained commercially or can be synthesized by reacting a suitable aromatic aldehyde 1–1 with a phosphonoacetate such as 1–2 or a stabilized Wittig reagent in the presence of sodium hydride or other bases such as sodium, lithium or potassium hexamethyldisilazide, potassium t-butoxide, and the like. The aldehyde 1–1 can be obtained commercially or can be prepared in a variety of ways from commercial materials (see March J. "Advanced Organic Chemistry", 4th ed., John Wiley & Sons, New York, pp. 1270–1271 (1992)).

SCHEME 2

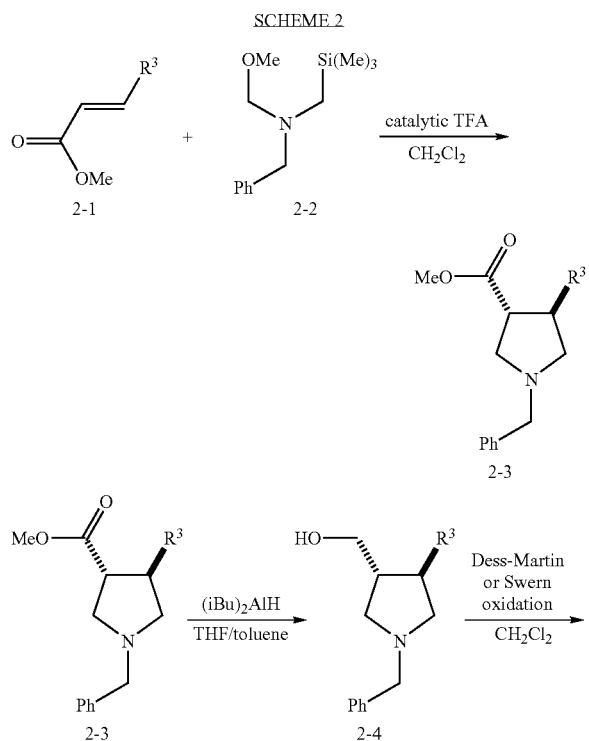

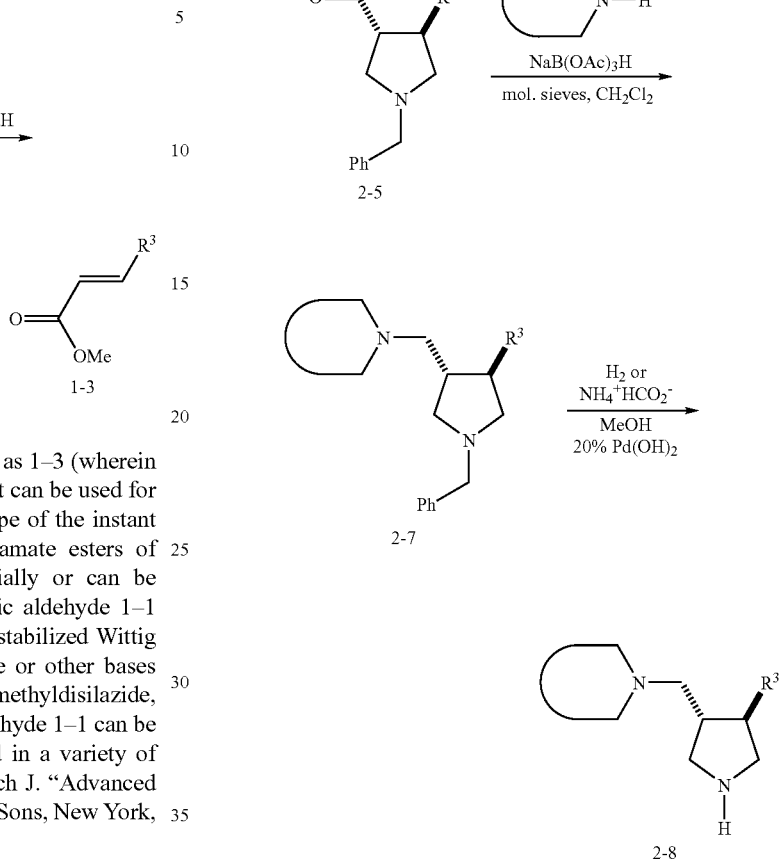

The preparation of compounds within the scope of the instant invention which bear a 1,3,4-trisubstituted pyrrolidine framework is detailed in Scheme 2. Treatment of a trans-cinnamic ester such as 2-1 with commercially available N-benzyl-N-methoxymethyl-N-(trimethylsilyl)-methylamine (2-2) in the presence of a substoichiometric amount of an acid such as TFA, titanium tetrafluoride, lithium fluoride or cesium fluoride, according to the procedure of Padwa et al (*J. Org. Chem.* 1987, 52, 235) preferentially affords the 3,4-trans pyrrolidine 2-3. Executing this sequence starting from the cis-cinnamic ester results in preferential formation of the 3,4-cis pyrrolidine. Reduction of ester 2-3, for example, with diisobutylaluminum hydride, lithium aluminium hydride, or sodium bis(2-methoxyethoxy)aluminum hydride, provides the primary alcohol 2-4. Oxidation to the aldehyde 2-5 can be carried out under numerous conditions, such as with the Dess-Martin periodinane, with DMSO and oxalyl chloride at low temperature, followed by triethylamine (Swern oxidation), or with various chromium trioxide-based reagents (see March J. "Advanced Organic Chemistry", 4th ed., John Wiley & Sons, New York, pp. 1167–1171 (1992)). Reductive amination with cyclic amine 2-6 then provides diamine 2-7, which can itself be a chemokine receptor modulator. Alternatively, the N-benzyl group is cleaved in a hydrogen atmosphere or with ammonium formate in the presence of 20% palladium hydroxide to provide the secondary amine 2-8.

SCHEME 3

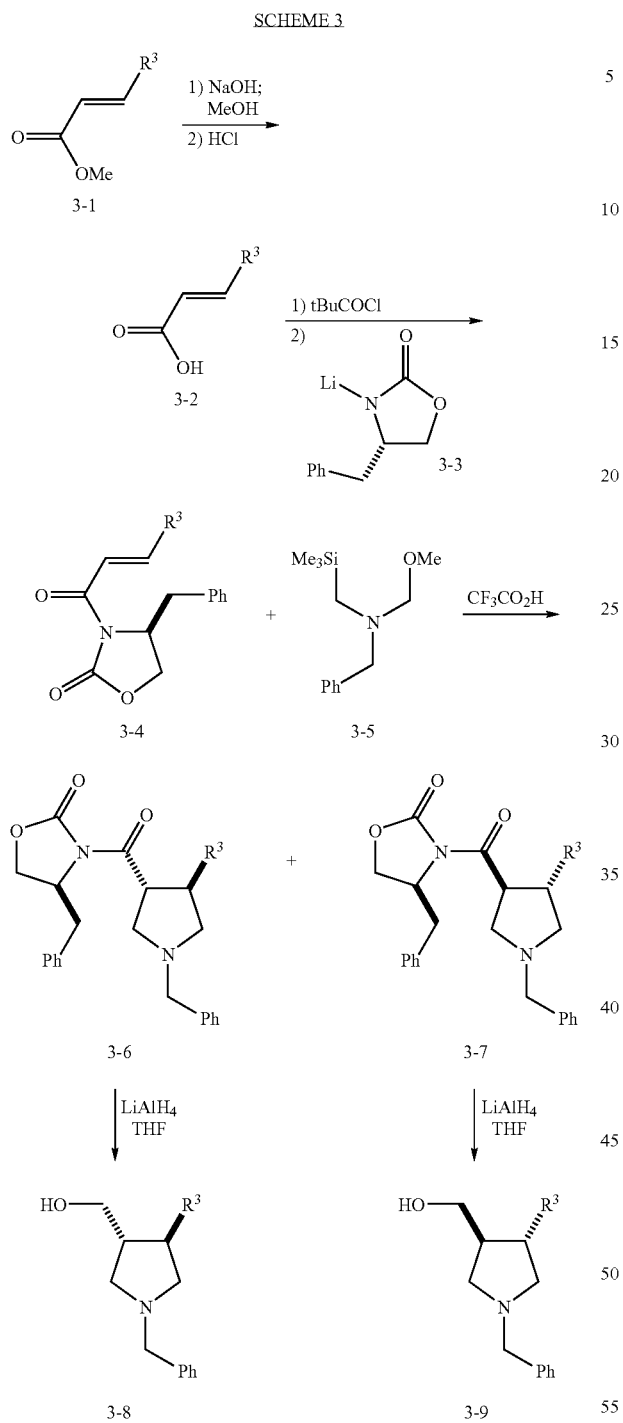

SCHEME 4

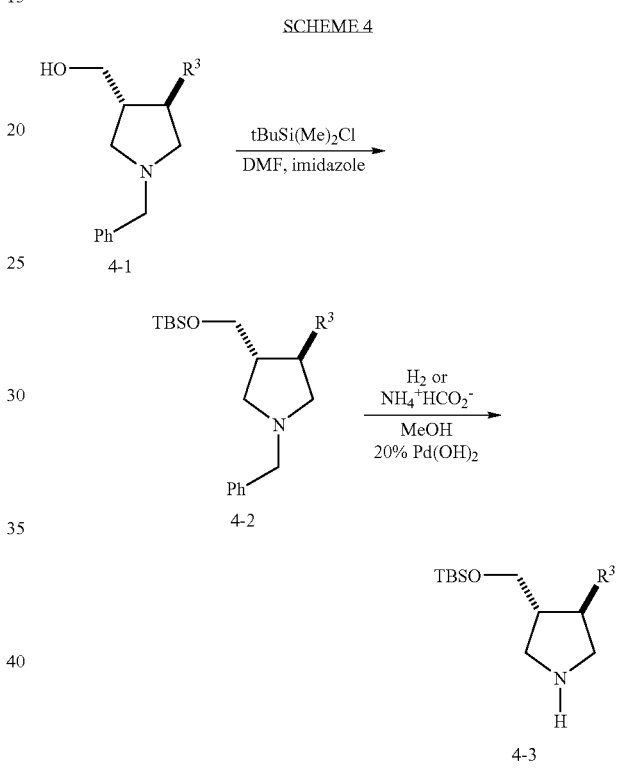

fluoride or cesium fluoride according to the procedure of Padwa et al (*J. Org. Chem.* 1987, 52, 235) affords the diastereomeric pyrrolidines 3-6 and 3-7, which can be separated by flash chromatography, preparative thin layer chromatography, medium pressure liquid chromatography, high pressure liquid chromatography, fractional crystallization, or similar methods known in the art. The separated products are then individually reduced, for example with lithium alumium hydride (LAH) or other strong hydride reducing agents, to provide pyrrolidines 3-8 and 3-9 in optically enriched form.

Scheme 3 shows the preparation of optically pure pyrrolidine intermediates. Hydrolysis of unsaturated ester 3-1 provided acid 3-2, which is converted to diacyl derivative 3-4 by activation of the acid group, for example by formation of a mixed anhydride with pivaloyl chloride, followed by reaction with the lithium salt of 4-(S)-benzyloxazolidin-2-one (3-3). Treatment of 3-4 with commercially available N-benzyl-N-methoxymethyl-N-(trimethylsilyl)-methylamine (2-2) in the presence of a substoichiometric amount of an acid such as TFA, titanium tetrafluoride, lithium Preparation of a protected pyrrolidine for use as an intermediate in the synthesis of compounds in the instant invention is shown in Scheme 4. The pyrrolidine 4-1 (prepared as shown in Schemes 2 and 3) is protected with a suitable protecting group such as t-butyl-dimethylsilyl to provide silyl ether 4-2. Other silyl groups can also be used in this role, as can other protecting groups for a hydroxy residue (see Greene, T. W.; Wuts, P. G. M. "Protective Groups in Organic Synthesis", 2nd edition, Wiley-Interscience, New York, pp. 10–143 (1991)), subject to the group being stable to conditions used to remove the benzyl group and being removable under conditions that would not adversely affect the remainder of the molecule. Removal of the benzyl group on nitrogen is then carried out by hydrogenolysis, for example by transfer hydrogenation with ammonium formate in the presence of 20% palladium hydroxide or with catalytic hydrogenation with 10% palladium on carbon under one or more atmospheres of hydrogen. Alternatively, compound 4-1 can be debenzylated first under the conditions noted above and then silylated on the hydroxy group, to provide 4-3.

SCHEME 5

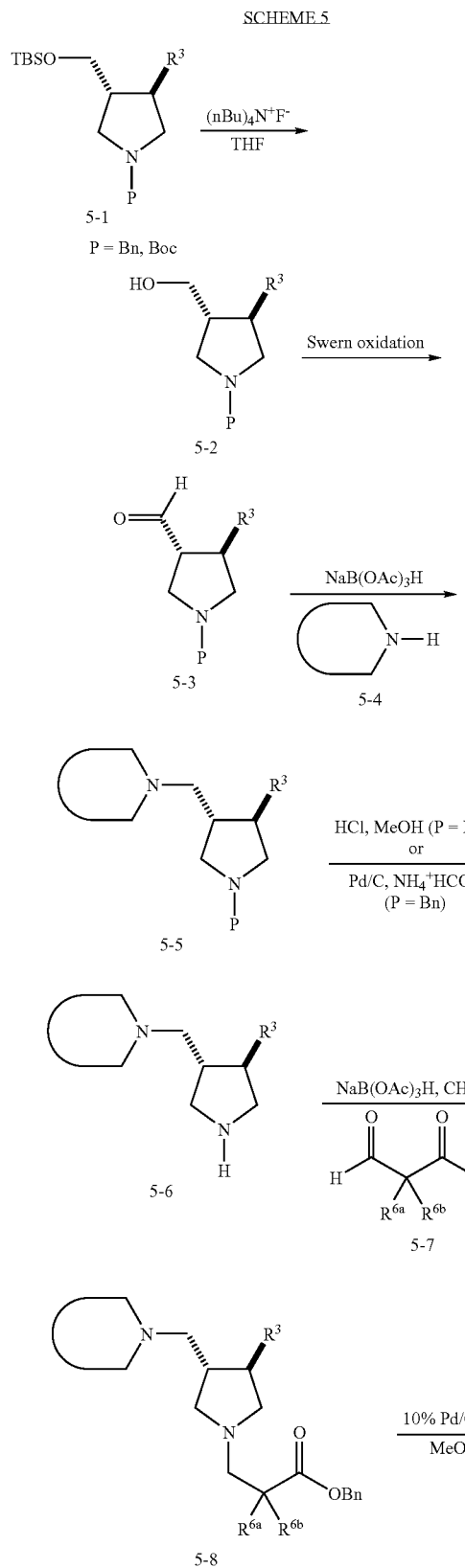

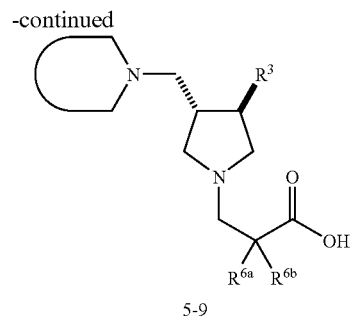

One method of preparing compounds within the scope of the instant invention is given in Scheme 5. Doubly protected pyrrolidine 5-1 (obtained either as shown in Scheme 4 for 4-2 when P=benzyl or by protection of 4-3 with Boc anhydride in THF/water in the presence of triethylamine when P=Boc) is desilylated with tetrabutylammonium fluoride in THF to provide alcohol 5-2. Oxidation of 5-2 to 5-3 is carried out using Swern's oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 5-4 then provides diamine 5-5. Deprotection of the pyrrolidine nitrogen, when P=Boc, can be carried out with HCl in methanol or with trifluoroacetic acid and anisole in dichloromethane, to give secondary amine 5-6. When P=benzyl, debenzylation is carried out in the presence of palladium on carbon as a catalyst, using either hydrogen gas or ammonium formate to effect transfer hydrogenation. Reductive amination with formyl ester 5-7 then provides pyrrolidine 5-8. Removal of the benzyl group can be carried out under standard reductive conditions, for example, hydrogen gas in the presence of a supported or unsupported palladium catalyst, to afford acid 5-9. Alternatively, if a 4-methoxybenzyl ester is utilized in place of the benzyl ester of compound 5-7, then the final deprotection can be carried out under acid conditions, for example, formic acid at 55° C. This latter approach is useful if the parent molecule contains functionality sensitive to catalytic hydrogenation.

SCHEME 6

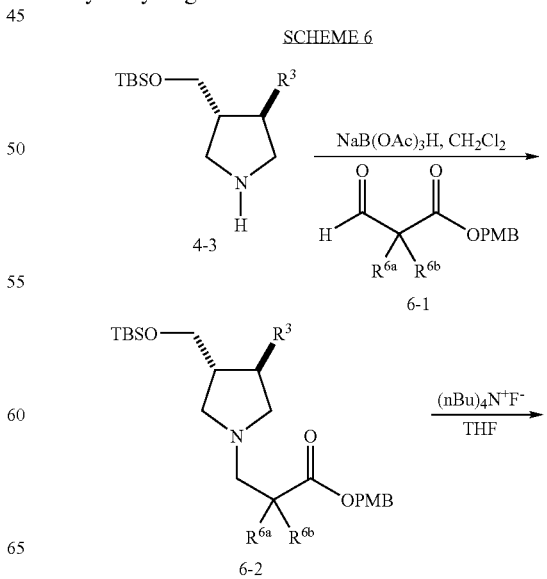

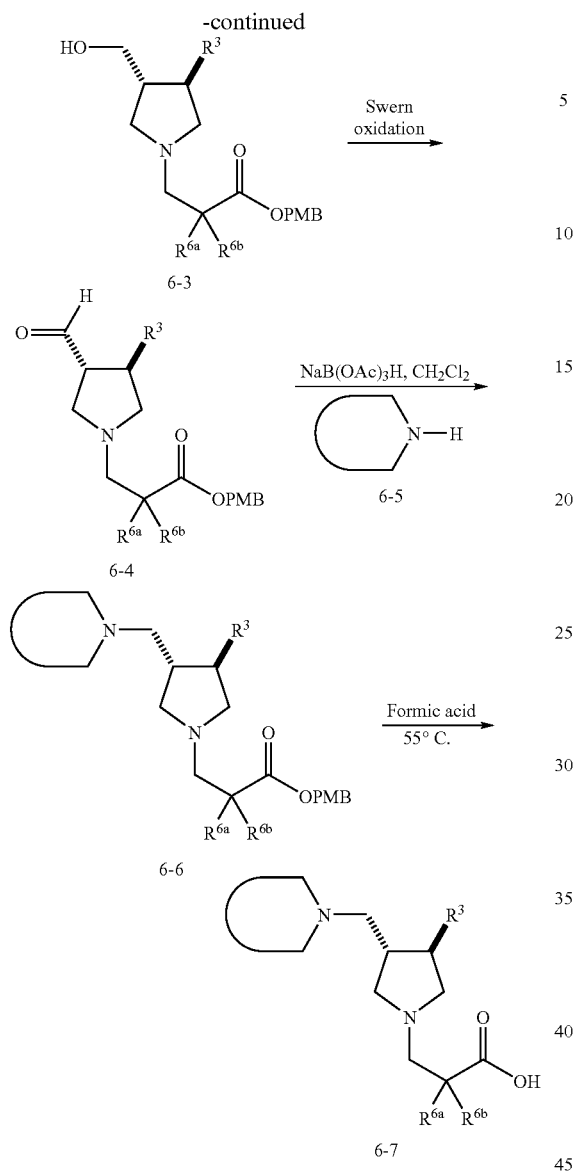

Another method for preparing compounds in the instant invention is shown in Scheme 6. Reductive amination of pyrrolidine 4-3 with aldehyde ester 6-1 affords pyrrolidine 6-2. Removal of the silyl protecting group with tetrabutylammonium fluoride provides alcohol 6-3, which can be oxidized under standard conditions, for example the Swern oxidation, to give aldehyde 6-4.

Reductive amination of 6-4 with a suitable secondary amine 6-5 yields ester 6-6 which can be deprotected under acidic conditions, for example, with formic acid, to afford compound 6-7.

SCHEME 7

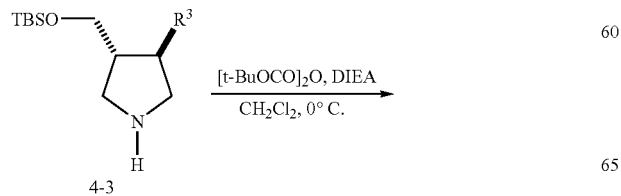

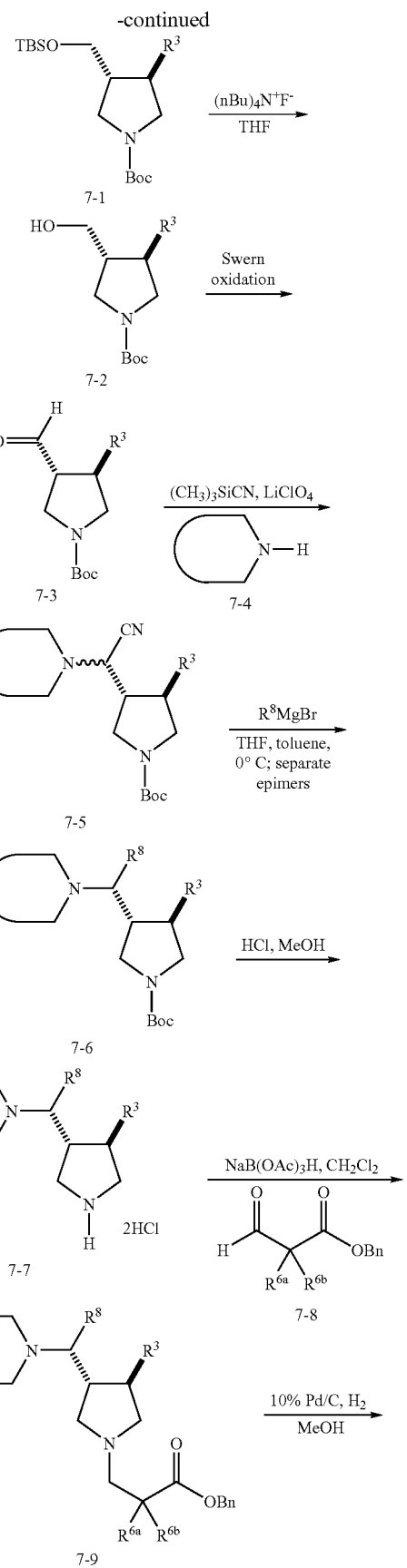

-continued

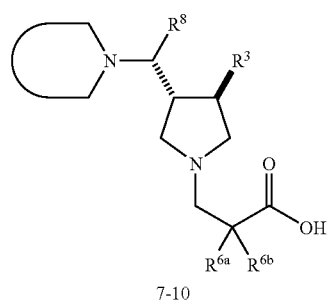

7-10

A method for preparing compounds in the instant invention wherein an additional substituent $R^8$ is present is given in Scheme 7. Protection of pyrrolidine 4-3 with Boc anhydride under standard conditions provides doubly protected pyrrolidine 7-1, which can be desilylated by exposure to tetrabutylammonium fluoride in THF, affording 7-2. Oxidation of 7-2 to aldehyde 7-3 is carried out using Swern's oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Treatment of 7-3 with a secondary amine 7-4, and trimethylsilyl cyanide in the presence of lithium perchlorate affords cyanoamine 7-5. Treatment of 7-5 with a suitable organomagnesium reagent $R^8MgBr$ yields the branched compound 7-6. The diastereomers formed in this process can be separated at this stage, or at any point later in the synthesis by standard methods, including fractional crystallization, column chromatography, flash chromatography, high pressure liquid chromatograghy (HPLC) or medium pressure liquid chromatography (MPLC), optionally by use of a stationary phase derivatized with chiral, non-racemic groups to enable separation of enantiomers and to enhance separation of isomeric mixtures. The Boc group of 7-6 can be removed under acidic conditions, for example hydrochloric acid in methanol, to afford secondary pyrrolidine 7-7. Reductive amination with aldehyde 7-8 under mild conditions, for example with sodium cyanoborohydride in methylene chloride, provides ester 7-9. Removal of the benzyl protecting group by catalytic reduction then affords compound 7-10.

-continued

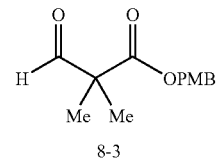

8-3

Synthesis of aldehyde esters such as 6-1 and 7-8 can be carried out by a number of routes, one of which is shown in Scheme 8. The available hydroxy acid 8-1 is esterified with a suitable protecting group (such as a para-methoxybenzyl group) in the presence of a suitable base (such as triethylamine or DIEA), to give ester 8-2. Oxidation of 8-2, for example by Swern oxidation, then affords aldehyde 8-3.

SCHEME 9

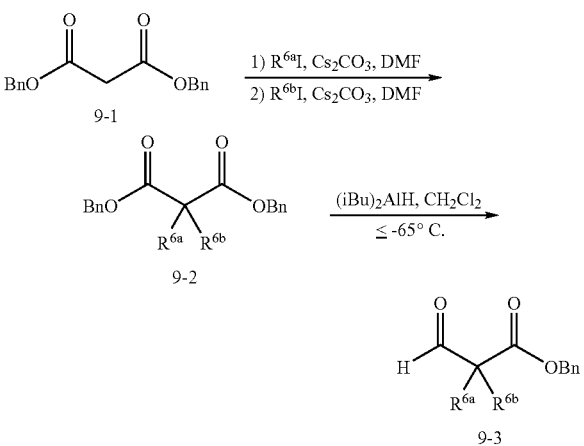

Synthesis of aldehyde ester 6-1 where the $R^6$ substituents are distinct or identical can be accomplished as shown in Scheme 9. Alkylation of dibenzyl malonate with a suitable alkylating agent, such as an alkyl iodide, bromide, toluenesufonate and the like, in the presence of a base such as cesium carbonate, potassium carbonate, or other agents of moderate basicity, followed by repetition of the procedure with a second alkyl halide or alkyl toluenesulfonate, provides dialkylated product 9-2. Treatment of diester 9-2 with di-isobutylaluminum hydride at low temperature affords ester aldehyde 9-3.

SCHEME 8

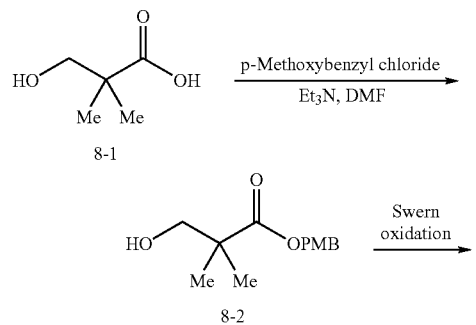

SCHEME 10

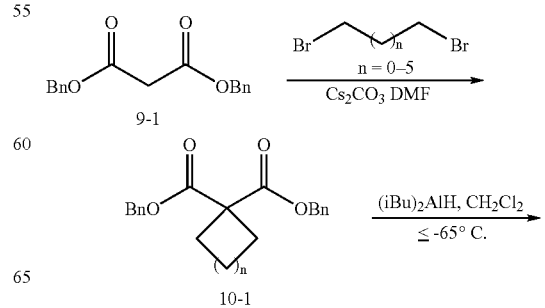

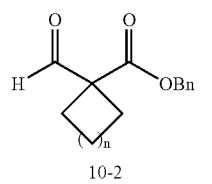

10-2

Synthesis of aldehyde ester 6-1 where the $R^{6a}$ and $R^{6b}$ form a ring substituents can be accomplished as shown in Scheme 10. Dialkylation of dibenzyl malonate with a suitable dialkylating agent, such as an alkyl diiodide, dibromide, ditoluenesufonate and the like, in the presence of a base such as cesium carbonate, potassium carbonate, or other agents of moderate basicity, provides cyclic derivative 10-1. Treatment of diester 10-1 with di-isobutylaluminum hydride at low temperature affords ester aldehyde 10-2. An analogous scheme can be used for cyclic derivatives containing a heteroatom in the ring by selection of the appropriate precursor.

SCHEME 11

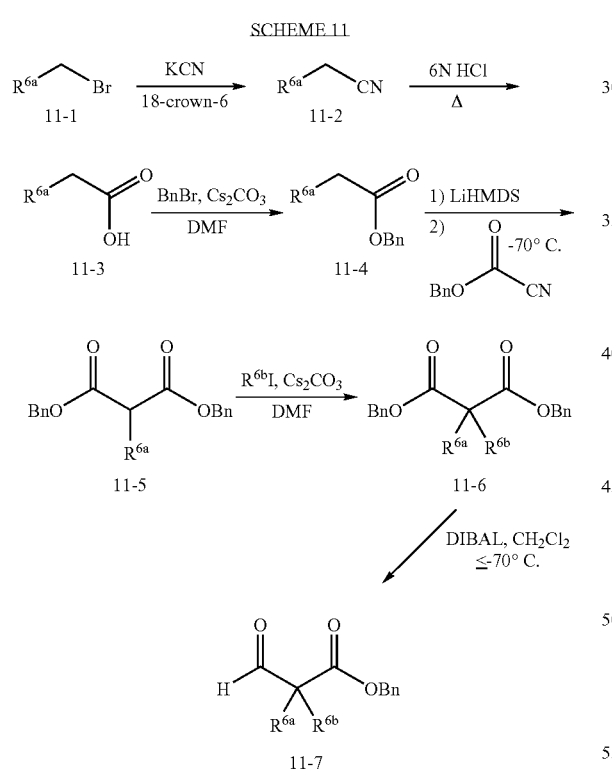

An alternative synthesis of aldehyde ester intermediates is given in Scheme 11. Treatment of a commercially available alkyl methyl bromide with potassium cyanide in the presence of 18-crown-6 provides nitrile 11-2. Hydrolysis under acidic conditions affords acid 11-3. Esterification with benzyl bromide in the presence of cesium carbonate in DMF yields ester 11-4. Deprotonation of ester 11-4 with a strong, non-nucleophilic base, such as lithium hexamethyldisilazide, followed by treatment with benzyl cyanoformate, provides diester 11-5, which can be alkylated with a suitably activated haloalkyl group to provide dialkylated product 11-6. Reduction with DIBAL at low temperature then provides the desired intermediate 11-7.

SCHEME 12

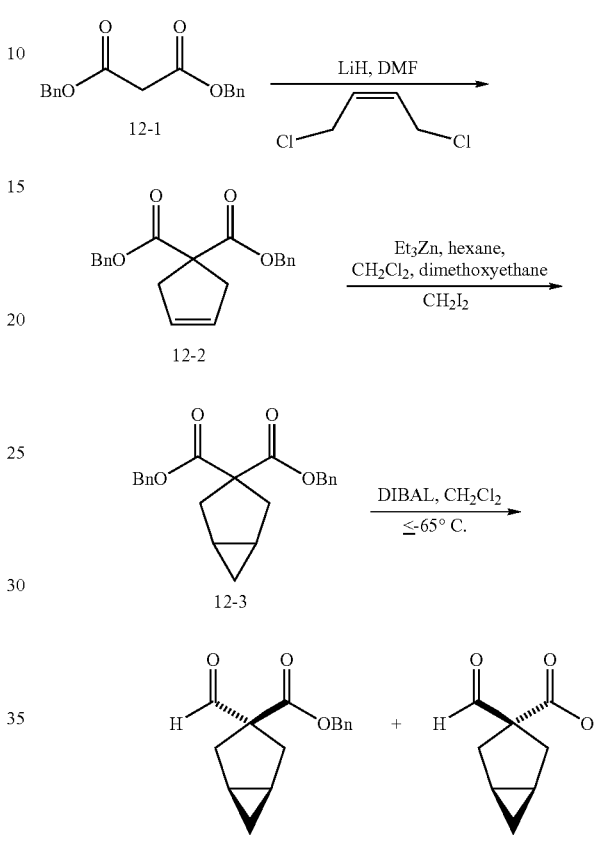

One sythesis of a bicyclic aldehyde ester intermediate is given in Scheme 12. Treatment of dibenzyl malonate with lithium hydride in DMF followed by addition of 1,4-dichloro-cis-butene affords cyclopentene 12-2. Treatment of this olefin with diethylzinc and diiodomethane in methylene chloride and dimethoxyethane provides bicycle 12-3. Exposure to diisobutylaluminum hydride at or below −65° C. then yields a mixture of the aldehydes 12-4 and 12-5, which can be separated at this stage and employed individually as described above.

SCHEME 13

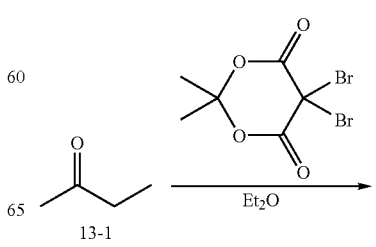

13-1

-continued

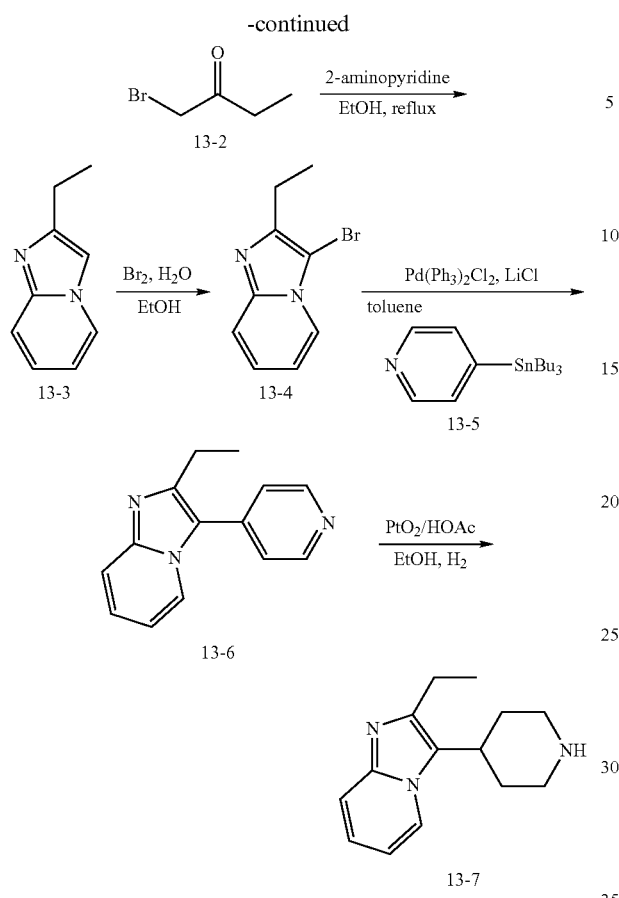

One synthesis of a secondary amine intermediate is given in Scheme 13. Bromination of 2-butanone, followed by condensation with 2-aminopyridine, affords imidazopyridine 13-3. Bromination and then palladium-catalysed coupling with the pyridyl stannane 13-5 provides pyridine derivative 13-6, which upon hydrogenation under acidic conditions yield intermediate 13-7.

SCHEME 14

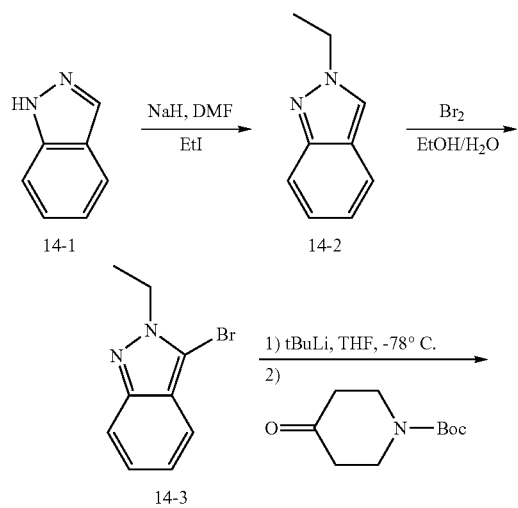

-continued

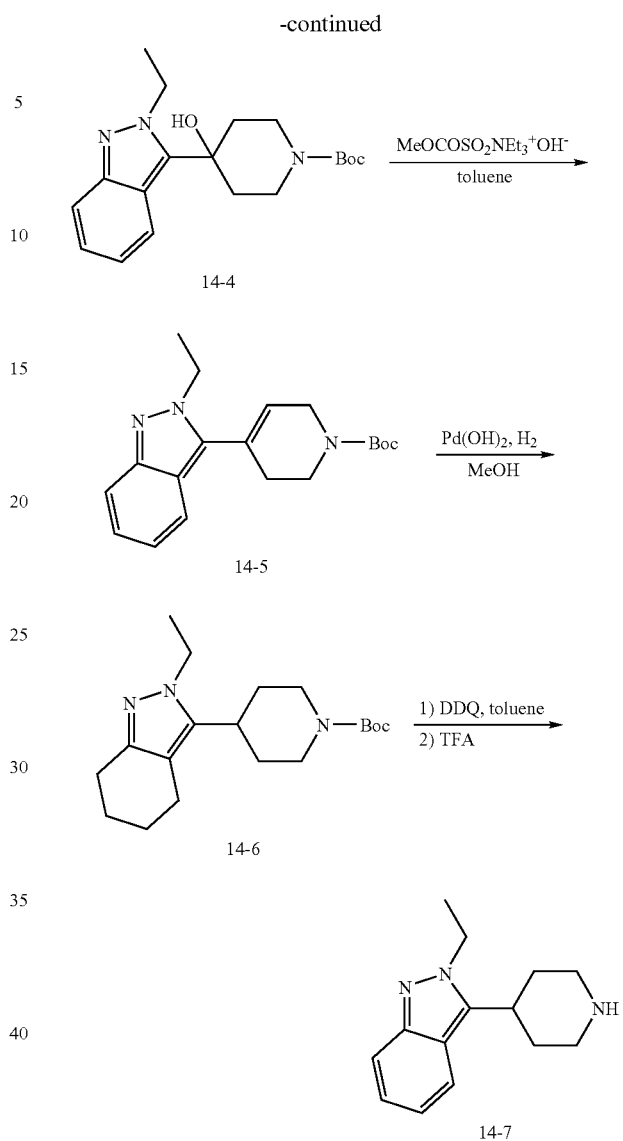

A synthesis of a secondary amine intermediate bearing an indazole substituent is given in Scheme 14. Alkylation of indazole with sodium hydride and then ethyl iodide affords the 2-alkylindazole derivative 14-2. Bromination under standard conditions provides bromide 14-3. Halogen-metal exchange, followed by trapping with the indicated piperidone derivative affords adduct 14-4, which can be dehydrated to yield 14-5. Hydrogenation produces 14-6, which can itself be employed as a secondary amine intermediate. Alternatively, it can be oxidized with DDQ and then treated with TFA to provide intermediate 14-7 as its TFA salt.

SCHEME 15

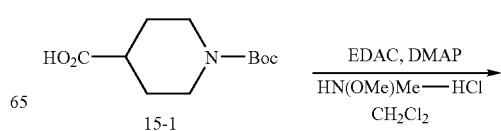

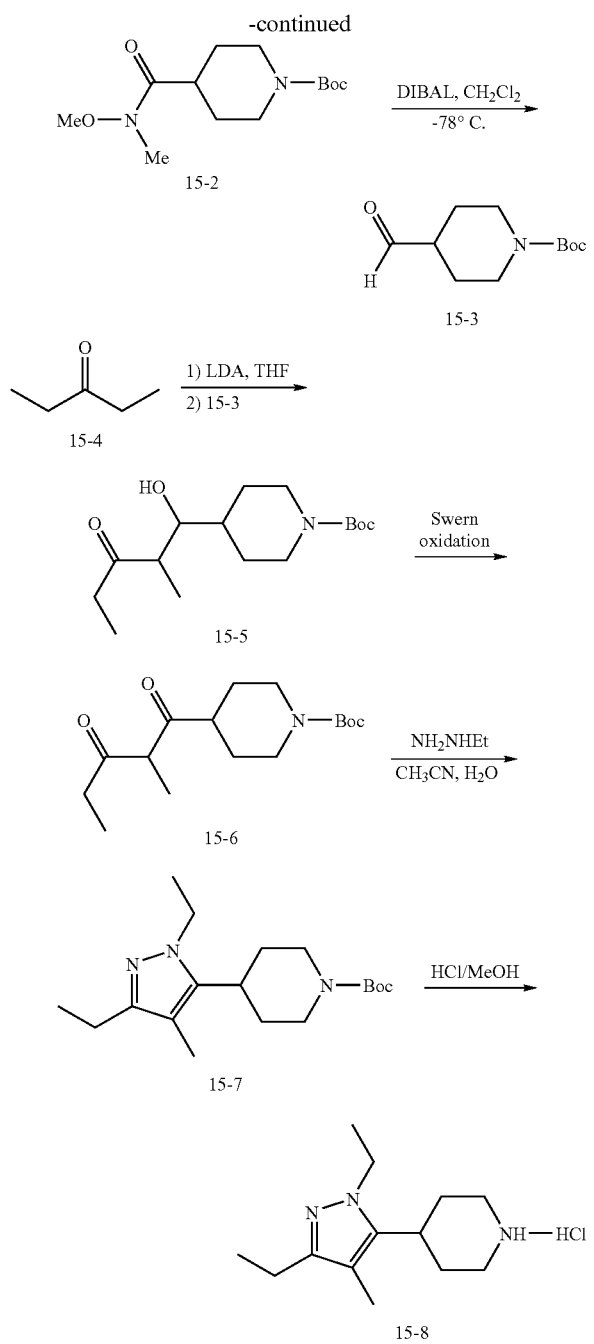

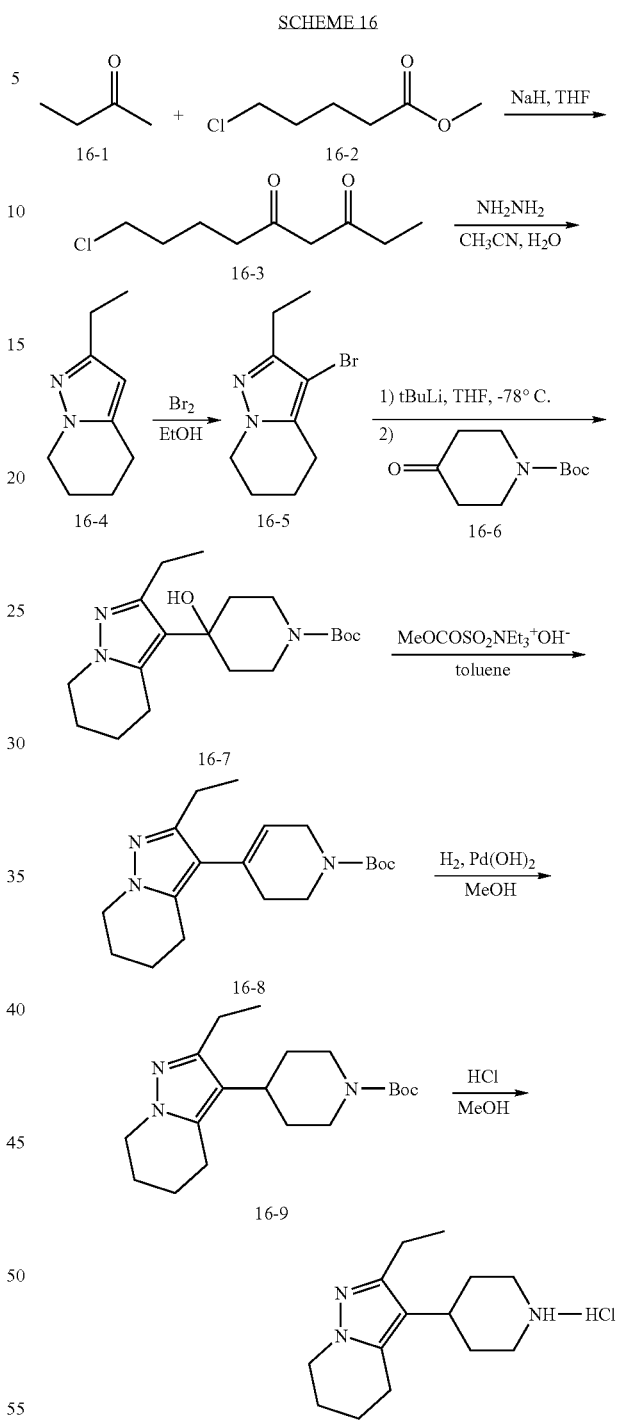

One synthesis of a secondary amine bearing a monocyclic pyrazole substituent is given in Scheme 15. Conversion of the Weinreb amide of Boc-protected isonipecotic acid to the aldehyde can be accomplished by treatment with DIBAL at low temperature in methylene chloride, to give aldehyde 15-3. Separately, formation of the lithium enolate of 3-pentanone, followed by addition of 15-3, affords aldol 15-5. Oxidation to the diketone followed by treatment with ethylhydrazine in acetonitrile/water affords the pyrazole 15-7. Deprotection under acidic conditions then provides intermediate 15-8. Other substituents on the pyrazole nitrogen can be synthesized by utilizing other mono-substituted hydrazines in the condensation step with 15-6.

One synthesis of a secondary amine bearing a bicyclic pyrazole-based substituent is given in Scheme 16. Condensation of 2-butanone and methyl 5-chlorovalerate in the presence of sodium hydride in THF affords diketone 16-3. Treatment of this compound with hydrazine in acetonitrile/water provides pyrazolopiperidine 16-4, which upon exposure to bromine in ethanol yields bromide 16-5. Halogen-metal exchange of 16-5, followed by addition of ketone 16-6, affords 16-7. Dehydration in toluene and then hydrogenation under standard conditions provides piperidine 16-9, which can then be deprotected under acidic conditions, for example HCl in methanol, to afford desired secondary amine 16-10.

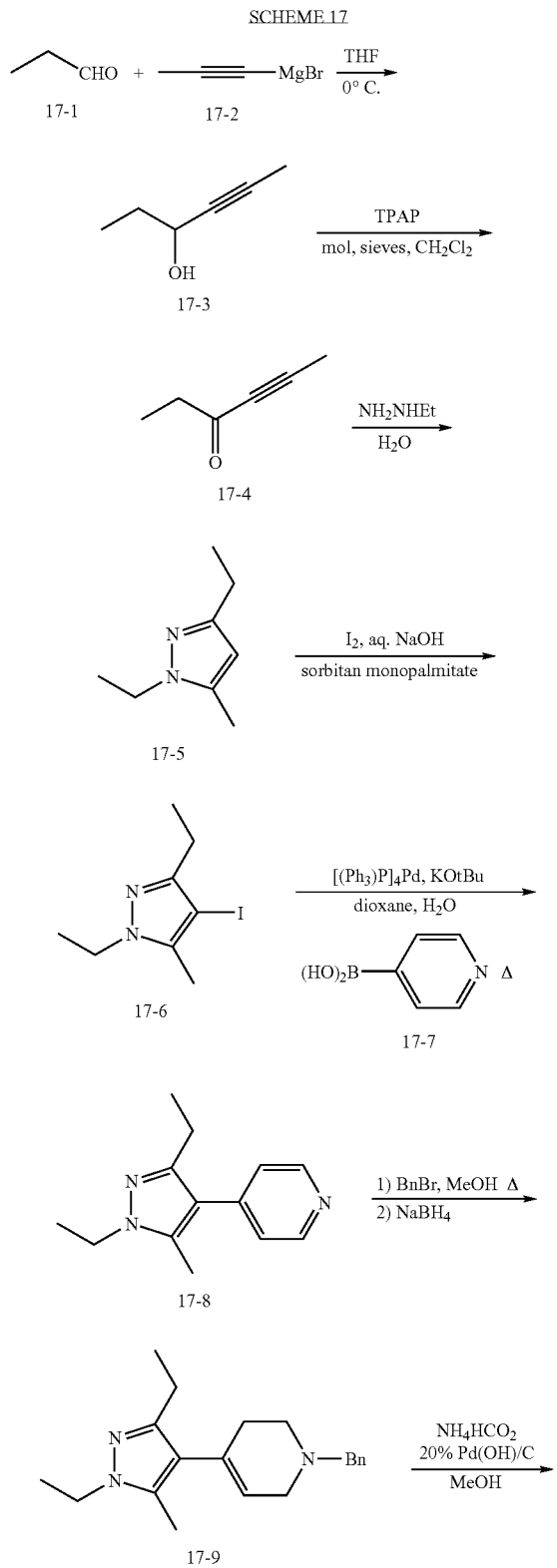

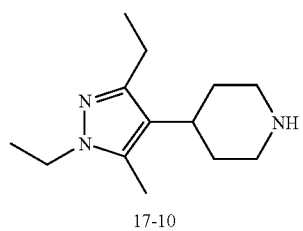

Another synthesis of a secondary amine bearing a monocyclic pyrazole substituent is given in Scheme 17. Addition of anion 17-2 to propionaldehyde affords alcohol 17-3, which can be oxidized to ketone 17-4. Treatment with ethylhydrazine yields pyrazole 17-5, which can be iodinated under phase-transfer conditions to provide iodide 17-6. Coupling of this aldehyde with 4-pyridineboronic acid in the presence of a suitable palladium catalyst affords 17-8. Alkylation of 17-8 with benzyl bromide, followed by reduction with sodium borohydride, yields tetrahydropyridine 17-9. Catalytic hydrogenation then provides secondary intermediate 17-10. The pyrazole nitrogen substituent can be varied by utilizing alternative mono-substituted hydrazine derivatives in the condensation with 17-4.

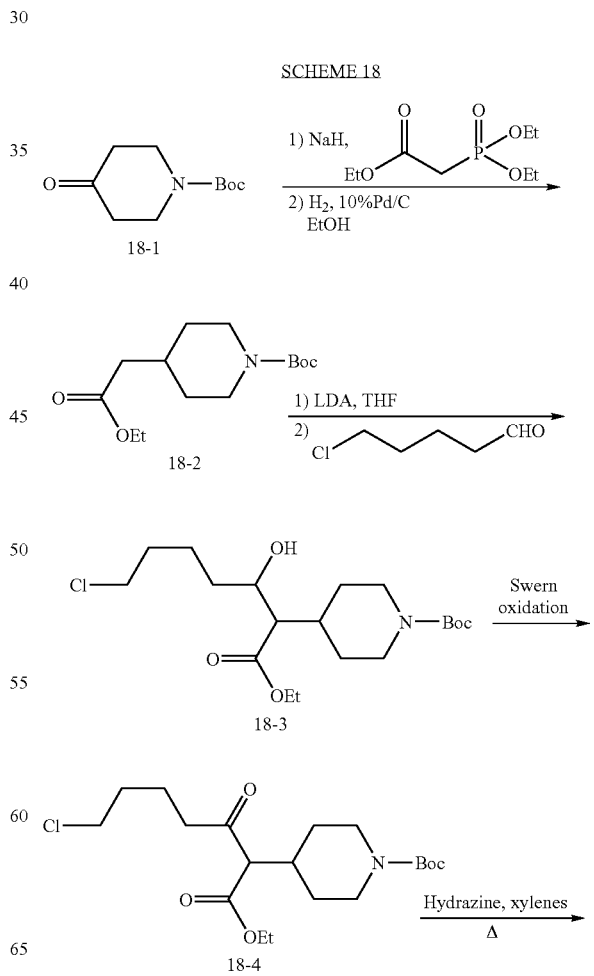

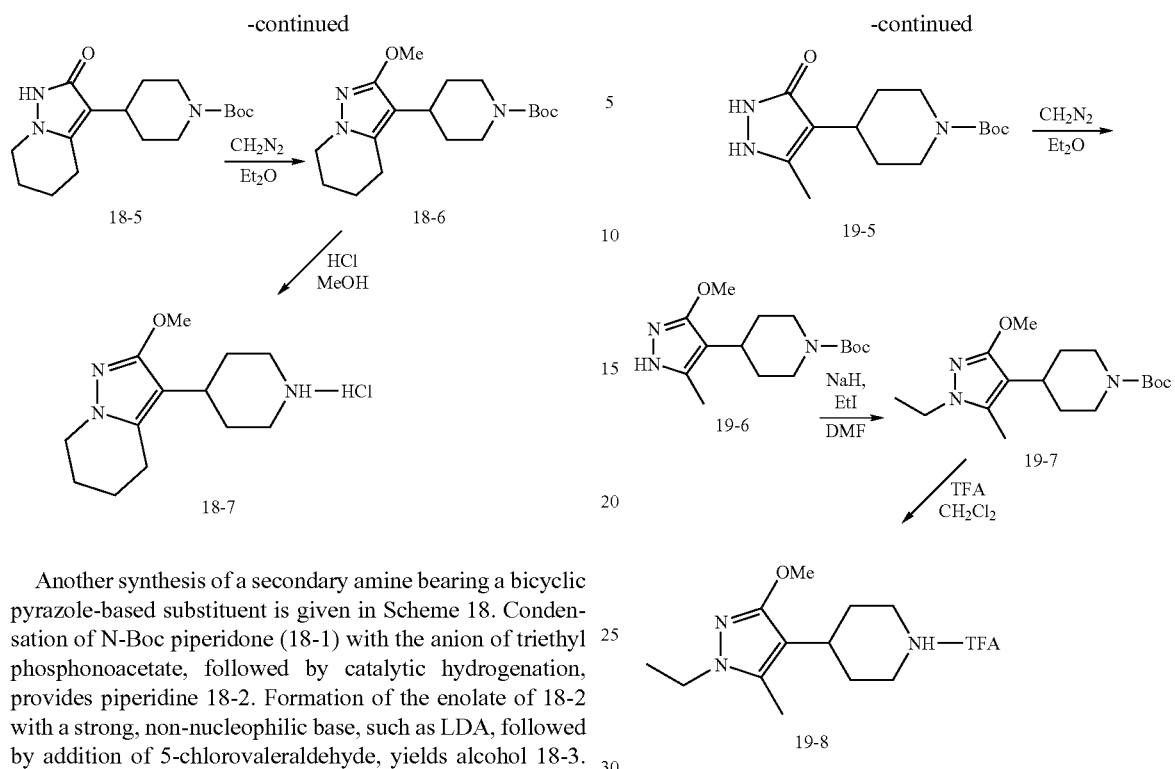

Another synthesis of a secondary amine bearing a bicyclic pyrazole-based substituent is given in Scheme 18. Condensation of N-Boc piperidone (18-1) with the anion of triethyl phosphonoacetate, followed by catalytic hydrogenation, provides piperidine 18-2. Formation of the enolate of 18-2 with a strong, non-nucleophilic base, such as LDA, followed by addition of 5-chlorovaleraldehyde, yields alcohol 18-3. Following Swern oxidation to diketone 18-4, refluxing with hydrazine in xylenes affords bicycle 18-5. Exposure of 18-5 to diazomethane in ether provides methoxy derivative 18-6, which upon deprotection under acidic conditions then affords the desired secondary amine 18-7.

SCHEME 19

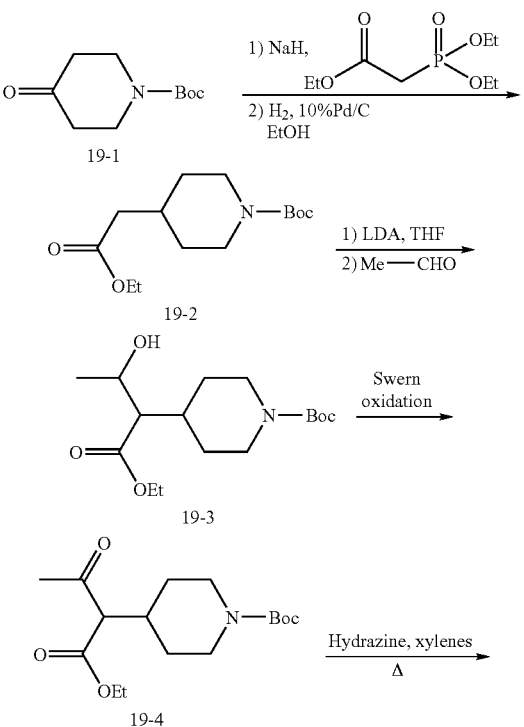

Another synthesis of a secondary amine bearing a monocyclic pyrazole substituent is given in Scheme 19. Condensation of N-Boc piperidone (19-1) with the anion of triethyl phosphonoacetate, followed by catalytic hydrogenation, provides piperidine 19-2. Formation of the enolate of 18-2 with a strong, non-nucleophilic base, such as LDA, followed by addition of acetaldehyde, yields alcohol 19-3. Following Swern oxidation to diketone 19-4, refluxing with hydrazine in xylenes affords pyrazolone 19-5. Exposure of 19-5 to diazomethane in ether provides methoxy derivative 19-6. Alkylation of pyrazole 19-6 by treating with sodium hydride and then ethyl iodide affords fully-substituted pyrazole 19-7. Alternatively, other alkylating agents can be employed in place of ethyl iodide to provide differently substituted pyrazoles. Deprotection with trifluoroacetic acid in methylene chloride then provides secondary amine 19-8.

SCHEME 20

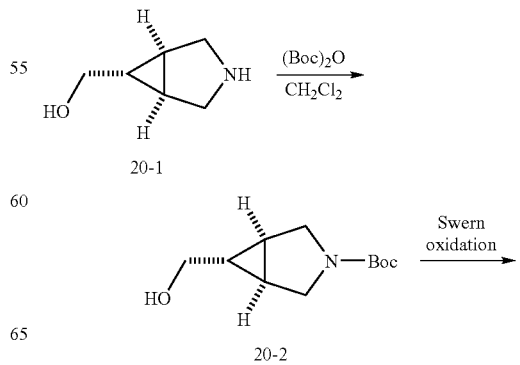

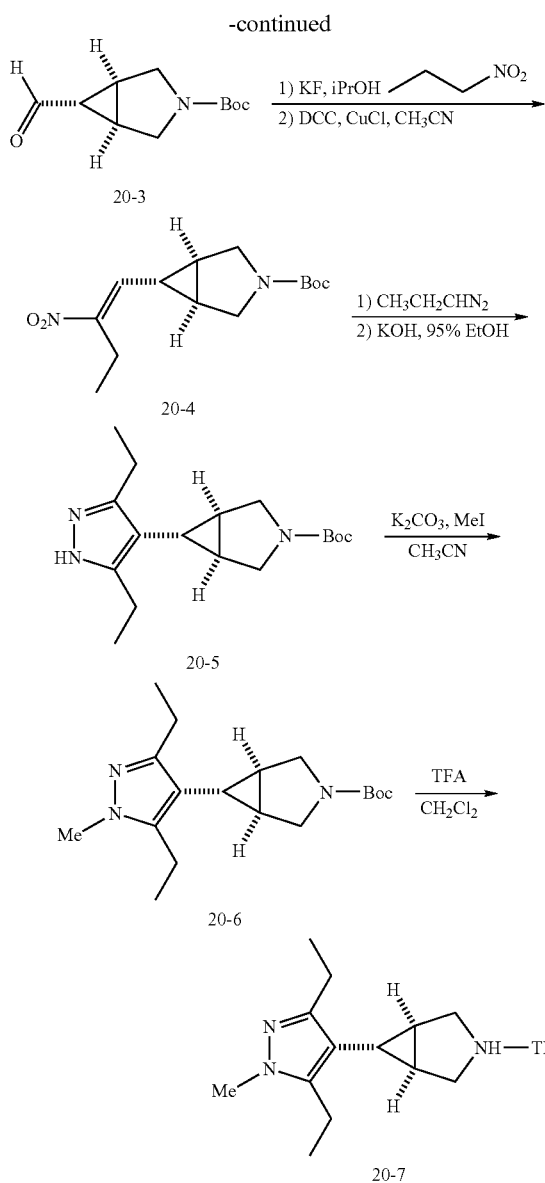

Synthesis of secondary amines with an azabicyclo[3.1.0] hexane ring system is shown in Scheme 20. Treatment of bicycle 20-1 (prepared as described in Brighty, K. E.; Castaldi, M. J. *Synlett* 1996, 1097) with Boc anhydride in methylene chloride affords protected derivative 20-2. Swern oxidation provides aldehyde 20-3, which upon treatment with 1-nitropropane and potassium fluoride in isopropanol, followed by elimination by addition of dicyclohexylcarbodiimide and copper (I) chloride, yields olefin 20-4 as a mixture of geometric isomers. Treatment of this nitro-olefin with diazopropane, followed by treatment with potassium hydroxide in aqueous ethanol, affords the pyrazole 20-5. Alkylation of 20-5 with methyl iodide in the presence of potassium carbonate yields the N-methyl derivative 20-6, which can be deprotected to the desired secondary amine intermediate 20-7 with trifluoroacetic acid in methylene chloride. Other alkylating agents can be used in place of methyl iodide to afford the corresponding N-substituted derivatives. Likewise, other nitromethylalkanes can be employed in place of 1-nitropropane, and alternative diazoalkanes in place of diazopropane can be utilized, to afford the corresponding final products analogous to 20-7.

The following examples serve only to illustrate the invention and its practice. The examples are not to be construed as limitations on the scope or spirit of the invention.

General

Concentration of solutions was carried out on a rotary evaporator under reduced pressure. Conventional flash chromatography was carried out on silica gel (230–400 mesh). Flash chromatography was also carried out using a Biotage Flash Chromatography apparatus (Dyax Corp.) on silica gel (32–63 microns, 60 Å pore size) in pre-packed cartridges of the size noted. NMR spectra were obtained in $CDCl_3$ solution unless otherwise noted. Coupling constants (J) are in hertz (Hz).

HPLC Conditions

LC 1. Retention time using the following conditions: Column: YMC ODS A, 5μ, 4.6×50 mm; Gradient Eluent: 10:90 to 95:5 v/v acetonitrile/water+0.05% TFA over 4.5 min; Detection: PDA, 200–600 nm; Flow Rate: 2.5 mL min.

LC 2. Retention time using the following conditions: Column: YMC Pro-C18, 5μ, 4.6×50 mm; Gradient Eluent: 10:90 to 95:5 v/v acetonitrile/water+0.05% TFA over 3.0 min; Detection: PDA, 200–600 nm; Flow Rate: 2.5 mL/min.

HPLC A. Retention time using the following conditions: Column: YMC ODS A, 5μ, 4.6×50 mm; Gradient Eluent: 10:90 to 90:10 v/v acetonitrile/water+0.05% TFA over 4.5 min, hold 30 sec; Detection: PDA, 210–400 nm; Flow Rate: 2.5 mL/min.

HPLC B. Retention time using the following conditions: Column: Analytical Sales & Services Advantage HL C18 5μ 4.6×100 mm column; Gradient Eluent: 10:90 to 90:10 v/v acetonitrile/water+0.05% TFA over 10 min, hold 2 min; Detection: PDA, 200–400 nm; Flow Rate: 2.25 mL/min.

Aldehyde 1

2-Formyl-2-methyl-propionic acid, para-methoxybenzyl ester

Step A: 2,2-Dimethyl-3-hydroxypropionic acid, para-methoxybenzyl ester

A solution of 1.03 g (8.7 mmol) of 2,2-dimethyl-3-hydroxypropionic acid, 1.8 mL (12.9 mmol), of TEA and 1.3 mL (9.5 mmol) of para-methoxybenzyl chloride in 8 mL of DME was stirred at rt for 24 h. The mixture was partitioned between 200 mL $Et_2O$ and 100 mL of $H_2O$. After separating layers, the organic phase was washed with 100 mL of 1 N $NaHCO_3$, 100 mL of 2 N HCl, 2×100 mL of $H_2O$, 100 mL of brine, dried over $MgSO_4$ and concentrated. The residue was purified by flash chromatography using a gradient of 3:1 v/v to 3:2 v/v of hexanes/EtOAc as the eluant to afford the title compound: $R_F$: 0.17 (4:1 v/v hexanes/EtOAc); $^1$H-NMR (500 MHz) δ 1.21 (s, 6H), 3.57 (s, 2H), 3.82 (s, 3H), 5.09 (s, 2H), 6.90 (d, J=8.8, 2H), 7.28 (d, J=8.8, 2H).

Step B: 2-Formyl-2-methyl-propionic acid, para-methoxybenzyl ester

A solution of 0.2 mL (2.2 mmol) of oxalyl chloride in 4 mL of $CH_2Cl_2$ at −78° C. was treated with 0.32 mL (4.5 mmol) of DMSO in 0.5 mL of $CH_2Cl_2$ maintaining the temperature at less than 60° C. The resulting mixture was stirred cold for 5 min. A solution of 211 mg (0.94 mmol) of 2,2-dimethyl-3-hydroxypropionic acid, para-methoxybenzyl ester (from Step A) in 1 mL of $CH_2Cl_2$ was added maintaining the temperature at less than −60° C. The resulting mixture was stirred cold for 15 min. The mixture was treated with 1.6 mL (9.1 mmol) of DIEA maintaining the temperature at less than −60° C. The reaction was warmed to 0° C., stirred for 30 min and quenched with $H_2O$. The mixture was partitioned between 50 mL of $CH_2Cl_2$ and 50 mL of H2O and the layers were separated. The aqueous layer was extracted with 50 mL of $CH_1Cl_2$. The combined organic phases were washed with 100 mL of brine, dried over $Na_2SO_4$ and concentrated to afford the title compound which was used without further purification: $R_F$: 0.43 (4:1 v/v hexanes/EtOAc); $^1$H-NMR (500 MHz) δ 1.35 (s, 6H), 3.81 (s, 3H), 5.12 (s, 2H), 6.89 (d, J=8.7, 2H), 7.27 (d, J=8.7, 2H), 9.66 (s, 1H).

Aldehyde 2

2-Formyl-2-methyl-propionic acid, benzyl ester

The title compound was prepared using procedures analogous to those described to prepare Aldehyde 1, except that benzyl bromide was substituted for para-methoxybenzyl chloride in Step A. $^1$H-NMR (500 MHz) δ 1.38 (s, 6H), 5.20 (s, 2H), 7.27–7.40 (m, 5H), 9.69 (s, 1H).

Aldehyde 3

2-Ethyl-2-formyl-butyric acid, benzyl ester

Step A: Diethylmalonic acid, dibenzyl ester

A solution of 2 mL (7.9 mmol) of dibenzyl malonate, 2 mL (25.0 mmol) of iodoethane and 7.84 g (24.0 mmol) of cesium carbonate in 50 mL of DMF was stirred overnight at rt. The reaction was partitioned between 250 mL of $Et_2O$ and 250 mL of brine. After separating phases, the organic layer was washed with 250 mL of brine, dried over $MgSO_4$ and concentrated to afford the title compound, which was used without further purification. $R_F$: 0.47 (9:1 v/v hexanes/EtOAc); $^1$H-NMR (500 MHz) δ 0.80 (t, J=7.5, 6H), 1.99 (q, J=7.5, 4H), 5.13 (s, 4H), 7.27–7.33 (m, 10H).

Step B: 2-Ethyl, 2-formyl-butyric acid, benzyl ester

A solution of dibenzyl diethylmalonate (7.9 mmol, from Step A) in $CH_2Cl_2$ at −78° C. was treated with 16 mL (16.0 mmol) of 1 M DIBAL in $CH_2Cl_2$ maintaining the temperature at less than −65° C. (J. Organic Chemistry, 1993, 58, 6843–6850). After stirring for 2.75 h, the reaction was quenched cold with 8 mL of saturated $NH_4Cl$ and 10 mL of 2 N HCl. The reaction was warmed to rt and partitioned between 200 mL of $CH_2Cl_2$ and 300 mL of saturated Rochelle salts. After separating phases, the aqueous layer was extracted with 200 mL $CH_2Cl_2$. The combined organics were dried over $MgSO_4$ and concentrated. The residue was purified by flash chromatography using 9:1 v/v of hexanes/EtOAc as the eluant to afford the title compound as a colorless oil, which contained 15% starting material: $R_F$: 0.44 (9:1 v/v hexanes/EtOAc); $^1$H-NMR (500 MHz) δ 0.83 (t, J=7.5, 6H), 1.82–1.95 (m, 4H), 5.23 (s, 2H), 7.27–7.39 (m, 5H), 9.85 (s, 1H).

Aldehyde 4

1-Formyl-cyclohexane carboxylic acid, benzyl ester

The title compound was prepared using procedures analogous to those described to prepare Aldehyde 3, except that 1,5-dibromopentane was substituted for iodoethane in Step A. $^1$H-NMR (500 MHz) δ 1.43–1.55 (m, 6H), 1.88–1.93 (m, 2H), 2.02–2.07 (m, 2H), 5.19 (s, 4H), 7.27–7.39 (m, 5H), 9.55 (s, 1H).

Aldehyde 5

1-Formyl-cyclobutane carboxylic acid, benzyl ester

Step A: 1,1-Cyclobutanedicarboxylic acid, dibenzyl ester

A solution of 2.0 g (13.8 mmol) of cyclobutanedicarboxylic acid in 20 mL of DMF at 0° C. was treated with 7.7 mL (55.5 mmol) of triethylamine and 5.0 mL (41.6 mmol) of benzyl bromide. The reaction was warmed to rt and stirred overnight. The reaction was partitioned between $H_2O$ and $CH_2Cl_2$. The residue was purified with a 40M Biotage column using 1:1 v/v of hexanes/EtOAc as the eluant to afford the title compound: $^1$H-NMR (500 MHz) δ 1.95–2.03 (m, 2H), 2.55–2.58 (m, 4H), 5.14 (s, 4H), 7.24–7.37 (m, 10H).

Step B: 1-Formyl-cyclobutane carboxylic acid, benzyl ester

The title compound was prepared from 1,1-cyclobutanedicarboxylic acid, dibenzyl ester (from Step A) using a procedure analogous to that described for Aldehyde 3, Step B. $^1$H-NMR (500 MHz) δ 1.90–2.05 (m, 2H), 2.47–2.50 (m, 4H), 5.21 (s, 2H), 7.25–7.39 (m, 5H), 9.79 (s, 1H).

Aldehyde 6

1-Formyl-cyclopentane carboxylic acid, benzyl ester

The title compound was prepared using procedures analogous to those described to prepare Aldehyde 3, except that 1,4-dibromobutane and potassium carbonate were substituted for iodoethane and cesium carbonate in Step A. $^1$H-NMR (500 MHz) δ 1.55–1.76 (m, 4H), 1.98–2.23 (m, 4H), 5.19 (s, 2H), 7.23–7.38 (m, 5H), 9.67 (s, 1H).

Aldehyde 7

4-(4-Formyl-tetrahydropyranyl)-carboxylic acid, benzyl ester

The title compound was prepared using procedures analogous to those described to prepare Aldehyde 8, except that 2-chloroethyl ether was substituted for 1,4-dibromobutane. $^1$H-NMR (500 MHz) δ 1.99–2.04 (m, 2H), 2.12–2.17 (m, 2H), 3.61–3.68 (m, 4H), 5.21 (s, 2H), 7.25–7.39 (m, 5H), 9.56 (s, 1H).

Aldehyde 8

3-(3-Formyl-bicyclo[3.1.0]hexane)-exo-carboxylic acid, benzyl ester and

Aldehyde 9

3-(3-Formyl-bicyclo[3.1.0]hexane)-endo-carboxylic acid, benzyl ester

Step A: 1,1-(Cyclopent-3-ene)-dicarboxylic acid, dibenzyl ester

A solution of 4.3 mL (17.1 mmol) of dibenzyl malonate in 20 mL of DMF at 0° C. was treated with 0.36 g (43 mmol) of LiH. After two hours at 0° C., 2 mL (19 mmol) of cis-1,4-dichloro-2-butene was added (J. Org. Chem. 1984, 49, 928–931). The reaction was warmed to rt and stirred for 3.5 days. The reaction was partitioned between 200 mL of 1:1 v/v hexane/Et$_2$O and 200 mL of H$_2$O. After separating phases, the organic layer was washed with 200 mL H$_2$O, dried over MgSO$_4$ and concentrated. The residue was purified with a 40M Biotage column using 13:7 v/v of hexanes/CH$_2$Cl$_2$ and 11:9 v/v of hexanes/CH$_2$Cl$_2$ as the eluant to afford the title compound as a white solid: R$_F$: 0.25 (3:2 v/v hexanes/CH$_2$Cl$_2$); $^1$H-NMR (500 MHz) δ 3.07 (s, 4H), 5.15 (s, 4H), 5.63 (s, 2H), 7.25–7.34 (m, 10H).

Step B: 3,3-Bicyclo[3.1.0]hexane dicarboxylic acid, dibenzyl ester

A solution of 8.8 mL (8.8 mmol) of 1.0 M diethyl zinc in hexane at −10° C. in 8 mL of CH$_2$Cl$_2$ and 0.92 mL (8.8 mmol) of ethylene glycol dimethyl ether was treated with 1.4 mL (17.6 mmol) of diiodomethane dropwise maintaining an internal temperature≦−9° C. (J. Organic Chemistry 1995, 60, 1081–1083). After stirring for 15 minutes, 1.0 g (2.9 mmol) of 1,1-(cyclopent-3-ene)-dicarboxylic acid, dibenzyl ester (from Step A) was added. The reaction was warmed to reflux for 24 hours. After cooling to rt, the reaction was partitioned between 200 mL of Et$_2$O and 200 mL of NH$_4$Cl. After separating phases, the organic layer was washed with 200 mL 10% Na$_2$S$_2$O$_3$, dried over MgSO$_4$ and concentrated. The residue was purified with a 40M Biotage column using 24:1 v/v of hexanes/MTBE as the eluant to afford the title compound as a colorless oil and a mixture of product and starting material: R$_F$: 0.26 (19:1 v/v of hexanes/MTBE); $^1$H-NMR (500 MHz) δ −0.01 (m, 1H), 0.41 (m, 1H), 1.34–1.37 (m, 2H), 2.45–2.48 (m, 2H), 2.58–2.61 (m, 2H), 5.08 (s, 2H), 5.10 (s, 2H), 7.23–7.33 (m, 10H).

Step C: 3-(3-Formyl-bicyclo[3.1.0]hexane)-exo-carboxylic acid, benzyl ester and 3-(3-Formyl-bicyclo[3.1.0]hexane)-endo-carboxylic acid, benzyl ester The title compounds were prepared as a separable mixture (1:5 exo:endo) from 3,3-bicyclo[3.1.0]hexane dicarboxylic acid, dibenzyl ester (from Step B) using a procedure analogous to that described for Aldehyde 3, Step B. Aldehyde 10: 3-(3-formyl-bicyclo[3.1.0]hexane)-exo-carboxylic acid, benzyl ester R$_F$: 0.37 (9:1 v/v hexanes/Et$_2$O); $^1$H-NMR (500 MHz) δ −0.18 (m, 1H), 0.38 (m, 1H), 1.35–1.39 (m, 2H), 2.41–2.45 (m, 2H), 2.54–2.57 (m, 2H),5.15 (s, 2H), 7.27–7.39 (m, 5H), 9.55 (s, 1H). Aldehyde 11: 3-(3-formyl-bicyclo[3.1.0]hexane)-endo-carboxylic acid, benzyl ester R$_F$: 0.29 (9:1 v/v hexanes/Et$_2$O); $^1$H-NMR (500 MHz) δ 0.01 (m, 1H), 0.48 (m, 1H), 1.39–1.44 (m, 2H), 2.26–2.32 (m, 2H), 2.47–2.52 (m, 2H), 5.19 (s, 2H), 7.27–7.40 (m, 5H), 9.44 (s, 1H).

Aldehyde 10

(2R or 2S)-2-Formyl-2-methyl-butyric acid, benzyl ester and

Aldehyde 11

(2S or 2R)-2-Formyl-2-methyl-butyric acid, benzyl ester

Step A: Ethylmalonic acid, dibenzyl ester

A solution of 2.0 g (15 mmol) of ethyl-malonic acid, 4.7 mL (31 mmol) of 1,8-diazabicyclo[5.4.0]undec-7-ene (DBU) and 3.9 mL (32 mmol) of benzyl bromide in 100 mL of benzene was refluxed for 22 hours. After cooling, the reaction was washed with 150 mL of H$_2$O. After separating layers, the organic phase was dried over MgSO$_4$ and concentrated. The residue was purified on a 40M Biotage column using 24:1 v/v hexane/EtOAc as the eluant to afford the title compound as a colorless oil: R$_F$: 0.40 (9:1 v/v hexane/EtOAc); $^1$H-NMR (500 MHz) δ 0.97 (t, J=7.4, 3H), 1.99 (quint, J=7.4, 2H), 3.39 (t, J=7.4, 1H), 5.17 (s, 2H), 7.29–7.36 (m, 10H).

Step B: 2-Formyl-butyric acid, benzyl ester

The title compound was prepared from ethylmalonic acid, dibenzyl ester (from Step A) using a procedure analogous to that described for Aldehyde 3, Step B. R$_F$: 0.35 (9:1 v/v hexane/EtOAc); $^1$H-NMR (500 MHz: Equilibrium mixture of aldehyde and enol) δ 0.92–1.00 (m), 1.04–1.08 (m), 1.93–2.01 (m), 2.14–2.18 (m), 5.17, 5.23, 5.26 (3s), 7.05 (d, J=12.6), 7.30–7.41 (m), 9.74 (d, J=2.3), 11.33 (d, J=12.6).

Step C: 2-((E)-{[(2S)-2-(Methoxymethyl)-1-pyrrolidinyl]imino}methyl)butyric acid, benzyl ester A suspension of 395 mg (1.9 mmol) of 2-formyl-butyric acid, benzyl ester (from Step B), 0.26 mL (1.9 mmol) of (S)-(−)-1-amino-2-methoxymethyl)pyrrolidine (S-AMP) and 0.24 g of 4A molecular sieves in 4 mL of CH$_2$Cl$_2$ was stirred at room temperature for 16 hours. The reaction was filtered and concentrated. The residue was purified on a 40M Biotage column using 9:1 v/v hexane/EtOAc as the eluant to afford the title compound as a colorless oil: R$_F$: 0.23 (9:1 v/v hexane/EtOAc); $^1$H-NMR (500 MHz: Mixture of diastereomers) δ 0.90–0.95 (m, 3H), 1.64–1.99 (m, 6H), 2.79 (m, 1H), 3.19–3.57 (m, 8E), 5.13–5.19 (m, 2H), 6.53 (m, 1H), 7.30–7.38 (m, 5H).

Step D: (2R or 2S)-((E)-{[(2S)-2-(Methoxymethyl)-1-pyrrolidinyl]imino}methyl)-2-methyl-butyric acid, benzyl ester and (2S or 2R)-((E)-{[(2S)-2-(Methoxymethyl)-1-pyrrolidinyl]imino}methyl)-2-methyl-butyric acid, benzyl ester A solution of 98 mg (0.3 mmol) of 2-((E)-{[(2S)-2-(methoxymethyl)-1-pyrrolidinyl]imino}methyl)butyric acid, benzyl ester (from Step C) in 1 mL of THF was added to a solution of 1.4 mL (0.35 mmol) of 0.25 M LDA at −78° C. After 20 min 0.023 mL (0.36 mmol) of methyl iodide was added. The reaction was allowed to warm to room temperature overnight. The reaction was poured into 25 mL of H$_2$O and extracted with 3×50 mL of Et$_2$O. The combined organics were dried over Na$_2$SO$_4$ and concentrated. Diastereomers were separated using preparative HPLC Chiralcel OD (Analytical Column: Chiralcel OD; Mobile Phase: 96:4 v/v hexane/isopropanol; 2 mg/mL; 0.02 mL/injection; Flow: 0.5 mL/min; 220 nm; Retention Times: 10.7 and 12.4 min). Diastereomer 1: $^1$H-NMR (500 MHz) δ 0.86 (t, J=7.4, 3H), 1.35 (s, 3H), 1.69–1.99 (m, 6H), 2.75 (m, 1H), 3.29–3.59 (m, 7H), 5.16 (ABq, J=12.5, 2H), 6.67 (s, 1H), 7.30–7.38 (m, 5H); Diastereomer 2: $^1$H-NMR (500 MHz) δ 0.85 (t, J=7.4, 3H), 1.35 (s, 3H), 1.70–1.99 (m, 6H), 2.75 (m, 1H), 3.30–3.59 (m, 7H), 5.14 (ABq, J=12.6, 2H), 6.67 (s, 1H), 7.30–7.39 (m, 5H).

Step E: (2R or 2S)-2-Formyl-2-methyl-butyric acid, benzyl ester and (2S or 2R)-2-Formyl-2-methyl-butyric acid, benzyl ester The diastereomers from Step D were separately treated in CH$_2$Cl$_2$ with ozone at −78° C., followed by treatment with dimethylsulfide. The residue was purified by flash chromatography using 92:8 v/v hexane/EtOAc as the eluant to afford the title compounds as a colorless oil: $^1$H-NMR (500 MHz) δ 0.88 (t, J=12.4, 3H), 1.32 (s, 3H), 1.80 (m, 1H), 1.97 (m, 1H), 5.21 (s, 2H), 7.33–7.40 (m, 5H), 9.74 (s, 1H).

Aldehyde 12

(2R or 2S)-2-Formyl-2-methyl-4,4,4-trifluorobutyric acid, benzyl ester and

Aldehyde 13

(2S or 2R)-2-Formyl-2-methyl-4,4,4-trifluorobutyric acid, benzyl ester

The title compounds were prepared from (R/S)-2-formyl-2-methyl-4,4,4-trifluorobutyric acid, benzyl ester using procedures analogous to that described for Aldehydes 10 and 11, except (R)-(+)-1-amino-2-methoxymethyl)pyrrolidine (R-AMP) was substituted for (S)-(−)-1-amino-2-methoxymethyl)pyrrolidine (S-AMP) in Step C. $^1$H-NMR (500 MHz) δ 1.51 (s, 3H), 2.68–2.88 (m, 2H), 5.22 (s, 2H), 7.33–7.41 (m, 5H), 9.64 (s, 1H).

Aldehyde 14

1-Formyl-cyclopropane carboxylic acid, benzyl ester

The title compound was prepared from 1,1-cyclopropanedicarboxylic acid using procedures analogous to that described for Aldehydes 10 and 11 (Steps A and B). $^1$H-NMR (500 MHz) δ 1.63–1.73 (m, 4H), 5.27 (s, 2H), 7.35–7.42 (m, 5H), 10.43 (s, 1H).

The following are representative Procedures for the preparation of the piperidines used in the following Examples or which can be substituted for the piperidines used in the following Examples and which are not commercially available.

Piperidine 1

4-(Imidazo[1,2-a]pyridin-3-yl)piperidine di-TFA salt

Step A: 1-tert-Butoxycarbonyl-4-(2-hydroxyethyl)piperidine

A mixture of 4-(2-hydroxyethyl) piperidine (5.0 g, 40 mmol), di-t-butyl dicarbonate (10.9 g, 50 mmol), and triethylamine (7 mL, 50 mmol) in 100 mL of anhydrous methylene chloride was stirred overnight at room temperature. Volatiles were removed in vacuo and the resulting oil was purified on a silica gel column using 20% ethyl acetate in hexane as eluent to give the desired product as a colorless oil.

Step B: 1-tert-Butoxycarbonyl-4-(formylmethyl)piperidine

Oxalyl chloride (2.2 mL, 25 mmol) was added to 75 mL of anhydrous methylene chloride at −78° C. DMSO (3.5 mL, 50 mmol) was then added dropwise over 5 min, and the resulting mixture was stirred for 15 min. 1-tert-butoxycarbonyl-4-(2-hydroxyethyl)piperidine (2.29 g, 10 mmol, from Step A) was dissolved in 5 mL of anhydrous methylene chloride and added over 10 min to the above mixture. After stirring 30 min, DIEA (17.4 mL, 100 mmol) was added over 10 min. The mixture was then warmed to 0° C. and maintained at that temperature for 1 h. After quenching with water, the reaction mixture was diluted with 75 mL of methylene chloride and the layers were separated. The organic phase was washed with 3×50 mL of water and dried over anhydrous magnesium sulfate. Solvent removal gave an oil, which was purified on silica gel using 20% ethyl acetate in hexane to give the desired aldehyde which hardened overnight into an oily solid.

NMR: (CDCl$_3$) δ 2.15 (2H, d, J=3); 9.8 (1H,s); 1.2, 1.5, 1.7, 2.75, 4.1(all multiplets)

Step C: 1-tert-Butoxycarbonyl-4-(1-bromo-formylmethyl)piperidine

A mixture of 1-tert-butoxycarbonyl-4-(formylmethyl)piperidine (0.57 g, 2.25 mmol, step B), 3,3-dibromo-Meldrum's acid (0.75 g, 2.5 mmol) in 10 mL of anhydrous ether was stirred for 2 days at room temperature under nitrogen. The reaction mixture was diluted with ethyl acetate and washed with sat'd. sodium bicarbonate solution. The organic phase was dried over anhydrous magnesium sulfate. Solvent removal and purification on silica gel using 20% ethyl acetate in hexane as solvent gave the pure bromo aldehyde as a colorless oil.

$^1$H NMR: (CDCl$_3$) δ: 4.04 (1H,dd; J=1.5;2); 9.46 (1H,d; J=1.5) 1.35, 1.7, 1.95, 2.1, 2.75, 4.2 (all multiplets)

Step D: 1-(tert-Butoxycarbonyl)-4-(imidazo[1.2-a]pyridin-3-yl)piperidine

To a solution of 1.15 g of 1-tert-butoxycarbonyl-4-(1-bromo-formylmethyl)piperidine (from Step C) in 15 mL ethanol was added 388 mg of 2-aminopyridine. After refluxing for 18 h, the solvent was evaporated. The mixture was partitioned between ethyl acetate and saturated sodium bicarbonate solution. Aqueous layer was extracted with ethyl acetate (3×). The combined organic phase was washed with brine, dried over magnesium sulfate and concentrated. The residue was purified by flash chromatography with 50% ethyl acetate in hexanes, followed by 100% ethyl acetate to give the title compound as a solid. $^1$H NMR (500 MHz, CDCl3) δ 1.48 (s, 9H), 1.70 (m, 2H), 2.06 (d, J=13 Hz, 2H), 2.93–3.02 (m, 3H), 4.26 (br, 2H), 6.87 (t, J=6.8 Hz, 1H). 7.21(m, 1H), 7.44(s, 1H), 7.69(d, J=9.2 Hz,1H), 7.99 (d, J=6.9 Hz, 1H).

Step E: 4-Imidazo[1,2-a]pyridin-3-yl)piperidine di-TFA salt

To 100 mg of 1-(tert-butoxycarbonyl)-4-(imidazo[1,2-a]pyridin-3-yl)piperidine from Step D was added 2 mL TFA. The reaction was stirred at rt for 1 h. The mixture was concentrated to afford a viscous oil.

Piperidine 2

4-(7-tert-butylimidazo[1,2-a]pyridin-3-yl)piperidine, TFA salt

Step A: 2-Amino-4-tert-butylpyridine

To 790 mg of sodium amide were added 20 mL of N,N-dimethylaniline and 2.74 g of 4-tert-butyl pyridine at it. The mixture was stirred at 150° C. for 6 h. During this period, 3 more portions of sodium amide (790 mg each) were added. The reaction was cooled down to rt. The mixture was partitioned between ethyl acetate and water. Aqueous layer was extracted with ethyl acetate (3×). The combined organic phase was washed with brine, dried over magnesium sulfate and concentrated. The residue was purified by flash chromatography with 50% ethyl acetate in hexanes followed by 100% ethyl acetate to give the title compound as a solid:

$^1$H NMR (500 MHz, CDCl$_3$) δ 1.21 (s, 9H), 6.44 (t, 1H), 6.6.62 (dd, J=5.5 Hz and, 1H), 7.94 (d, J=5.5 Hz, 1H).

Step B: 1-(tert-Butoxycarbonyl)-4-(7-tert-butylimidazo[1,2-a]pyridin-3-yl)piperidine The title compound was prepared from 470 mg of 1-t-butyloxycarbonyl-4-(1-bromo-formylmethyl)piperidine (from Piperidine 1, Step C) and 277 mg of 2-amino-4-tert-butyl pyridine (from Step A) in 12 mL ethanol using a procedure analogous to that described in Piperidine 1, Step D to provide the title compound as a solid.

Step C: 4-(7-tert-Butylimidazo[1,2-a]pyridin-3-yl)piperidine, TFA salt

The title compound was prepared from 35 mg of 1-(tert-butoxycarbonyl)-4-((7-tert-butyl)imidazo[1,2-a]pyridin-3-yl)piperidine (from Step B) in 2 mL of TFA, using a procedure analogous to that described in Piperidine 1, Step E to provide the title compound as a viscous oil.

Piperidine 3

4-(2-Ethyl-5,6,7,8-tetrahydroimidazo[1,2-a]pyridin-3-yl)piperidine, acetic acid salt Step A: 2-Ethyl-imidazo[1,2-a]pyridine The title compound was prepared from 2-aminopyridine and 1-bromo-2-butanone, employing procedures analogous to those described for Piperidine 1. $^1$H NMR (500 MHz, CDCl3) δ 1.34 (t, J=7.3 Hz, 3H), 2.82 (q, J=7.6 Hz, 2H), 6.70 (t, J=6.6 Hz, 1H), 7.10 (m, 1H), 7.32 (s, 3H), 7.51 (d, J=8.9 Hz, 1H), 8.03 (dd, J=6.6, 0.9 Hz, 1H).

Step B: 3-Bromo-2-ethyl-imidazo[1,2-a]pyridine

To a solution of 2-ethyl-imidazo[1,2-a]pyridine (2.17 g, 14.9 mmol) in ethanol (25 mL) was added bromine (2.0 g, 12.5 mmol) in water (5 mL) dropwise at rt. After stirring at rt for 4 h, ethanol was evaporated under reduced pressure. The residue was basified with aqueous sodium bicarbonate and extracted with methylene chloride (3×). The organic phase was washed with brine and dried over anhydrous magnesium sulfate. Concentration followed by flash chromatography eluting with 20% ethyl acetate in hexanes, followed by 50% ethyl acetate in hexanes afforded the title compound as a viscous oil. $^1$H NMR (500 MHz, CDCl3) δ 1.36 (t, J=7.5 Hz, 3H), 2.83 (q, J=7.6 Hz, 2H), 6.88 (t, J=6.8 Hz, 1H), 7.20 (m, 1H), 7.55 (dd, J=8.9, 0.9 Hz, 1H), 8.05 (dd, J=6.9, 1.2 Hz, 1H).

Step C: 2-Ethyl-3-(4-pyridyl)-imidazo[1,2-a]pyridine

To a solution of 3-bromo-2-ethyl-imidazo[1,2-a]pyridine (1.4 g, 6.28 mmol), 4-tributylstannylpyridine (2.31 g, 6.28 mmol) and Pd (II) (Ph$_3$P)$_2$Cl$_2$ (442 mg, 0.63 mmol) in toluene (5 mL) was added lithium chloride (26.7 mg, 0.63). After refluxing for 18 h, the mixture was partitioned between ethyl acetate and aqueous sodium bicarbonate. The aqueous layer was extracted with ethyl acetate (3×). Combined organic phase was washed with brine and dried over anhydrous magnesium sulfate. Concentration followed by flash chromatography eluting with 100% ethyl acetate, then 10% methanol in methylene chloride afforded the title compound as a viscous oil. $^1$H NMR (500 MHz, CDCl3) δ 1.36 (t, J=7.5 Hz, 3H), 2.84 (q, J=7.5 Hz, 2H), 6.68 (dt, J=6.8, 1.1 Hz, 1H), 7.21 (m, 1H), 7.39 (dd, J=5.9, 1.6 Hz, 2H), 7.61 (dd, J=8.9, 1.0 Hz, 1H), 8.75 (d, J=5.9 Hz, 2H).

Step D: 4-(2-Ethyl-5,6,7,8-tetrahydroimidazo[1,2-a]pyridin-3-yl)piperidine, acetic acid salt A solution of 2-ethyl-3-(4-pyridyl)-imidazo[1,2-a]pyridine (700 mg, 3.13 mmol) in ethanol (12 mL) and acetic acid (4 mL) was hydrogenated using Platinum (IV) oxide (40 mg) under 40 psi of H$_2$ gas in a Parr shaker at rt for 18 h. The mixture was filtered through celite and concentrated to give the title compound as a viscous oil.

Piperidine 4

4-(2-Ethyl-4,5,6,7-tetrahydro-(2H)-indazol-3-yl)piperidine

To a suspension of 1.60 g 60% sodium hydride in 10 mL dry THF was added a solution of 1.963 g (20 mmole) cyclohexanone and 9.893 g (40 mmole) of 1-benzylpiperidine-4-carboxylic acid ethyl ester in 30 mL THF. This mixture was heated to reflux over night. Work-up followed by silica gel FC (15~50% ethyl acetate in hexanes with 1% triethylamine) provided a product containing about 5.7:1 molar ratio of starting 1-benzylpiperidine-4-carboxylic acid ethyl ester and title compound.

ESI-MS 300.3 (M+H), HPLC A: 2.90 and 3.57 min. (for tautomeric forms).

Step B: 4-(2-Ethyl-4,5,6,7-tetrahydro-(2H)-indazol-3-yl)-1-benzylpiperidine

The title compound was prepared from the semi-crude (1-benzylpiperidin-4-yl)-(cyclohexanon-2-yl)ketone from step A and 34% aqueous ethylhydrazine in 4:1 acetonitrile and water at rt. This provided 8:1 ratio of isomeric ethyl pyrazoles in favor of the title compound. (Note: Use of ethyl hydrazine oxalate in the presence of DIEA gave about 2:1 ratio of the same isomers.) The 1-benzylpiperidine-4-carboxylic acid ethyl ester present in the starting β-diketone was removed after saponification of the crude product with sodium hydroxide in water ethanol mixture followed by extractive work-up. The desired ethyl isomer is the higher R$_f$ isomer. It was isolated on silica gel chromatography (60~100% ethyl acetate in hexanes and 5~20% methanol in ethyl acetate, both with 1% triethylamine).

$^1$H NMR (500 MHz) δ 7.33~7.36 (m, 4H), 7.26~7.30 (m, 1H), 4.07 (q, 7.2 Hz, 2H), 3.57 (s, 2H), 3.00~3.03 (m, 2H), 2.64~2.66 (m, 2H), 2.60~2.63 (m, 2H), 2.57~2.63 (m, 1H), 1.96~2.08 (m, 4H), 1.69~1.81 (m, 6H), 1.39 (t, 7.2 Hz, 3H). The identity of the title compound was confirmed by NOE difference spectroscopy.

Step C: 4-(2-Ethyl-4,5,6,7-tetrahydro-(2H)-indazol-3-yl)piperidine

A mixture of 0.273 g 4-(2-ethyl-4,5,6,7-tetrahydro-(2H)-indazol-3-yl)-1-benzylpiperidine from Step B above, 0.789 g ammonium formate, and 35 mg 20% Pd(OH)$_2$ in 6 mL methanol was heated at 65° C. for 1 h. Basic aqueous work-up with ether extraction provided the title compound as a colorless solid.

$^1$H NMR (500 MHz) δ 4.08 (q, 7.2 Hz, 2H), 3.19 (br d, 11.9 Hz, 2H), 2.71~2.77 (m, 1H), 2.68~2.74 (m, 2H), 2.64~2.66 (m, 2H), 2.60~2.62 (m, 2H), 1.82~1.91 (m, 2H), 1.71~1.80 (m, 6H), 1.40 (t, 7.2 Hz, 3H). The identity of the title compound was confirmed again by NOE difference spectroscopy.

Piperidine 5

4-(7-Chloroimidazo[1,2-a]pyridin-3-yl)piperidine, TFA salt

The title compound was prepared from 350 mg of 1-(tert-butoxycarbonyl)4-(1-bromo-2-oxoethyl)piperidine (from Piperidine 1, Step C) and 162 mg of 2-amino-4-chloropyridine (prepared using procedures analogous to those described by R. J. Sundberg et al, *Org. Preparations & Procedures Int.* 1997, 29, (1), 117–122) in 10 mL ethanol using a procedure analogous to that described in Piperidine 1, Step D to provide the BOC intermediate as a solid prior to the cleavage of the Boc-group to give the title TFA salt.

Piperidine 6

4-(7-n-Propylimidazo[1,2-a]pyridin-3-yl)piperidine, TFA salt

The title compound was prepared according to the general procedures of Piperidines 1 and 2, employing 2-amino-4-n-propylpyridine (prepared using a procedure analogous to that described in Piperidine 2, Step A) in place of 2-aminopyridine in Piperidine 1, Step D.

Piperidine 7

4-(2-Ethylindazol-3-yl)piperidine, TFA salt

Step A: 2-Ethylindazole

To a solution of indazole (6.2 g, 52.5 mmol) in DMF (30 mL) was added sodium hydride (60% dispersion in mineral oil, 3.0 g, 75.0 mmol) at 0° C. After stirring at 0° C. for 20 min., ethyl iodide (5 mL, 62.5 mmol) was added dropwise at 0° C. The mixture was stirred at rt for 1 h, and then partitioned between ethyl acetate and water. The aqueous layer was extracted with ethyl acetate (3×). The combined organic phases were washed with brine, and dried over anhydrous magnesium sulfate. TLC indicated that a 2:1 mixture of two isomers was formed. The mixture was purified by flash chromatography (hexanes:ethyl acetate=4:1, then 1:1) to give the title compound as a viscous oil (slow moving isomer).

Step B: 2-Ethyl-3-bromoindazole

To a solution of 2-ethylindazole (2.32 g, 15.87 mmol) in ethanol (20 mL) was added bromine (2.54 g, 15.87 mmol) in ethanol (1 mL)/water (1 mL) at 0° C. After stirring at 0° C. for 10 min. and at rt for 1 h, the reaction was quenched with aq. sodium bicarbonate. The mixture was partitioned between ethyl acetate and aq. sodium bicarbonate. The aqueous layer was extracted with ethyl acetate (3×). The combined organic phase was washed with brine, and dried over anhydrous magnesium sulfate. Purification by flash chromatography (hexanes:ethyl acetate=1:1, then 100% ethyl acetate) gave the title compound as a viscous oil.

Step C: 1-(tert-Butoxycarbonyl)-4-hydroxy-4-(2-ethyl-indazol-3-yl)piperidine

To a solution of 2-ethyl-3-bromoindazole (3.4 g, 15.18 mmol) in THF (30 mL) was added t-BuLi (1.7 M in pentane, 10.72 mL, 18.22 mmol) dropwise at −78° C. After stirring at −78° C. for 20 min., was added tert-butyl 4-oxo-1-piperidinecarboxylate (3.03 g, 15.18 mmol) in THF (10 mL) dropwise at −78° C. The mixture was stirred at −78° C. for 10 min. and at rt for 18 h. After the reaction was quenched with aq. NH$_4$Cl, the mixture was partitioned between ethyl acetate and water. The aqueous layer was extracted with ethyl acetate (3×). The combined organic phases were washed with brine, and dried over anhydrous magnesium sulfate. Concentration followed by purification by flash chromatography (hexanes:ethyl acetate=4:1, then 1:1) to give the title compound as a foamy solid.

Step D: 1-(tert-Butoxycarbonyl)-4-(2-ethyl-indazol-3-yl)-[1,2,3,6]tetrahydropyridine To a solution of 1-(tert-butoxycarbonyl)-4-hydroxy-4-(2-ethyl-indazol-3-yl)piperidine (651 mg, 1.89 mmol) in toluene (5 mL) was added (methoxycarbonylsulfamoyl)-triethylammonium hydroxide inner salt (540 mg, 2.27 mmol). After heating up to ~70° C. for 10 min., was added additional 5 mL of toluene. The mixture was stirred at 70° C. for additional 2 h. The mixture was partitioned between ethyl acetate and aq. sodium bicarbonate. Aqueous layer was extracted with ethyl acetate (3×). The combined organic phases were washed with brine, and dried over anhydrous magnesium sulfate. Concentration followed by purification by flash chromatography (hexanes:ethyl acetate=4:1, then 1:1) gave the title compound as a viscous oil.

Step E: 1-(tert-Butoxycarbonyl)-4-(2-ethyl-[5,6,7,8]tetrahydroindazol-3-yl)piperidine A solution of 1-(tert-butoxycarbonyl)-4-(2-ethyl-indazol-3-yl)-[1,2,3,6]tetrahydropyridine (500 mg, 1.53 mmol) in methanol (5 mL) was hydrogenated using Pd(OH)$_2$ (100 mg) under atmospheric H$_2$ for 4.5 h. After the addition of Platinum (IV) oxide (100 mg) hydrogenation was continued for additional 4 h. The mixture was filtered through celite and concentrated to give the title compound as a viscous oil. ESI-MS 333 (M+1); HPLC A: 2.45 min.

Step F: 1-(tert-Butoxycarbonyl)-4-(2-ethylindazol-3-yl)piperidine

To a solution of 1-(tert-butoxycarbonyl)-4-(2-ethyl-[5,6,7,8]tetrahydroindazol-3-yl)piperidine (80 mg, 0.24 mmol) in toluene (3 mL) was added DDQ (115 mg, 0.51 mmol) at rt. After refluxing for 4 h, the mixture was partitioned between ethyl acetate and water. The aqueous layer was extracted with ethyl acetate (3×). The combined organic phases were washed with brine, and dried over anhydrous magnesium sulfate. Concentration gave the title compound as a viscous oil. ESI-MS 274 (M+1-t-Bu); HPLC A: 3.09 min.

Step G: 4-(2-Ethylindazol-3-yl)piperidine, TFA salt

Using essentially the same method as for Piperidine 1, Step B, the title compound was obtained as the TFA salt.

Piperidine 8

4-(1,3-Diethyl-4-methyl-(1H)-pyrazol-5-yl)piperidine di-HCl salt

Step A: 1-(tert-Butoxycarbonyl)-4-(N-methyl-N-methoxycarboxamido)piperidine

A solution of 1-(tert-butoxycarbonyl)isonipecotic acid (13.74 g, 0.06 mol), TEA (14.7 mL, 0.105 mol), 4-DMAP (1.83 g, 0.015 mol), N-ethyl-N'-(3-dimethylaminopropyl)carbodiimide×HCl (11.50 g, 0.06 mol) and O,N-dimethylhydroxylamine×HCl (6.27 g, 0.09 mol) in methylene chloride (250 mL) was stirred at rt for 60 h. The mixture was partitioned between 1 L of ether and 500 mL of water and the layers were separated. The organic layer was washed with 500 mL of 1.0 N HCl, 500 mL of 1.0 N NaOH, 500 mL of sat'd sodium chloride, dried over magnesium sulfate and concentrated to afford the title compound:

$^1$H NMR (500 MHz) δ 1.46 (s, 9H), 1.65–1.80 (4H), 2.76–2.86 (3H), 3.19 (s, 3H), 3.71 (s, 3H), 4.15 (2H).

Step B: 1-(tert-Butoxycarbonyl)-4-formylpiperidine

A solution of 1-(tert-butoxycarbonyl)-4-(N-methyl-N-methoxycarboxamido)piperidine (4.80 g, 17.6 mmol) (from Step A) in methylene chloride (100 mL) at −78° C. was treated with 1.0 M DIBALH solution in methylene chloride (25 mL) and stirred cold for 30 min. The reaction was quenched with 1.0 N HCl (250 mL) and warmed to rt. The quenched mixture was extracted with 300 mL of ether; the extract was washed with 150 mL of 1.0 N NaOH, 150 mL of sat'd sodium chloride, dried over magnesium sulfate and concentrated. Flash chromatography on 125 g of silica gel using 1:1 v/v hexanes/ether as the eluant afforded the title compound:

¹H NMR (500 MHz) δ 1.46 (s, 9H), 1.52–1.59 (m, 2H), 1.85–1.91 (m, 2H), 2.38–2.43 (m, 1H), 2.93 (app t, J=11.0, 2H), 3.95–4.05 (m, 2H), 9.66 (s, 1H).

Step C: 1-(tert-Butoxycarbonyl)-4-(1-(R/S)-hydroxy-2-(R/S)-methyl-3-oxopent-1-yl)piperidine A solution of diisopropylamine (0.63 mL, 4.5 mmol) in THF (16 mL) at 0° C. was treated with 1.6 M n-butyllithium in sol'n in hexanes (2.8 mL). The resulting solution was stirred at 0° C. for 10 min, then cooled to −78° C. 3-Pentanone (0.41 mL, 4.1 mmol) was added and the resulting mixture was stirred cold for 1 h. A solution of 1-(tert-butoxycarbonyl)-4-formylpiperidine (435 mg, 2.05 mmol) (from Step B) in THF (3 mL) was then added. After 15 min, the reaction was quenched with sat'd ammonium chloride (25 mL) and extracted with ether (100 mL). The extract was dried over magnesium sulfate and concentrated. MPLC (Biotage) on a 40S silica cartridge using 4:1 v/v, then 3:2 v/v hexanes/ethyl acetate as the eluent afforded the title compound.

Step D: 1-(tert-Butoxycarbonyl)-4-(1,3-dioxo-2-(R/S)-methylpent-1-yl)piperidine

A solution of oxalyl chloride (0.34 mL, 3.9 mmol) in methylene chloride (12 mL) at −78° C. was treated with DMSO (0.43 mL, 6.0 mmol) and the resulting mixture was stirred cold for 10 min. A solution of 1-(tert-butoxycarbonyl)-4-(1-(R/S)-hydroxy-2-(R/S)-methyl-3-oxopent-1-yl)piperidine (514 mg, 1.7 mmol) (from Step C) was added and the resulting solution was stirred cold for 1 h. N,N-Diisopropylethylamine (2.4 mL, 13.7 mmol) was added and the resulting mixture was warmed to 0° C. The reaction was quenched with 1.0 N HCl (25 mL) and extracted with ether (100 mL). The extract was dried over magnesium sulfate and concentrated. MPLC (Biotage) on a 40S silica cartridge using 2:1 v/v hexanes/ethyl acetate as the eluent afforded the title compound.

Step E: 1-(tert-Butoxycarbonyl)-4-(1,3-diethyl-4-methyl-(1H)-pyrazol-5-yl)piperidine A solution of 1-(tert-butoxycarbonyl)-4-(1,3-dioxo-2-(R/S)-methylpent-1-yl)piperidine (435 mg, 1.5 mmol) (from Step D) in 2:1 v/v acetonitrile/water (12 mL) was treated with ethylhydrazine (34% sol'n in water, 0.28 mL, 1.6 mmol) and the resulting mixture was stirred at rt for 20 h. The reaction mixture was partitioned between 75 mL of ether and 25 mL of sat'd sodium chloride and the layers were separated. The organic layer was dried over magnesium sulfate and concentrated. MPLC (Biotage) on a 40S silica cartridge using 4:1 v/v, then 1:1 v/v hexanes/ethyl acetate as the eluent afforded the title compound:

¹H NMR (500 MHz) δ 1.21 (t, J=7.5, 3H), 1.36 (t, J=7.5, 3H), 1.49 (s, 9H), 1.68–1.72 (m, 2H), 1.86–1.91 (m, 2H), 2.54 (q, J=1.5, 2H), 2.72–2.79 (3H), 4.08 (q, J=7.5, 2H), 4.20–4.30 (m, 2H).

Step F: 4-(1,3-Diethyl-4-methyl-(1H)-pyrazol-5-yl)piperidine di-HCl salt

A solution of 1-(tert-butoxycarbonyl)-4-(1,3-diethyl-4-methyl-(1H)-pyrazol-5-yl)piperidine (348 mg) (from Step E) in 2.5 N HCl in methanol was stirred at rt for 16 h. The solution was concentrated and the resulting solid was suspended in ethyl acetate, filtered and dried to afford the title compound.

Piperidine 9

4-(2-Ethyl-4,5,6,7-tetrahydropyrazolo[1,5-a]pyridin-3-yl)-piperidine, hydrochloride salt Step A: 1-Chloro-5,7-nonanedione To a suspension of NaH (60% dispersion in mineral oil: 8.88 g) in THF (250 mL) was added a mixture of 2-butanone (7.98 g) and methyl 5-chlorovalerate (50.0 g) in THF (100 mL) dropwise via cannula at 0° C. The mixture was stirred at 0° C. for 10 min and at rt for 24 h. After the reaction was quenched with 2 N HCl (200 mL), aqueous layer was extracted with EtOAc (3×). Concentration of the combined organic phase gave a brown colored oil, which was purified by fractional vacuum distillation. The title compound was collected in the temperature range between 95° C. and 110° C. at 10 mmHg. ¹H NMR (500 MHz, CDCl₃) δ 1.14 (t, 3H, J=7.4 Hz), 1.65–1.90 (m, 4H), 2.30–2.60 (m, 4H), 3.50–3.60 (m, 2H), 5.51 (s, 1H).

Step B: 2-Ethyl-4,5,6,7-tetrahydropyrazolo[1,5-a]pyridine

To a solution of 1-chloro-5,7-nonanedione (14.74 g, from Step A) in a mixture of CH₃CN (100 mL) and H₂O (33 mL) was added 4.87 mL of hydrazine. After refluxing for 18 h, the reaction mixture was partitioned between EtOAc and aqueous NaHCO₃ (saturated). Aqueous layer was extracted with EtOAc (3×). Combined organic phase was washed with brine and dried over anhydrous MgSO₄. After concentration, the residue was purified by flash chromatography with 20% EtOAc in hexanes followed by 50% EtOAc in hexanes to give the title compound as a viscous oil. ¹H NMR (500 MHz, CDCl₃) δ 1.24 (t, 3H, J=7.5 Hz), 1.79–1.85 (m, 2H), 1.95–2.05 (m, 2H), 2.62 (q, 2H, J=7.8 Hz), 2.75 (t, 2H, J=6.4 Hz), 4.08 (t, 2H, J=6.1 Hz), 5.78 (s, 1H).

Step C: 3-Bromo-2-ethyl-4,5,6,7-tetrahydropyrazolo[1,5-a]pyridine

To a solution of 2-ethyl-4,5,6,7-tetrahydropyrazolo[1,5-a]pyridine (4.12 g, from Step B) in EtOH (25 mL) was added Br₂ (1.42 mL) dropwise at 0° C. The reaction was stirred at 0° C. for 20 min. The reaction mixture was partitioned between EtOAc and aqueous NaHCO₃ (saturated). Aqueous layer was extracted with EtOAc (3×). Combined organic phase was washed with brine and dried over anhydrous MgSO₄. After concentration, the residue was purified by flash chromatography with 10% EtOAc in hexanes followed by 20% EtOAc in hexanes to give the title compound as a viscous oil. ¹H NMR (500 MHz, CDCl₃) δ 1.25 (t, 3H, J=7.5 Hz), 1.80–1.90 (m, 2H), 1.95–2.05 (m, 2H), 2.55–2.70 (m, 4H), 4.07 (t, 2H, J=6.0 Hz).

Step D: 1-(tert-Butoxycarbonyl)-4-hydroxy-4-(2-ethyl-4,5,6,7-tetrahydropyrazolo[1,5-a]pyridin-3-yl)piperidine To a solution of 3-bromo-2-ethyl-4,5,6,7-tetrahydropyrazolo[1,5-a]pyridine (4.01 g, 17.6 mmol, from Step C) in THF (20 mL) was added tert-BuLi (1.7 M in pentane, 22.8 mL, 38.7 mmol) dropwise at −78° C. After stirring at −78° C. for 30 min., was added tert-butyl 4-oxo-1-piperidinecarboxylate (3.51 g, 17.6 mmol) in THF (10 mL) dropwise at −78° C. The mixture was stirred at −78° C. for 10 min. and at rt for 4 h. After the reaction was quenched with aqueous NH₄Cl, the mixture was partitioned between EtOAc and water. Aqueous layer was extracted with EtOAc (3×). Combined organic phase was washed with brine and dried over anhydrous MgSO₄. Concentration was followed by purification by flash chromatography (hexanes:EtOAc=1:1, then 100% EtOAc) to give the title compound as a foamy solid. ¹HNMR (500 MHz, CDCl₃) δ 1.26 (t, 3H, J=7.4 Hz), 1.49

(s, 9H), 1.75–1.90 (m, 4H), 1.90–2.10 (m, 4H), 2.76 (q, 2H, J=7.6 Hz), 2.89 (t, 2H, J=6.4 Hz), 3.10–3.20 (br, 2H), 3.85–4.05 (br, 2H), 4.09 (t, 2H, J=6.2 Hz). ESI-MS 276 (M-tert-Bu-H$_2$O+H); HPLC A 2.05 min.

Step E: 1-(tert-Butoxycarbonyl)-4-(2-ethyl-4,5,6,7-tetrahydropyrazolo[1,5-a]pyridin-3-yl)-[1,2,3,6]tetrahydropyridine To a solution of 1-(tert-butoxycarbonyl)-4-hydroxy-4-(2-ethyl-4,5,6,7-tetrahydropyrazolo[1,5-a]pyridin-3-yl)piperidine (2.47 g, 7.08 mmol, from Step D) in toluene (20 mL) was added (methoxycarbonylsulfamoyl)-triethylammonium hydroxide inner salt (2.03 g, 8.50 mmol). After stirring at 80° C. for 18 h, the mixture was partitioned between EtOAc and aq. NaHCO$_3$. Aqueous layer was extracted with EtOAc (3×). Combined organic phase was washed with brine and dried over anhydrous MgSO$_4$. Concentration was followed by purification by flash chromatography (hexanes:EtOAc=4:1, then 1:1) to give the title compound as a white solid. $^1$H NMR (500 MHz, CDCl$_3$) δ 1.22 (t, 3H, J=7.5 Hz), 1.50 (s, 9H), 1.80–1.85 (m, 2H), 1.97–2.05 (m, 2H), 2.32 (br s 2H), 2.61 (q, 2H, J=7.5 Hz), 2.69 (t, 2H, J=6.2 Hz), 3.55–3.63 (m, 2H), 4.01 (br s), 4.08 (t, 2H, J=6.2 Hz), 5.50 (br s, 1H).

Step F: 1-(tert-Butoxycarbonyl)-4-(2-ethyl-4,5,6,7-tetrahydropyrazolo[1,5-a]pyridin-3-yl)-piperidine A solution of 1-(tert-butoxycarbonyl)-4-(2-ethyl-4,5,6,7-tetrahydropyrazolo[1,5-a]pyridin-3-yl)-[1,2,3,6]tetrahydropyridine (1.17 g, from Step E) in MeOH (40 mL) was hydrogenated using Pd(OH)$_2$ (300 mg) under atmospheric H$_2$ for 18 h. The mixture was filtered through celite. Concentration was followed by purification by flash chromatography (hexanes:EtOAc=4:1, 1:1, then 100% EtOAc) to give the title compound as a viscous oil. $^1$H NMR (500 MHz, CD$_3$OD) δ 1.23 (t, 3H, J=7.5 Hz), 1.49 (s, 9H), 1.55–1.75 (m, 4H), 1.75–1.85 (m, 2H), 1.90–2.02 (m, 2H), 2.50–2.63 (m, 3H), 2.63–2.80 (m, 4H), 4.07 (t, 2H, J=6.1 Hz), 4.10–4.30 (br, 2H).

Step G: 4-(2-Ethyl-4,5,6,7-tetrahydropyrazolo[1,5-a]pyridin-3-yl)-piperidine, hydrochloride salt To a solution of 1-(tert-Butoxycarbonyl)-4-(2-ethyl-4,5,6,7 tetrahydropyrazolo[1,5-a]pyridin-3-yl)-piperidine (1.41 g, from Step F) in MeOH (15 mL) was added a saturated HCl solution in MeOH (15 mL) at 0° C. After stirring at rt for 3 h, the reaction mixture was concentrated to give the title compound as a foamy solid, which was used without further purification.

Piperidine 10

4-(1,3-Diethyl-5-methyl-1H-pyrazol-4-yl)piperidine, hydrochloride salt

Step A: (±)-Hex-4-yn-3-ol

Propionaldehyde (18.0 mL, 0.25 mol) was added to 500 mL of 0.5 M 1-propynylmagnesium bromide solution in THF at 0° C. The resulting mixture was warmed to rt and stirred for 18 h. The reaction was quenched by pouring it into a well stirred mixture of 300 g of sat'd NH$_4$Cl and 300 g of ice. The resulting mixture was extracted with 2×1 L of ether. The ether extracts were dried over MgSO$_4$, combined and concentrated to afford the title compound which was used without further purification.

Step B: Hex-4-yn-3-one

A mixture of 24 g (0.25 mol) of (±)-hex-4-yn-3-ol (from Step A), 40 g (0.34 mol) of N-methylmorpholine N-oxide and 75 g of 4 A molecular sieves in 250 mL of CH$_2$Cl$_2$ at 0° C. was treated with 2 g (5.7 mmol) of tetrapropylammonium perruthenate. The resulting mixture was warmed to rt and stirred for 1 h. The mixture was filtered through a pad of 400 g of silica gel; the flask and pad were rinsed well with CH$_2$Cl$_2$ (400 mL). The filtrate was concentrated. Distillation at reduced pressure (45 mmHg) afforded the title compound, bp=70–75° C.

Step C: 1,3-Diethyl-5-methylpyrazole

A solution of 18.9 g (0.2 mol) of hex-4-yn-3-one (from Step B) in 120 mL of n-butanol was treated with 40 mL (0.227 mol) of ethyl hydrazine, 34% solution in water. The resulting mixture was heated at reflux for 1.5 h, then cooled to rt. The mixture was concentrated to ~150 µL volume; this was partitioned between 1 L of ether and 250 mL of water. The layers were separated and the organic layer was dried and concentrated to afford the title compound, which was used without further purification. $^1$H-NMR (400 MHz) δ 1.22 (t, J=7.6, 3H), 1.37 (t, J=7.2, 3H), 2.23 (s, 3H), 2.59 (q, J=7.6, 2H), 4.01 (q, J=7.2, 2H), 5.81 (s, 1H).

Step D: 1,3-Diethyl-4-iodo-5-methylpyrazole

A mixture of 13.2 g (95.7 mmol) of 1,3-diethyl-4-5-methylpyrazole (from Step C) and 1.50 g (3.7 mmol) of sorbitan monopalmitate in 200 mL of 2.5 N NaOH was treated with 44 g (0.17 mol) of iodine. Additional portions of sorbitan monopalmitate and iodine were added after 30 min and 60 min. The mixture was partitioned between 1 L of ether and 500 mL of water and the layers were separated. The organic layer was washed with 500 mL of 5% Na$_2$S$_2$O$_3$, dried over MgSO$_4$ and concentrated. Chromatography on a Biotage 75L using 9:1 heptane/EtOAc as the eluant afforded the title compound. $^1$H-NMR (400 MHz) δ 1.22 (t, J=7.6, 3H), 1.36 (t, J=7.2, 3H), 2.27 (s, 3H), 2.58 (q, J=7.6, 2H), 4.10 (q, J=7.2, 2H).

Step E: 1,3-Diethyl-4-(4-pyridyl)-5-methylpyrazole

A mixture of 17.05 g (64.6 mmol) of 1,3-diethyl-4-iodo-5-methylpyrazole (from Step D) and 11.9 g (105.4 mmol) of pyridine 4-boronic acid in 300 mL of dioxane was treated with a solution of 44 g (392 mmol) of potassium tert-butoxide in 100 mL of water. The resulting mixture was treated with 3.75 g (3.2 mmol) of tetrakis(triphenylphosphine)palladium(0), put under an argon atmosphere and heated at 100° C. for 18 h. The mixture was cooled and partitioned between 1 L of ether and 500 mL of water. The organic layer was separated, dried over MgSO$_4$ and concentrated. Flash chromtography on a Biotage 75S afforded of the title compound. $^1$H-NMR (500 MHz) δ 1.19 (t, J=7.5, 3H), 1.48 (t, J=7.5, 3H), 2.27 (s, 3H), 2.67 (q, J=7.5, 2H), 4.09 (q, J=7.5, 2H), 7.18 (dd, J=2.0, 4.5, 2H), 8.60 (dd, J=2.0, 4.5, 2H).

Step F: 1-Benzyl-4-(1,3-diethyl-5-methyl-pyrazol-4-yl)-1,2,3,6-tetrahydropyridine A solution of 7.55 g (35.0 mmol) of 1,3-diethyl-4-(4-pyridyl)-5-methylpyrazole (from Step E) and 4.20 mL (35.0 mmol) of benzyl bromide in 50 mL of MeOH was heated at reflux for 30 min. The mixture was cooled to 0° C. and treated with 2.65 g (70.0 mmol) of sodium borohydride in portions so as to maintain the internal at ~0° C. The resulting mixture was stirred cold for 30 min, then concentrated. The residue was partitioned between 300 mL of CH$_2$Cl$_2$ and 150 mL of 1.0 N NaOH and the layers were separated. The organic layer was dried over MgSO$_4$. The organic layer was extracted with 300 mL of ether; the extract was dried over MgSO₄. The organic layers were combined and concentrated. Chromatography on a Biotage 75L using 9:1 v/v heptane/acetone as the eluant afforded the title compound. ¹H-NMR (400 MHz) δ 1.19 (t, J=7.6, 3H), 1.37 (t, J=7.6, 3H), 2.17 (s, 3H), 2.31–2.35 (m, 2H), 2.58 (q, J=7.6, 2H), 2.66 (t, J=5.6, 2H), 3.13 (app q, J=2.8, 2H), 3.65 (s, 2H), 4.01 (q, J=7.6, 2H), 5.46–5.48 (m, 1H), 7.26–7.39.

Step G: 4-(1,3-Diethyl-5-methyl-pyrazol-4-yl)piperidine

A mixture of 5.70 g (18.4 mmol) of 1-benzyl-4-(1,3-diethyl-5-methyl-pyrazol-4-yl)-1,2,3,6-tetrahydropyridine (from Step F), 25 g (0.4 mol) of ammonium formate and 2.0 g of 20% palladium hydroxide on carbon in 100 mL of methanol was heated at reflux for 1 h. The mixture was cooled and filtered through a pad of Celite. The filtrated was concentrated. The residue was partitioned between 200 mL of CH₂Cl₂ and 100 mL of 10% NH₄OH and the layers were separated. The organic layer was dried over MgSO₄. The aqueous layer was extracted with 2×200 mL of CH₂Cl₂; the extracts were dried over MgSO₄ and all were combined and concentrated. Chromtography on a Biotage 40L using 40:1:0.1, then 20:1:0.1, then 10:1:0.1 v/v/v CH₂Cl₂/MeOH/NH₄OH as the eluant afforded the title compound. ¹H-NMR (500 MHz) δ 1.21 (t, J=7.5, 3H), 1.35 (t, J=7.5, 3H), 1.64 (br d, J=12.5, 2H), 1.78 (dq, J=4.0, 13.0, 2H), 2.24 (s, 3H), 2.50 (tt, J=4.0, 12.5, 1H), 2.62 (q, J=7.5, 2H), 2.69 (dt, J=2.5, 12.0, 2H), 3.16 (app d, J=12.0, 2H), 4.02 (q, J=7.5, 2H); ESI-MS 222 (M+H).

Piperidine 11

4-(2-(2,2,2-Trifluoroethyl)-4,5,6,7-tetrahydro-(2H)-indazol-3-yl)piperidine

Step A: (1-tert-Butoxycarbonylpiperidin-4-yl)-((2R/2S)-cyclohexanon-2-yl)ketone

The title compound was prepared using procedures analogous to those described for Piperidine 8, Steps A–D, except cyclohexanone was substututed for 3-pentanone in Step C. R_F: 0.59 (3:2 v/v hexanes/EtOAc); ¹H-NMR (500 MHz) δ 1.47 (s, 9H), 1.59–1.74 (m, 8H), 2.35–2.40 (m, 4H), 2.68–2.78 (m, 4H), 4.11–4.20 (m, 2H).

Step B: 1-tert-Butoxycarbonyl-4-(2-(2,2,2-trifluoroethyl)-4,5,6,7-tetrahydro-(2H)-indazol-3-yl)piperidine The title compound was prepared using a procedure analogous to that described for Piperidine 8, Step E, except (2,2,2-trifluoroethyl)hydrazine was substututed for ethylhydrazine. R_F: 0.35 (4:1 v/v hexanes/acetone); ¹H-NMR (500 MHz) δ 1.48 (s, 9H), 1.64–1.87 (m, 8H), 2.52–2.73 (m, 7H), 4.24 (br m, 2H), 4.63 (q, J=8.2, 2H).

Step C: 4-(2-(2,2,2-Trifluoroethyl)-4,5,6,7-tetrahydro-(2H)-indazol-3-yl)piperidine A solution of 500 mg (1.3 mmol) of 1-tert-butoxycarbonyl-4-(2-(2,2,2-trifluoroethyl)-4,5,6,7-tetrahydro-(2H)-indazol-3-yl)piperidine (from Step B) in 4.1 mL of CH₂Cl₂ at 0° C. was treated with 2.7 mL of trifluoroacetic acid. After 30 min volatiles were removed under reduced pressure. The residue was partitioned between 25 mL of CH₂Cl₂ and 25 mL of 1 N NaOH. After separating phases, the aqueous layer was extracted with 25 mL of 1 N NaOH. The combined organic layers were dried over Na₂SO₄ and concentrated to afford the title compound, which was used without further purification. ¹H-NMR (500 MHz) δ 1.68–1.95 (m, 9H), 2.61–2.71 (m, 7H), 3.17–3.20 (m, 2H), 4.61 (q, J=8.3, 2H).

Piperidine 12

4-(2-Methyl-4,5,6,7-tetrahydro-(2H)-indazol-3-yl)piperidine

The title compound was prepared using procedures analogous to that described for Piperidine 11, except methylhydrazine was substututed for (2,2,2-trifluoroethyl)hydrazine. ¹H-NMR (500 MHz) δ 1.69–1.89 (m, 8H), 2.33 (br m, 1H), 2.57–2.78 (m, 7H), 3.18–3.21 (m, 2H), 3.77 (s, 3H).

Piperidine 13

4-(2-Propyl-4,5,6,7-tetrahydro-(2H)-indazol-3-yl)piperidine

The title compound was prepared using procedures analogous to that described for Piperidine 11, except propylhydrazine, oxalate salt was substututed for (2,2,2-trifluoroethyl)hydrazine. ¹H-NMR (500 MHz) δ 0.94 (t, J=7.4, 3H), 1.69–1.90 (m, 10H), 2.03 (br s, 1H), 2.58–2.74 (m, 7H), 3.17–3.20 (m, 2H), 3.95 (t, J=7.4, 3H).

Piperidine 14

4-(1-Ethyl-4-methoxy-3-methyl-(1H)-pyrazol-5-yl)piperidine

Step A: 4-Acetyl-1-(tert-Butoxycarbonyl)piperidine

A solution of 1-(tert-butoxycarbonyl)-4-(N-methyl-N-methoxycarboxamido)piperidine (from Piperidine 8, Step A) in anhydrous ether (400 mL) at 0° C. was treated with 55 mL of 1.4 M methyl magnesium bromide in 3:1 toluene and THF over 30 min. After stirring at 0° C. for 1 h, the reaction was poured into a mixture of ice water (400 mL) and acetic acid (8 mL, 150 mmol). The layers were separated and the aqueous layer was extracted twice with ether. The combined organic layers were washed with 0.1 N HCl (200 mL), 3% sodium bicarbonate (200 mL), water (200 mL) and brine (200 mL), dried over sodium sulfate, and concentrated to give the crude product (14.322 g). Flash chromatography (20–80% ethyl acetate in hexanes) gave the title compound as a yellowish oil. R_f: 0.27 (25% ethyl acetate in hexanes). Some starting Weinreb amide was also recovered. R_f: 0.10 (25% ethyl acetate in hexanes). ¹H NMR (500 MHz, CDCl3) δ 4.07–4.14 (m, 2H), 2.75–2.83 (m, 2H), 2.46 (tt, J=11.3 and 3.8 Hz, 1H), 2.17 (s, 3H), 1.82–1.87 (m, 2H), 1.48–1.57 (m, 2 H), 1.46 (s, 9H).

Step B: 1-(tert-Butoxycarbonyl)-4-(1,3-dioxo-but-1-yl)piperidine

A solution of 2.27 g (10.0 mmol) of 4-acetyl-1-(tert-butoxycarbonyl)piperidine (from Step A), 1.95 mL (20.0 mmol) of ethyl acetate and 2.24 g (20.0 mmol) of potassium t-butoxide in 25 mL of MTBE was stirred at rt for 20 h. The reaction was quenched with 50 mL of 0.5 N KHSO₄ and extracted with 150 mL of ether. The extract was dried over MgSO₄ and concentrated. Flash chromatography on 70 g of silica gel using 20:1 v/v hexanes/acetone as the eluant afforded the title compound. The enol form predominated in CDCl3 solution: ¹H NMR (500 MHz, CDCl3) δ 1.46 (s, 9H), 1.53 (dq, J=4.5, 12.5, 2H), 1.81 (app d, J=13.5, 2h), 2.07 (s, 3H), 2.44–2.33 (m, 1H), 2.72–2.79 (m, 2H), 4.18–4.28 (br s, 2H), 5.50 (s, 1H).

Step C: 1-(tert-Butoxycarbonyl)-4-(2-diazo-1,3-dioxo-but-1-yl)piperidine

A solution of 0.51 g (1.8 mmol) of 1-(tert-butoxycarbonyl)-4-(1,3-dioxo-but-1-yl)piperidine (from Step B) and 0.65 g (1.8 mmol) of para-dodecylbenzenesulfonyl azide (Syn. Comm. 1981, 11, 947–956) in $CH_3CN$ at 0° C. was treated with 0.26 mL (1.8 mmol) of triethylamine. The reaction was warmed to rt and stirred for 4.5 hours. The reaction was poured into 100 mL of $Et_2O$ and washed with 100 mL of $H_2O$, 100 mL of 2 N HCl and 100 mL of brine. The organic layer was dried over $MgSO_4$ and concentrated. The residue was purified with a 40M Biotage column using 9:1 v/v of hexanes/acetone to afford the title compound as a light yellow oil: $R_F$: 0.33 (4:1 v/v hexanes/acetone); $^1H$-NMR (500 MHz) δ 1.46 (s, 9H), 1.57–1.76 (m, 4H), 2.42 (s, 3H), 2.82 (m, 2H), 3.24 (m, 1H), 4.14 (m, 2H).

Step D: 1-(tert-Butoxycarbonyl)-4-(1,3-dioxo-2-methoxy-but-1-yl)piperidine

A solution of 532 mg (1.8 mmol) of 1-(tert-butoxycarbonyl)-4-(2-diazo-1,3-dioxo-but-1-yl)piperidine in 5 mL of MeOH was treated with 25 mg (0.056 mmol) of rhodium (II) acetate dimer. The reaction was slowly warmed to 65° C. over 2 hours. Upon cooling, volatiles were removed under reduced pressure. The residue was partitioned between 100 mL of EtOAc and 100 mL of $H_2O$. After separating phases, the organic layer was washed with 100 mL of brine, dried over $Na_2SO_4$ and concentrated. The residue was purified by flash chromatography using 19:1 v/v hexanes/acetone as the eluant to afford the title compound as a yellow oil: $R_F$: 0.39 (4:1 v/v hexanes/acetone); $^1H$-NMR (500 MHz) δ 1.45, 1.47 (2s, 9H), 1.68–1.71 (m, 3H), 2.19, 2.22 (2s, 3H), 2.78–2.89 (m, 2H), 3.44, 3.58 (2s, 3H), 4.03–4.3 (m, 2H).

Step E: 1-tert-Butoxycarbonyl-4-(1-ethyl-4-methoxy-3-methyl-(1H)-pyrazol-5-yl)piperidine The title compound was prepared using a procedure analogous to that described for Piperidine 8, Step E, except 1-(tert-butoxycarbonyl)-4-(1,3-dioxo-2-methoxy-but-1-yl)piperidine (from Step D) was used. Residue purified by preparative HPLC (Column: Chiralcel OD; Mobile Phase: 4:1 v/v hexanes/isopropanol; Flow: 8 mL/min; 220 nm; Retention Time: 10.8 min.) NOE difference spectroscopy was used to determine regiochemistry. $^1H$-NMR (500 MHz) δ 1.37 (t, J=7.2, 3H), 1.41–1.53 (m, 11H), 1.71–1.74 (m, 2H), 1.86–1.97 (m, 2H), 2.21 (s, 3H), 2.66–2.75 (m, 3H), 3.69 (s, 3H), 3.99 (q, J=7.2, 2H), 4.15–4.35 (m, 2H).

Step F: 4-(1-Ethyl-4-methoxy-3-methyl-(1H)-pyrazol-5-yl)piperidine

A solution of 16 mg (0.0.49 mmol) of 1-tert-butoxycarbonyl-4-(1-ethyl-4-methoxy-3-methyl-(1H)-pyrazol-5-yl)piperidine (from Step E) in 0.1 mL of trifluoroacetic acid and 0.15 mL of $CH_2Cl_2$ at 0° C. was stirred for 30 min. Volatiles were removed under reduced pressure. The crude product was partitioned between 25 mL of 1 N NaOH and 25 mL of $CH_2Cl_2$. After separating phases, the aqueous layer was extracted with 3×25 mL of $CH_2Cl_2$. The combined organic layers were dried over $Na_2SO_4$ and concentrated to afford the title compound as a yellow film: $^1H$-NMR (500 MHz) δ 1.36 (t, J=7.2, 3H), 1.72–1.74 (m, 2H), 1.91–2.03 (m, 2H), 2.07 (s, 1H), 2.21 (s, 3H), 2.65–2.73 (m, 3H), 3.19–3.21 (m, 2H), 3.71 (s, 3H), 3.99 (q, J=7.2, 2H).

Piperidine 15

4-(1-Ethyl-3-methoxy-4-methyl-(1H)-pyrazol-5-yl)piperidine

Step A: 4-Propionyl-1-(tert-Butoxycarbonyl)piperidine

The title compound was prepared using a procedure analogous to that described for Piperidine 14, Step A, except ethyl magnesium chloride was substutited for methyl magnesium chloride. $^1H$-NMR (500 MHz) δ 1.06 (t, J=7.3, 3H), 1.46 (s, 9H), 1.49–1.57 (m, 2H), 1.78–1.82 (m, 2H), 2.44–2.50 (m, 3H), 2.75–2.80 (m, 2H), 4.10–4.12 (m, 2H).

Step B: 1-(tert-Butoxycarbonyl)-4-(1,3-dioxo-3-methoxy-2-methyl-prop-1-yl)piperidine A solution of 0.51 g (2.1 mmol) of 4-propionyl-1-(tert-butoxycarbonyl)piperidine (from Step A) and 0.35 mL (17.6 mmol) of dimethylcarbonate in 5 mL of tert-butyl, methyl-ether at 0° C. was treated with 0.45 g (4.0 mmol) of potassium tert-butoxide. After 10 minutes at 0° C., the reaction was stirred at rt for 17 hours and refluxed for 3 hours. The reaction was quenched with 1 N HCl and partitioned between 100 mL of $Et_2O$ and 100 mL of 1 N HCl. After separating phases, the organic layer was washed with 100 mL of brine, dried over $MgSO_4$ and concentrated. The residue was purified with a 40M Biotage column using 9:1 v/v of hexanes/acetone as the eluant to afford the title compound as a straw colored oil: $R_F$: 0.32 (4:1 v/v hexanes/acetone); $^1H$-NMR (500 MHz) δ 1.35 (d, J=7.1, 3H), 1.42–1.66 (m, 11H), 1.79–1.80 (m, 2H), 2.68–2.79 (m, 3H), 3.71 (q, J=7.1, 1H), 3.73, 3.77 (2s, 3H), 4.12 (m, 2H).

Step, C: 1-tert-Butoxycarbonyl-4-(4-methyl-(1H)-pyrazol-3-one-5-yl)piperidine

A solution of 419 mg (1.4 mmol) of 1-(tert-butoxycarbonyl)-4-(1,3-dioxo-3-methoxy-2-methyl-prop-1-yl)piperidine (from Step B) and 0.26 mL (8.4 mmol) of hydrazine in 5 mL of toluene was refluxed for 50 minutes. The reaction was cooled to rt and placed in the freezer overnight. After decanting the solvent, the white solid was triturated with $Et_2O$ to provide the title compound, which was used without further purification. $^1H$-NMR (500 MHz) δ 1.49 (s, 9H), 1.55–1.63 (m, 2H), 1.77–1.79 (m, 2H), 1.90 (s, 3H), 2.69–2.77 (m, 3H), 4.22 (m, 2H), 5.15–5.79 (br m, 2H).

Step D: 1-tert-Butoxycarbonyl-4-(3-methoxy-4-methyl-(1H)-pyrazol-5-yl)piperidine A suspension of 1-tert-butoxycarbonyl-4-(4-methyl-(1H)-pyrazol-3-one-5-yl)piperidine (from Step C) in 12.5 mL (9.9 mmol) of 0.8 M diazomethane in $Et_2O$ was allowed to stand (occasional swirling) until all solids were in solution. Excess diazomethane was quenched with HOAc. The reaction was partitioned between 1 N $NaHCO_3$ and $Et_2O$. After separating phases, the organic layer was dried over $MgSO_4$ and concentrated. The residue was purified by flash chromatography using 19:1 v/v hexanes/acetone, 9:1 v/v hexanes/acetone and 4:1 v/v hexanes/acetone as the gradient to afford the title compound as a yellow oil: $R_F$: 0.18 (4:1 v/v hexanes/acetone); $^1H$-NMR (500 MHz) δ 1.48 (s, 9H), 1.57–1.65 (m, 2H), 1.82–1.85 (m, 2H), 1.89 (s, 3H), 2.70–2.79 (m, 3H), 3.91 (s, 3H), 4.24 (m, 2H)-; $^{13}C$-NMR (125 MHz) δ 55.7 (O—$CH_3$).

Step E: 1-tert-Butoxycarbonyl-4-(1-ethyl-3-methoxy-4-methyl-(1H)-pyrazol-5-yl)piperidine A solution of 30 mg (0.10 mmol) of 1-tert-butoxycarbonyl-4-(3-methoxy-4-methyl-(1H)-pyrazol-5-yl)piperidine (from Step D) in 1 mL of DMF at 0° C. was treated with 3.5 mg (0.15 mmol) of 95% NaH and 0.012 mL (0.15 mmol) of ethyliodide. After 50 minutes, the reaction was partitioned between 25 mL of EtOAc and 25 mL of brine. The organic layer was dried over $Na_2SO_4$ and concentrated. The residue was purified by flash chromatography using 99:1 v/v $CH_2Cl_2$/acetone, 98:2 v/v $CH_2Cl_2$/acetone and 97:3 v/v $CH_2Cl_2$/acetone as the gradient to afford the title compound: $R_F$: 0.39 (19:1 v/v $CH_2Cl_2$/acetone); $^1H$-NMR (500 MHz) δ 1.33 (t, J=7.1, 3H), 1.49 (s, 9H), 1.69–1.72 (m, 2H), 1.82–1.90 (m, 2H), 1.91 (s, 3H), 2.68–2.74 (m, 3H), 3.88 (s, 3H), 3.98 (q, J=7.1, 2H), 4.25 (m, 2H).

Step F: 4-(1-Ethyl-3-methoxy-4-methyl-(1H)-pyrazol-5-yl)piperidine

The title compound was prepared from 1-tert-butoxycarbonyl-4-(1-ethyl-3-methoxy-4-methyl-(1H)-pyrazol-5-yl)piperidine (Step E) using a procedure analogous to that described for Piperidine 14, Step F. $^1$H-NMR (500 MHz) δ 1.33 (t, J=7.1, 3H), 1.70–1.73 (m, 2H), 1.86–1.96 (m, 5H), 2.67–2.72 (m, 3H), 3.19–3.21 (m, 2H), 3.89 (s, 3H), 3.99 (q, J=7.1, 2H).

Piperidine 16

4-(1-Ethyl-3-methoxy-5-methyl-(1H)-pyrazol-4-yl)piperidine

Step A: Ethyl 2-(R/S)-(1-tert-butoxycarbonyl-piperidin-4-yl)-3-(R/S)-hydroxy-butanoate A solution of 0.35 mL (2.5 mmol) of diisopropylamine in 10 mL of THF at 0° C. was treated with 1.6 mL of 1.0 M n-butyllithium solution in hexanes. The resulting mixture was stirred at 0° C. for 10 min, then cooled to −78° C. A solution of 540 mg (2.0 mmol) of ethyl 2-(1-tert-butoxycarbonyl-piperidin-4-yl)acetate (from Piperidine 35, Step A) in 2 mL of THF was added and the resulting solution was stirred cold for 30 min. Acetaldehyde (0.17 mL, 3.0 mmol) was added and the resulting mixture was warmed to 0° C. The reaction was quenched with 10 mL of sat'd NH$_4$Cl and the resulting mixture was partitioned between 50 mL of ether and 25 mL of water. The organic layer was separated, dried over MgSO$_4$ and concentrated. Flash chromatography on 20 g of silica gel using 2:1 v/v hexanes/EtOAc as the eluant afforded the title compound.

Step B: Ethyl 2-(R/S)-(1-tert-butoxycarbonyl-piperidin-4-yl)-3-oxo-butanoate

The title compound was prepared from ethyl 2-(R/S)-(1-tert-butoxycarbonyl-piperidin-4-yl)-3-(R/S)-hydroxy-butanoate (from Step A) using a procedure analogous to that described in Piperdine 8, Step D. $^1$H-NMR (500 MHz) δ 1.11–1.22 (m, 2H), 1.27 (t, J=7.0, 3H), 1.41 (s, 9H), 1.57–1.68 (m, 2H), 2.23 (s, 3H), 2.23–2.30 (m, 1H), 2.72 (br s, 2H), 3.27 (d, J=9.5, 1H), 4.09 (br s, 2H), 4.21 (q, J=7.0, 2H).

Step C: 1-tert-Butoxycarbonyl-4-(3-oxo-5-methyl-(1H)-pyrazol-4-yl)piperidine

A solution of 595 mg (1.9 mmol) of ethyl 2-(R/S)-(1-tert-butoxycarbonyl-piperidin-4-yl)-3-oxo-butanoate (from Step B) and 0.06 mL (1.9 mmol) of hydrazine in 10 mL of xylenes was heated at reflux for 2 h. The resulting mixture was cooled to rt and the solid that precipitated was filtered and dried to afford the title compound. $^1$H-NMR (500 MHz, CD$_3$OD) δ 1.45 (s, 9H), 1.60 (app d, J=12.0, 2H), 1.83 (dq, J=4.0, 13.0, 2H), 2.14 (s, 3H), 2.52–2.58 (m, 1H), 2.65–2.85 (br s, 2H), 4.13 (d, J=13.5, 2H), 4.81 (s, 2H).

Step D: 1-tert-Butoxycarbonyl-4-(3-methoxy-5-methyl-(1H)-pyrazol-4-yl)piperidine The title compound was prepared from 1-tert-butoxycarbonyl-4-(5-methyl-3-oxo-(1H)-pyrazol-4-yl)piperidine (Step C) using a procedure analogous to that described for Piperidine 15, Step D. R$_F$: 0.34 (7:3 v/v hexanes/acetone); $^1$H-NMR (500 MHz) δ 1.47 (s, 9H), 1.57–1.59 (m, 2H), 1.75–1.83 (m, 2H), 2.16 (s, 3H), 2.44–2.50 (m, 1H), 2.70 (m, 2H), 3.86 (s, 3H), 4.17 (m, 2H); $^{13}$C-NMR (125 MHz) δ 55.8 (O—CH$_3$).

Step E: 1-tert-Butoxycarbonyl-4-(1-ethyl-3-methoxy-5-methyl-(1H)-pyrazol-4-yl)piperidine The title compound was prepared from 1-tert-butoxycarbonyl-4-(3-methoxy-5-methyl-(1H)-pyrazol-4-yl)piperidine (Step D) using a procedure analogous to that described for Piperidine 15, Step E. R$_F$: 0.29 (9:1 v/v hexanes/acetone); $^1$H-NMR (500 MHz) δ 1.31 (t, J=7.3, 3H), 1.47 (s, 9H), 1.54–1.56 (m, 2H), 1.79–1.87 (m, 2H), 2.13 (s, 3H), 2.38–2.45 (m, 1H), 2.70 (m, 2H), 3.84 (s, 3H), 3.91 (q, J=7.3, 2H), 4.25 (m, 2H).

Step F: 4-(1-Ethyl-3-methoxy-5-methyl-(1H)-pyrazol-4-yl)piperidine

The title compound was prepared from 1-tert-butoxycarbonyl-4-(1-ethyl-3-methoxy-5-methyl-(1H)-pyrazol-4-yl)piperidine (Step E) using a procedure analogous to that described for Piperidine 14, Step F. $^1$H-NMR (500 MHz) δ 1.33 (t, J=7.2, 3H), 1.61–1.64 (m, 2H), 1.89–1.98 (m, 2H), 2.17 (s, 3H), 2.42–2.49 (m, 1H), 2.68–2.73 (m, 2H), 2.90 (m, 1H), 3.19–3.22 (m, 2H), 3.87 (s, 3H), 3.92 (q, J=7.2, 2H).

Piperidine 17

4-(2-Ethyl-2,4,5,6-tetrahydrocyclopenta[c]-(2H)-pyrazol-3-yl)piperidine

Step A: (1-Benzyloxycarbonylpiperidin-4-yl)-((2R/2S)-cyclopentanon-2-yl)ketone

A solution of 0.59 g (2.2 mmol) of 1-(benzyloxycarbonyl)isonipecotic acid in 4 mL of CH$_2$Cl$_2$ at 0° C. was treated with 0.5 mL (5.7 mmol) of oxalyl chloride and 3 drops of DMF. After 1 hour when the bubbling ceased, volatiles were removed under reduced pressure. The residue was concentrated 3× from CH$_2$Cl$_2$ to afford the acyl chloride, which was used without further purification.

A solution of the above acyl chloride in 6 mL of THF at 0° C. was treated with 0.36 (2.2 mmol) of N-(1-cyclopenten-1-yl)morpholine and 0.35 mL (2.5 mmol) of triethylamine. The reaction was stirred at rt for 6 hours and at 50° C. for 16 hours. The reaction was cooled to rt and treated with 5 mL of H$_2$O and 1 mL of HOAc. After stirring at rt for 2 hours and at 50° C. for 2 hours, volatiles were removed under reduced pressure. The residue was partitioned between 100 mL of CH$_2$Cl$_2$ and 100 mL of 0.5 N HCl. After separating phases, the organic layer was dried over MgSO$_4$ and concentrated. The residue was purified with a 40S Biotage column using 7:3 v/v of hexanes/EtOAc as the eluant to afford impure title compound: R$_F$: 0.36 (3:2 v/v hexanes/EtOAc); $^1$H-NMR (500 MHz) (mixture of keto and enol tautomers) δ 1.43–4.26 (m, 16H), 5.13–5.29 (m, 2H), 7.27–7.39 (m, 5H).

Step B: 1-Benzyloxycarbonyl-4-(2-ethyl-2,4,5,6-tetrahydrocyclopenta[c]-(2H)-pyrazol-3-yl)piperidine The title compound was prepared from (1-benzyloxycarbonylpiperidin-4-yl)-((2R/2S)-cyclopentanon-2-yl)ketone (Step A) using a procedure analogous to that described for Piperidine 8, Step E. R$_F$: 0.13 (4:1 v/v hexanes/acetone); $^1$H-NMR (500 MHz) δ 1.43 (t, J=7.3, 3H), 1.65–1.84 (m, 4H), 2.35–2.40 (m, 2H), 2.60–2.87 (m, 7H), 4.06 (q, J=7.3, 2H), 4.32 (m, 2H), 5.16 (s, 2H), 7.27–7.39 (m, 5H).

Step C: 4-(2-Ethyl-2,4,5,6-tetrahydrocyclopenta[c]-(2H)-pyrazol-3-yl)piperidine

A mixture of 85 mg (0.24 mmol) of 1-benzyloxycarbonyl-4-(2-ethyl-2,4,5,6-tetrahydrocyclopenta[c]-(2H)-pyrazol-3-yl)piperidine (from Step B) and 26 mg of 10% palladium on carbon in 2 mL of MeOH was hydrogenated at rt under a balloon of hydrogen for 1.25 hours. The reaction was filtered and concentrated to afford the title compound as a colorless film, which was used without further purification. $^1$H-NMR (500 MHz) δ 1.38 (t, J=7.3, 3H), 1.64–1.80 (m, 4H), 2.31–2.36 (m, 2H), 2.60–2.73 (m, 7H), 3.05–3.18 (m, 3H), 4.00 (q, J=7.3, 2H).

Piperidine 18

4-(4-Ethyl-3-methoxy-4-methyl-(4H)-pyrazol-5-yl)piperidine

Step A: 1-tert-Butoxycarbonyl-4-(4-ethyl-3-hydroxy-4-methyl-(4H)-pyrazol-5-yl)piperidine A solution of 255 mg (0.9 mmol) of 1-tert-butoxycarbonyl-4-(4-methyl-(1H)-pyrazol-3-one-5-yl)piperidine (from Piperidine 15, Step C) and 0.155 mL (1.0 mmol) of freshly distilled tetramethylethylene diamine in 3 mL of THF at −78° C. was treated with 0.8 mL (2.0 mmol) of 2.5 M n-butyl lithium in hexanes (J. Med. Chem. 1996, 39, 3920–3928). After stirring for 15 minutes at −78° C., the reaction was warmed to 0° C. for 15 minutes. Upon recooling to −78° C., 0.11 mL (1.3 mmol) of ethyliodide was added. After warming to rt and stirring for 19 hours, the reaction was cooled to 0° C. and quenched with 1 N HCl. The reaction mixture was partitioned between 100 mL of EtOAc and 100 mL of 1 N HCl. After separating phases, the organic layer washed with 100 mL of brine, dried over $Na_2SO_4$ and concentrated. The residue was purified by flash chromatography using 99:1 v/v $CH_2Cl_2$/MeOH, 98:2 v/v $CH_2Cl_2$/MeOH and 97:3 v/v $CH_2Cl_2$/MeOH as the gradient to afford the title compound as a white solid: $R_F$: 0.40 (19:1 v/v $CH_2Cl_2$/MeOH); $^1$H-NMR (500 MHz) δ 0.73 (t, J=7.4, 3H), 1.26 (s, 3H), 1.47 (s, 9H), 1.59–1.85 (m, 6H), 2.38 (m, 1H), 2.76–2.81 (m, 2H), 4.16–4.21 (m, 2H), 8.61 (br s, 1H).

Step B: 1-tert-Butoxycarbonyl-4-(4-ethyl-3-methoxy-4-methyl-(4H)-pyrazol-5-yl)piperidine A suspension of 49 mg (0.15 mmol) of 1-tert-butoxycarbonyl-4-(4-ethyl-3-hydroxy-4-methyl-(4H)-pyrazol-5-yl)piperidine (from Step A), 50 mg (0.36 mmol) of potassium carbonate and 0.06 mL (0.96 mmol) of methyliodide in 0.3 mL of acetonitrile was stirred at rt for 17 hours and 85° C. for 7 hours. The reaction was partitioned between 25 mL of EtOAc and 25 mL of brine. After separating phases, the organic layer was dried over $Na_2SO_4$ and concentrated. The residue was purified by flash chromatography using 4:1 v/v of hexanes/acetone as the eluant to afford the title compound as a colorless film: $R_F$: 0.21 (4:1 v/v hexanes/acetone); $^1$H-NMR (500 MHz) δ 0.65 (t, J=7.4, 3H), 1.21 (s, 3H), 1.45 (s, 9H), 1.57–1.66 (m, 2H), 1.73–1.81 (m, 4H), 2.37 (m, 1H), 2.73–2.78 (m, 2H), 3.27 (s, 3H), 4.15–4.20 (m, 2H); $^{13}$C-NMR (125 MHz) δ 54.4 (O—$CH_3$).

Step C: 4-(4-Ethyl-3-methoxy-4-methyl-(4H)-pyrazol-5-yl)piperidine

A solution of 23.5 mg (0.072 mmol) of t-tert-butoxycarbonyl-4-(4-ethyl-3-methoxy-4-methyl-(4H)-pyrazol-5-yl)piperidine (from Step B) in 1 N HCl in methanol was stirred at rt for 4 h. The crude product was partitioned between 10 mL of 1 N NaOH and 25 mL of $CH_2Cl_2$. After separating phases, the aqueous layer was extracted with 3×25 mL of $CH_2Cl_2$. The combined organic layers were dried over $Na_2SO_4$ and concentrated to afford the title compound, which was used without further purification. $^1$H-NMR (500 MHz) δ 0.65 (t, J=7.4, 3H), 1.21 (s, 3H), 1.57–1.94 (m, 6H), 2.40 (m, 1H), 2.70–2.74 (m, 2H), 3.20–3.28 (m, 2H), 3.28 (s, 3H).

Piperidine 19

4-(1-Ethyl-3-hydroxymethyl-4-methyl-(1H)-pyrazol-5-yl)piperidine

Step A: 1-(tert-Butoxycarbonyl)-4-(4-benzyloxy-1,3-dioxo-2-(R/S)-methylbut-1-yl)piperidine The title compound was prepared using a procedure analogous to that described for Piperidine 15, Step B, except benzyloxyacetic acid, methyl ester was substutited for dimethylcarbonate. $R_F$: 0.27 (4:1 v/v hexanes/acetone); $^1$H-NMR (500 MHz) δ 1.27 (d, J=6.9, 3H), 1.43–1.86 (m, 15H), 2.54–2.70 (m, 3H), 3.78–4.76 (m, 5H), 7.27–7.40 (m, 5H).

Step B: 1-(tert-Butoxycarbonyl)-4-(1-ethyl-3-benzyloxymethyl-4-methyl-(1H)-pyrazol-5-yl)piperidine The title compound was prepared from 1-(tert-butoxycarbonyl)-4-(4-benzyloxy-1,3-dioxo-2-(R/S)-methylbut-1-yl)piperidine (from Step A) using a procedure analogous to that described for Piperidine 8, Step E. $R_F$: 0.13 (9:1 v/v hexanes/acetone); $^1$H-NMR (500 MHz) δ 1.39 (t, J=7.2, 3H), 1.50 (s, 9H), 1.69–1.71 (m, 2H), 1.85–1.94 (m, 2H), 2.08 (s, 3H), 2.75–2.81 (m, 3H), 4.13 (q, J=7.2, 2H), 4.15–4.27 (m, 2H), 4.49 (s, 2H), 4.57 (s, 2H), 7.26–7.38 (m, 5H).

Step C: 1-(tert-Butoxycarbonyl)-4-(1-ethyl-3-hydroxymethyl-4-methyl-(1H)-pyrazol-5-yl)piperidine The title compound was prepared from 1-(tert-butoxycarbonyl)-4-(1-ethyl-3-benzyloxymethyl-4-methyl-(1H)-pyrazol-5-yl)piperidine (from Step B) using a procedure analogous to that described for Pyrrolidine 1, Step E. $R_F$: 0.21 (3:2 v/v hexanes/acetone); $^1$H-NMR (500 MHz) δ 1.36 (t, J=7.2, 3H), 1.48 (s, 9H), 1.67–1.70 (m, 2H), 1.84–1.93 (m, 2H), 2.08 (s, 3H), 2.74–2.80 (m, 3H), 3.14 (br m, 1H), 4.10 (q, J=7.2, 2H), 4.12–4.26 (m, 2H), 4.59 (s, 2H).

Step D: 4-(1-Ethyl-3-hydroxymethyl-4-methyl-(1H)-pyrazol-5-yl)piperidine

The title compound was prepared from 1-(tert-butoxycarbonyl)-4-(1-ethyl-3-hydroxymethyl-4-methyl-(1H)-pyrazol-5-yl)piperidine (from Step C) using a procedure analogous to that described for Piperidine 8, Step F.

Piperidine 20

4-(1-Ethyl-3-methoxymethyl-4-methyl-(1H)-pyrazol-5-yl)piperidine

Step A: 1-(tert-Butoxycarbonyl)-4-(1-ethyl-3-methoxymethyl-4-methyl-(1H)-pyrazol-5-yl)piperidine The title compound was prepared from 1-(tert-butoxycarbonyl)-4-(1-ethyl-3-hydroxymethyl-4-methyl-(1H)-pyrazol-5-yl)piperidine (from Piperidine 19, Step C) using a procedure analogous to that described for Piperidine 15, Step E, except methyliodide was substutited for ethyliodide. $R_F$: 0.47 (3:2 v/v hexanes/acetone); $^1$H-NMR (500 MHz) δ 1.39 (t, J=7.2, 3H), 1.49 (s, 9H), 1.69–1.71 (m, 2H), 1.85–1.94 (m, 2H), 2.08 (s, 3H), 2.75–2.81 (m, 3H), 3.39 (s, 3H), 4.12 (q, J=7.2, 2H), 4.14–4.27 (m, 2H), 4.38 (s, 2H).

Step B: 4-(1-Ethyl-3-methoxymethyl-4-methyl-(1H)-pyrazol-5-yl)piperidine

The title compound was prepared from 1-(tert-butoxycarbonyl)-4-(1-ethyl-3-methoxymethyl-4-methyl-(1H)-pyrazol-5-yl)piperidine (from Step A) using a procedure analogous to that described for Piperidine 8, Step F. $^1$H-NMR (500 MHz) δ 1.36 (t, J=7.2, 3H), 1.71–1.74 (m, 2H), 1.97–2.09 (m, 2H), 2.11 (s, 3H), 2.72–2.80 (m, 3H), 3.25–3.35 (m, 2H), 3.37 (s, 3H), 4.11 (q, J=7.2, 2H), 4.37 (s, 2H).

Piperidine 21

4-(2-Methoxy-4,5,6,7-tetrahydropyrazolo[1,5-a]pyridin-3-yl)-piperidine

Step A: (2R/S, 3R/S)-2-(1-tert-Butoxycarbonyl-piperidin-4-yl)-7-chloro-3-hydroxy-heptanoic acid, ethyl ester A solution of 0.32 mL (2.2 mmol) of diisopropylamine in 10 mL of THF at 0° C. was treated with 0.92 mL (2.3 mmol) of 2.5 M n-butyllithium in sol'n in hexanes. The resulting solution was stirred at 0° C. for 10 min, then cooled to −78° C. A solution of 0.51 g (1.8 mmol) of (1-tert-butoxycarbonylpiperidin-4-yl)acetic acid, ethyl ester (from Piperidine 35, Step A) in 2 mL of THF was added. After stirring for 30 minutes, a solution of 0.26 g (2.1 mmol) 5-chloropentanal in 2 mL of THF was added (J. Org. Chem. 1981, 46, 2007). The reaction was stirred for 1.75 hours at −78° C. and 3.5 hours at 0° C. After quenching the reaction with saturated $NH_4Cl$, volatiles were removed under reduced pressure. The residue was partitioned between 100 mL of $Et_2O$ and 100 mL of $H_2O$. After separating phases, the organic layer was washed with 100 mL of 0.5 N HCl and 100 mL of 1 N $NaHCO_3$, dried over $MgSO_4$ and concentrated. The residue was purified with a 40M Biotage column using 3:1 v/v of hexanes/EtOAc as the eluant to afford impure title compound: $R_F$: 0.27 (7:3 v/v hexanes/EtOAc); $^1$H-NMR (500 MHz) δ 1.24–2.08 (m, 23H), 2.38 (t, J=6.2, 1H), 2.63–2.71 (m, 2H), 3.53–3.56 (m, 2H), 3.92 (m, 1H), 4.09–4.19 (m, 4H).

Step B: (2R/S)-2-(1-tert-Butoxycarbonyl-piperidin-4-yl)-7-chloro-3-keto-heptanoic acid, ethyl ester The title compound was prepared from (2R/S, 3R/S)-2-(1-tert-butoxycarbonyl-piperidin-4-yl)-7-chloro-3-hydroxy-heptanoic acid, ethyl ester (from Step A) using a procedure analogous to that described for Piperidine 8, Step D. $R_F$: 0.30 (4:1 v/v hexanes/EtOAc); $^1$H-NMR (500 MHz) δ 1.09–1.22 (m, 2H), 1.27 (t, J=7.1, 3H), 1.45 (s, 9H), 1.55 (m, 1H), 1.63–1.79 (m, 5H), 2.29 (m, 1H), 2.46–2.75 (m, 4H), 3.30 (d, J=9.6, 1H), 3.51–3.54 (m, 2H), 4.06–4.21 (m, 4H).

Step C: 1-(tert-Butoxycarbonyl)-4-(4,5,6,7-tetrahydropyrazol-2-one[1,5-a]pyridin-3-yl)-piperidine A solution of 264 mg (0.67 mmol) of (2R/S)-2-(1-tert-butoxycarbonyl-piperidin-4-yl)-7-chloro-3-keto-heptanoic acid, ethyl ester (from Step B) and 0.064 mL of hydrazine (2.0 mmol) in 2 mL of xylene was refluxed for 24 hours. The reaction was cooled to rt and volatiles removed under reduced pressure. The residue was purified by flash chromatography using 39:1 v/v of $CH_2Cl_2$/MeOH as the eluant to afford the title compound: $R_F$: 0.41 (19:1 v/v $CH_2Cl_2$/MeOH); $^1$H-NMR (500 MHz) δ 1.48 (s, 9H), 1.63–1.65 (m, 2H), 1.79–1.85 (m, 4H), 1.96–2.03 (m, 2H), 2.51 (m, 1H), 2.66–2.72 (m, 4H), 3.93–3.95 (m, 2H), 4.15–4.22 (m, 2H), 6.8 (br m, 1H).

Step D: 1-(tert-Butoxycarbonyl)-4-(2-methoxy-4,5,6,7-tetrahydropyrazolo[1,5-a]pyridin-3-yl)-piperidine The title compound was prepared from 1-(tert-butoxycarbonyl)-4-(4,5,6,7-tetrahydropyrazol-2-one[1,5-a]pyridin-3-yl)-piperidine (from Step C) using a procedure analogous to that described for Piperidine 15, Step D. $R_F$: 0.72 (19:1 v/v $CH_2Cl_2$/MeOH); $^1$H-NMR (500 MHz) δ 1.45 (s, 9H), 1.57–1.59 (m, 2H), 1.71–1.81 (m, 4H), 1.94–1.98 (m, 2H), 2.44 (m, 1H), 2.62–2.68 (m, 4H), 3.84 (s, 3H), 3.91–3.93 (m, 2H), 4.15–4.22 (m, 2H); $^{13}$C-NMR (125 MHz) δ 55.7 (O—$CH_3$).

Step E: 4-(2-Methoxy-4,5,6,7-tetrahydropyrazolo[1,5-a]pyridin-3-yl)-piperidine

The title compound was prepared from 1-(tert-butoxycarbonyl)-4-(2-methoxy-4,5,6,7-tetrahydropyrazolo[1,5-a]pyridin-3-yl)-piperidine (from Step D) using a procedure analogous to that described for Piperidine 8, Step F.

Piperidines 22–25 were prepared through analogous procedures for Piperidine 8, except substituting the appropriate ketone in Step C.

Piperidine 22

4-(2-Ethyl-2,4,6,7-tetrahydrothiopyrano[4,3-c]pyrazol-3-yl)piperidine

Piperidine 23

4-(2-Ethyl-2,4,6,7-tetrahydrothiopyrano5,5-dioxide[4,3-c]pyrazol-3-yl)piperidine

Piperidine 23A 4-(2-Eethyl-2,4,6,7-tetrahydropyrano[4,3-c]pyrazol-3-yl)piperidine

Piperidine 24

4-(3-tert-Butyl-1-ethyl-4-methyl-(1H)-pyrazol-5-yl)piperidine

Piperidine 24A 4-(3-tert-Butyl-2-ethyl-4-methyl-(1H)-pyrazol-5-yl)piperidine

Piperidine 25

4-(1-Ethyl-4-methyl-3-iso-propyl(1H)-pyrazol-5-yl)piperidine

Piperidines 26–30 were prepared through analogous procedures for Piperidine 15, except substituting the appropriate ester for dimethylcarbonate in Step B.

Piperidine 26

4-(1,4-Diethyl-3-methyl-(1H)-pyrazol-5-yl)piperidine

Piperidine 27

4-(3-Cyclobutyl-1-ethyl-4-methyl-(1H)-pyrazol-5-yl)piperidine

Piperidine 28

4-(1,3,4-Triethyl-(1H)-pyrazol-5-yl)piperidine

Piperidine 29

4-(3,4-Dimethyl-1-ethyl-(1H)-pyrazol-5-yl)piperidine

Piperidine 30

4-(3-Cyclopropyl-1-ethyl-4-methyl-(1H)-pyrazol-5-yl)piperidine

Piperidines 31–34 were prepared through analogous procedures for Piperidine 9, except substituting the appropriate diketone in Step B.

Piperidine 31

4-(1,3,5-Triethyl-(1H)-pyrazol-4-yl)piperidine, hydrochloride salt

Piperidine 32

4-(1,3,5-Trimethyl-(1H)-pyrazol-4-yl)piperidine, hydrochloride salt

Piperidine 33

4-(1-Ethyl-3,5-dimethyl-(1H)-pyrazol-4-yl)piperidine, hydrochloride salt

Piperidine 34

4-(1,5-Diethyl-3-methyl-(1H)-pyrazol-4-yl)piperidine, hydrochloride salt

Piperidine 35

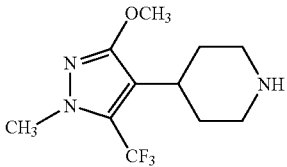

4-(3-Methoxy-1-methyl-5-(trifluoromethyl)-1H-pyrazol-4-yl)piperidine

Step A: 1-(tert-Butoxycarbonyl)-4-piperidineacetic acid ethyl ester

A suspension of sodium hydride (1.90 g of 60% oil dispersion, 48 mmol) in THF (150 mL) was cooled to 0° C. in a 3-neck flask fitted with a mechanical stirrer. Triethyl phosphonoacetate (9.90 mL, 11.2 g, 50 mmol) was added to the stirred mixture, producing vigorous gas evolution. After 20 min, 1-(tert-butoxycarbonyl)-4-piperidone (8.00 g, 40 mmol) was added to the clear solution. After an additional 20 min, the cooling bath was removed and the mixture was stirred for 2 h. The mixture was partitioned between Et$_2$O (200 mL) and 1 N aq. NaOH (200 mL). The organic layer was washed with saturated aq. NaCl and the aqueous layers were extracted in succession with Et$_2$O (100 mL). The organic layers were dried (Na$_2$SO$_4$), decanted, and evaporated to give 11.6 g of colorless crystals. This material was dissolved in hexane (50 mL) at 60° C. and the solution was allowed to cool to RT, yielding 1-(t-butoxycarbonyl)-4-(carboethoxymethylidene)piperidine as white crystals. A second crop of crystals was similarly obtained by evaporation of the mother liquor and recrystallization of the residue.

1-(tert-Butoxycarbonyl)-4-(carboethoxymethylidene)piperidine (9.97 g, 37 mmol) in 95% ethanol (75 mL) containing 10% palladium on carbon (250 mg) was hydrogenated on a Parr shaker at 36 psi. After 1.5 h, the mixture was filtered through Celite with additional 95% ethanol, and the filtrate was evaporated to give the title compound as a colorless oil. For the title compound: $^1$H NMR (500 MHz, CDCl$_3$) δ 4.15 (q, J=7, 2H), 4.09 (bd, J=12, 2H), 2.73 (bt, J=12, 2H), 2.24 (d, J=7, 2H), 2.00–1.90 (m, 1H), 1.70 (bd, J=12, 2H), 1.47 (s, 9H), 1.27 (t, J=7, 3H), 1.18 (qd, J=12, 4, 2H).

Step B: 1-(tert-Butoxycarbonyl)-α-(trifluoroacetyl)-4-piperidineacetic acid ethyl ester THF (3.0 mL) and ethyl trifluoroacetate (1.32 mL, 1.58 g, 11.1 mmol) were added to sodium hydride (442 mg of 60% oil dispersion, 11.1 mmol) in a flask fitted with a mechanical stirrer and a reflux condenser. 1-(tert-butoxycarbonyl)-4-piperidineacetic acid ethyl ester (1.50 g, 5.52 mmol) dissolved in THF (2.0 mL) was added over 30 min, with additional THF (2×1 mL) to complete the transfer. The mixture was warmed to 45° C. overnight. An additional portion of ethyl trifluoroacetate (1.0 mL, 1.19 g, 8.4 mmol) was added the temperature was increased to 70° C. for 17 h. After cooling to RT, the mixture was partitioned between EtOAc (50 mL) and a mixture of saturated aq. NaCl (25 mL) and 2 N aq. HCl (10 mL). The aqueous layer was extracted with EtOAc (25 mL). The organic layers were washed in succession with saturated aq. NaCl (2×10 mL), dried (Na$_2$SO$_4$), decanted, and evaporated. The crude product was purified by flash column chromatography on silica gel, eluting with 90:10 to 85:15 v/v hexanes/EtOAc to give the title compound as a colorless oil. For the title compound: $^1$H NMR (500 MHz, CDCl$_3$) showed an apparent mixture of tautomers; ESI-MS 268.2 (M+H−100); HPLC A: 3.3 min.

Step C: 1-(tert-Butoxycarbonyl-4-(3-hydroxy-5-(trifluoromethyl)-(1H)-pyrazol-4-yl)piperidine Anhydrous hydrazine (0.040 mL, 41 mg, 1.27 mmol) was added to a stirred solution of 1-(tert-butoxycarbonyl)-α-(trifluoroacetyl)-4-piperidineacetic acid ethyl ester (275 mg, 0.75 mmol, from Step B) in toluene (2.0 mL) at RT. The mixture was warmed to 60° C. for 4 h, followed by 16 h at 80° C. The mixture was allowed to cool to RT, transferred to another flask with CH$_3$OH, and evaporated to give the title compound as a white solid. For the title compound: $^1$H NMR (500 MHz, CD$_3$OD) δ 4.15 (bd, J=13, 2H), 2.86–2.70 (m, 3H), 1.88 (bq, J=12, 2H), 1.62 (bd, J=13, 2H), 1.47 (s, 9H); ESI-MS 280.3 (M+H−56) and 236.3 (M+H−100); HPLC A: 3.0 min.

Step D: 1-(tert-Butoxycarbonyl-4-(3-methoxy-1-methyl-5-(trifluoromethyl)-(1H)-pyrazol-4-yl)piperidine Potassium carbonate (270 mg, 1.95 mmol) and iodomethane (0.12 mL, 0.27 g, 1.9 mmol) were added to a stirred suspension of 1-(tert-butoxycarbonyl-4-(3-hydroxy-5-(trifluoromethyl)-(1H)-pyrazol-4-yl)piperidine (200 mg, 0.60 mmol, from Step C) in CH$_3$CN (3.0 mL) at RT. After 5 d, the reaction mixture was diluted into saturated aq. NH$_4$Cl (15 mL) and extracted with EtOAc (25 mL). The organic layer was washed with saturated aq. NaCl (15 mL), dried (Na$_2$SO$_4$), decanted, and evaporated to give 215 mg of colorless oil. Purification by flash column chromatography on silica gel, eluting with 90:10 to 50:50 hexanes/EtOAc gave the title compound as a colorless syrup. For the title compound: $^1$H NMR (500 MHz, CD$_3$OD) δ 4.13 (d, J=12, 2H), 3.87 (s, 3H), 3.78 (s, 3H), 2.83 (tt, J=12, 3, 1H), 2.75 (bs, 2H), 1.89 qd, J=12, 4, 2H), 1.55 (d, J=12, 2H), 1.48 (s, 9H); ESI-MS 308.2 (M+H−56); HPLC A: 3.5 min.

Later column fractions gave 50 mg of the isomeric product 1-(tert-butoxycarbonyl-4-(5-methoxy-1-methyl-3-(trifluoromethyl)-(1H)-pyrazol-4-yl)piperidine: $^1$H NMR (500 MHz, CD$_3$OD) δ 4.16 (d, J=12, 2H), 3.92 (s, 3H), 3.73 (s, 3H), 2.88–2.72 (m, 3H), 1.79–1.68 (m, 4H), 1.47 (s, 9H).

Step E: 4-(3-Methoxy-1-methyl-5-(trifluoromethyl)-(1H)-pyrazol-4-yl)piperidine

Trifluoroacetic acid (3.0 mL) was added to a solution of 1-(tert-butoxycarbonyl-4-(3-methoxy-1-methyl-5-(trifluoromethyl)-(1H)-pyrazol-4-yl)piperidine (150 mg, 0.41 mmol, from Step D) in CH$_2$Cl$_2$ (3.0 mL). After 2 h, the reaction was concentrated and the residue was dissolved in EtOAc (15 mL) and washed with saturated aq. NaHCO$_3$ (6 mL) followed by saturated aq. NaCl (5 mL). The organic layer was dried (Na$_2$SO$_4$), decanted, and evaporated to give the title compound as a white solid. For the title compound: $^1$H NMR (500 MHz, CD$_3$OD) δ 3.89 (s, 3H), 3.80 (s, 3H), 3.32 (d, J=13, 2H), 2.95 (tt, J=13, 4, 1H), 2.93 (td, J=13, 3, 2H), 2.18 (qd, J=13, 4, 2H), 1.76 (d, J=13, 2H); ESI-MS 264.1 (M+H); HPLC A: 1.3 min.

Piperidine 36

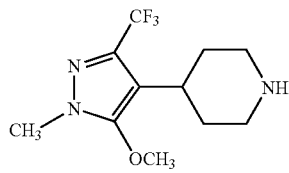

4-(5-Methoxy-1-methyl-3-(trifluoromethyl)-(1H)-pyrazol-4-yl)piperidine

The title compound was prepared using conditions similar to those described in Piperidine 35, Step E, substituting 1-(tert-butoxycarbonyl-4-(5-methoxy-1-methyl-3-(trifluoromethyl)-(1H)-pyrazol-4-yl)piperidine (from Piperidine 35, Step D) for 1-(tert-butoxycarbonyl-4-(3-methoxy-1-methyl-5-(trifluoromethyl)-(1H)-pyrazol-4-yl)piperidine. For the title compound: $^1$H NMR (500 MHz, CD$_3$OD) δ 3.94 (s, 3H), 3.72 (s, 3H), 3.10 (d, J=13, 2), 2.70 (tt, J=13, 4, 1H), 2.64 (td, J=13, 3, 2H), 1.84 (qd, J=13, 4, 2H), 1.71 (d, J=13, 2H); ESI-MS 264.1 (M+H); HPLC A: 1.1 min.

Bicyclic Amine 1

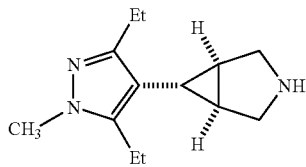

(1α,5α,6α)-6-(3,5-Diethyl-1-methyl-(1H)-pyrazol-4-yl)-3-azabicyclo[3.1.0]hexane

Step A: (1α,5α,6α)-3-(tert-Butoxycarbonyl)-6-(hydroxymethyl)-3-azabicyclo[3.1.0]hexane A solution of di-tert-butyl dicarbonate (967 mg, 4.42 mmol) in CH$_2$Cl$_2$ (3.0 mL) was added to a stirred solution of (1α,5α,6α)-6-(hydroxymethyl)-3-azabicyclo[3.1.0]hexane (456 mg, 4.02 mmol, for preparation see K. E. Brighty and M. J. Castaldi, Synlett, 1996, 1097–1099) in CH$_2$Cl$_2$ (7.0 mL) at RT. After 15 h, the solution was partitioned between 2 N aq. HCl (50 mL) and EtOAc (50 mL). The organic layer was washed with saturated aq. NaHCO$_3$ (50 mL) followed by saturated aq. NaCl (50 mL). The aqueous layers were extracted in succession with EtOAc (2×50 mL). The organic layers were dried (Na$_2$SO$_4$), decanted, and evaporated. The crude product was purified by flash column chromatography on silica gel, eluting with 80:20 v/v to 0:100 hexane/EtOAc to give the title compound as a colorless syrup. For the title compound: $^1$H NMR (500 MHz, CDCl$_3$) δ 3.60 (d, J=11, 2H), 3.53 (d, J=6, 2H), 3.36 (d, J=11, 2H), 1.44 (s, 11H), 0.96 (tt, J=6, 3, 1H), ESI-MS 158.1 (M+H−56); HPLC A: 2.1 min.

Step B: (1α,5α,6α)-3-(tert-Butoxycarbonyl)-3-azabicyclo[3.1.0]hexane-6-carboxaldehyde A solution of DMSO (1.0 mL, 1.1 g, 7.0 mmol) in CH$_2$Cl$_2$ (0.6 mL) was added dropwise to a solution of oxalyl chloride (0.61 mL, 0.89 g, 7.0 mmol) in CH$_2$Cl$_2$ (6.4 mL) cooled in a dry ice/i-PrOH bath. After 5 min, (1α,5α,6α)-3-(tert-butoxycarbonyl)-6-(hydroxymethyl)-3-azabicyclo[3.1.0]hexane (600 mg, 2.81 mmol, from Step A) was added slowly in CH$_2$Cl$_2$ (6.4 mL). After another 15 min, N,N-diisopropylethylamine (4.9 mL, 3.6 g, 28 mmol) was added and the reaction was allowed to warm to 40° C. over 1.5 h. The reaction mixture was poured into water (50 mL) and extracted with CH$_2$Cl$_2$ (3×50 mL). The combined organic layers were washed with saturated aq. NaCl (50 mL), dried (Na$_2$SO$_4$), decanted, and evaporated. Purification by flash column chromatography on silica gel, eluting with hexanes followed by 80:20 to 50:50 v/v hexanes/EtOAc gave the title compound as a colorless syrup. For the title compound: $^1$H NMR (500 MHz, CDCl$_3$) δ 9.44 (d, J=4, 1H), 3.72 (d, J=11, 1H), 3.64 (d, J=11, 1H), 3.51–3.44 (m, 2H), 2.24–2.19 (m, 2H), 1.82 (q, J=4, 1H), 1.45 (s, 9H).

Step C: (1α,5α,6α)-3-(tert-Butoxycarbonyl)-6-(2-nitrobut-1-enyl)-3-azabicyclo[3.1.0]hexane Potassium fluoride (18 mg, 0.31 mmol) and 1-nitropropane (1.1 mL, 1.1 g, 12.5 mmol) were added to a solution of (1α,5α,6α)-3-(tert-butoxycarbonyl)-3-azabicyclo[3.1.0]hexane-6-carboxaldehyde (1.32 g, 6.25 mmol, from Step B) in i-PrOH (6.0 mL) at RT. After 20 h, the mixture was partitioned between CH$_2$Cl$_2$ (75 mL) and saturated aq. NaCl (50 mL). The aqueous layer was extracted with CH$_2$Cl$_2$ (2×75 mL). The organic layers were dried (Na$_2$SO$_4$), decanted, and evaporated to give crude (1α,5α,6α)-3-(t-butoxycarbonyl)-6-(1-hydroxy-2-nitrobutyl)-3-azabicyclo[3.1.0]hexane as 2.11 g of yellow syrup.

All of the crude (1α,5α,6α)-3-(tert-butoxycarbonyl)-6-(1-hydroxy-2-nitrobutyl)-3-azabicyclo[3.1.0]hexane was dissolved in CH$_3$CN (30 mL). 1,3-Dicyclohexylcarbodiimide (2.85 g, 13.8 mmol) and copper(I) chloride (620 mg, 6.26 mmol) were added and the mixture was stirred at RT. After 15 h, the mixture was diluted with EtOAc (200 mL) and 5 mL of 35% (w/w) oxalic acid in CH$_3$OH was added. The precipitate was removed by filtration through Celite and washed with additional EtOAc (50 mL). The filtrate was washed with saturated aq. NaHCO$_3$ (2×100 mL) followed by saturated aq. NaCl (100 mL), dried (Na$_2$SO$_4$), decanted, and evaporated. The crude product was purified by flash column chromatography on silica gel, eluting with 90:10 to 50:50 v/v hexanes/EtOAc to give the title compound as a 60:40 mixture of E- and Z-olefin isomers, respectively. For the title compound: $^1$H NMR (500 MHz, CDCl$_3$) major isomer peaks (partial data) at δ 6.59 (d, J=11, 1H), 2.51 (q, J=7, 2H), 1.90 (t, J=3, 2H), 1.41 (dt, J=11, 3, 1H), 1.48 (s, 9H), 1.18 (t, J=7, 3H); minor isomer peaks (partial data) at δ 5.14 (d, J=11, 1H), 2.56 (q, J=7, 2H), 2.22 (dt, J=11, 3, 1H), 1.74 (t, J=3, 2H), 1.46 (s, 9H), 1.11 (t, J=7, 3H).

Step D: (1α,5α,6α)-3-(tert-Butoxycarbonyl)-6-(3,5-diethyl-(1H)-pyrazol-4-yl)-3-azabicyclo[3.1.0]hexane

[Note: For safety reasons, flasks having smooth (not ground glass) joints and pipets with fire-polished tips were used for diazoalkane reactions]. 3-Nitro-1-nitroso-1-propylguanidine (1.31 g, 7.5 mmol) was added in 6–8 portions over 1 h to a stirred mixture of 40% w/w aqueous potassium hydroxide solution (2.3 mL) and Et$_2$O (10 mL) at 0° C. The mixture was stirred for 0.5 h after the last addition, and the Et$_2$O layer was then decanted using a pipet. The aqueous layer was stirred for 15 min with each of two additional 5-mL portions of Et$_2$O. The dried Et$_2$O layers, containing diazopropane, were added in succession to a solution of (1α,5α,6α)-3-(tert-butoxycarbonyl)-6-(2-nitrobut-1-enyl)-3-azabicyclo[3.1.0]hexane (0.50 g, 1.8 mmol, from Step C) in Et$_2$O (5 mL) and the solution was stored in the dark at 0° C. After 40 h, the excess diazopropane was quenched by the careful addition of acetic acid (0.30 mL). The solution was stirred at 0° C. for 15 min before being partioned between EtOAc (30 mL) and saturated aq. NaHCO$_3$ (20 mL). The organic layer was washed with saturated aq. NaCl (10 mL), and the aqueous layers were extracted in succession with EtOAc (30 mL). The EtOAc layers were dried (Na$_2$SO$_4$), decanted, and evaporated to give 652 mg of crude cycloaddition product.

A portion (596 mg) of the crude cycloaddition product was stirred for 20 min at RT with 20 mL of 2 N potassium hydroxide in 95% EtOH. The solution was then partitioned between water (100 mL) and Et$_2$O (100 mL). The organic layer was washed with saturated aq. NaCl (50 mL), and the aqueous layers were extracted in succession with Et$_2$O (50 mL). The organic layers were dried (Na$_2$SO$_4$), decanted, and evaporated to give the title compound as colorless syrup. For the title compound: $^1$H NMR (500 MHz, CD$_3$OD) δ 3.76 (d, J=11, 2H), 3.50–3.42 (m, 2H), 2.69–2.57 (m, 4H), 1.73–1.68 (m, 2H), 1.45 (s, 9H), 1.26 (t, J=3, 1H), 1.22 (t, J=7); ESI-MS 306.2 (M+H); HPLC A: 2.2 min.

Step E: (1α,5α,6α)-3-(tert-Butoxycarbonyl)-6-(3,5-diethyl-1-methyl-(1H)-pyrazol-4-yl)-3-azabicyclo[3.1.0]hexane Potassium carbonate (92 mg, 0.66 mmol) and iodomethane (0.070 mL, 0.16 g, 1.1 mmol) were added to a solution of (1α,5α,6α)-3-(tert-butoxycarbonyl)-6-(3,5-diethyl-1H-pyrazol-4-yl)-3-azabicyclo[3.1.0]hexane (100 mg, 0.33 mmol, from Step D) in CH$_3$CN (1.4 mL) and the mixture was stirred at rt. After 5 h, additional iodomethane (0.040 mL, 91 mg, 0.64 mmol) was added. After stirring overnight at RT, the mixture was added to EtOAc (20 mL) and washed with saturated aq. NH$_4$Cl (20 mL) followed by saturated aq. NaCl (20 mL). The aqueous layers were extracted in succession with EtOAc (2×20 mL). The organic layers were dried (Na$_2$SO$_4$), decanted, and evaporated. Purification of the crude product by flash column chromatography on silica gel, eluting with 80:20 to 50:50 v/v hexanes/EtOAc gave the title compound as a colorless syrup. For the title compound: $^1$H NMR (500 MHz, CDCl$_3$) δ 3.76 (d, J=11, 1H, 3.72 (s, 3H), 3.66 (d, J=11, 1H), 3.51–3.44 (m, 4H), 2.67–2.59 (m, 4H), 1.67–1.60 (m, 2H), 1.47 (s, 9H), 1.34 (t, J=3, 1H), 1.25 (t, J=7, 3H), 1.18 (t, J=7, 3H).

Step F: (1α,5α,6α)-6-(3,5-Diethyl-1-methyl-1H-pyrazol-4-yl)-3-azabicyclo[3.1.0]hexane Trifluoroacetic acid (2.0 mL) was added to a solution of (1α,5α,6α)-3-(t-butoxycarbonyl)-6-(3,5-diethyl-1-methyl-1H-pyrazol-4-yl)-3-azabicyclo[3.1.0]hexane (67 mg, 0.21 mmol, from Step E) in CH$_2$Cl$_2$ (2.0 mL). After 2 h, the reaction was concentrated and the residue was dissolved in EtOAc (30 mL) and washed with saturated aq. NaHCO$_3$ (20 mL) followed by saturated aq. NaCl (20 mL). The aqueous layers were extracted with EtOAc (2×30 mL). The organic layers were dried (Na$_2$SO$_4$), decanted, and evaporated to give the title compound as yellow syrup. For the title compound: $^1$H NMR (500 MHz, CD$_3$OD) δ 3.67 (s, 3H), 3.23 (d, J=11, 2H), 3.05 (bd, J=11, 2H), 2.69 (q, J=7), 2.58 (q, J=7, 2H), 1.71–1.67 (m, 2H), 1.44 (t, J=3, 11H), 1.20 (t, J=7, 3H), 1.17 (t, J=7, 3H); ESI-MS 220.2 (M+H). HPLC A: 0.40 min.

Bicyclic Amines 2–7

Bicyclic Amine 2 was prepared using reactions similar to those described for Bicyclic Amine 1, substituting iodoethane for iodomethane and using a mixture of potassium carbonate and cesium carbonate as the base in Step E. Bicyclic Amine 3 was prepared using the reactions similar to those described for Bicyclic Amine 1, substituting 1-iodo-2-methylpropane, sodium hydride, and DMF for iodomethane, potassium carbonate, and CH$_3$CN, respectively, and increasing the temperature to 45° C. in Step E.

Bicyclic Amines 4–7 were prepared using reactions similar to those described for Bicyclic Amine 1, substituting 1-ethyl-3-nitro-1-nitrosoguanidine for 3-nitro-1-nitroso-1-propylguanidine in Step D. In Bicyclic Amines 4 and 5, a mixture of potassium carbonate and cesium carbonate was used as the base in Step E. The isomeric products in Step E were separated by flash column chromatography prior to Step F. Bicyclic Amines 6 and 7 were prepared in a similar manner, with the substitution of iodoethane and cesium carbonate for iodomethane and potassium carbonate, respectively, in Step E.

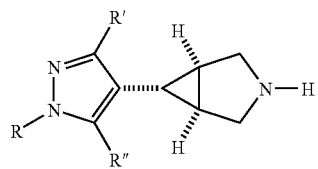

| Bicyclic Amine | R | R' | R" | ESI-MS | HPLC A |
|---|---|---|---|---|---|
| 2 | Et | Et | Et | 234.2 (M + H) | 0.48 min |
| 3 | i-Bu | Et | Et | 262.2 (M + H) | 0.99 min |
| 4 | CH$_3$ | Et | CH$_3$ | 206.1 (M + H) | 0.32 min |
| 5 | CH$_3$ | CH$_3$ | Et | 206.1 (M + H) | 0.32 min |

-continued

| Bicyclic Amine | R | R' | R" | ESI-MS | HPLC A |
|---|---|---|---|---|---|
| 6 | Et | Et | CH$_3$ | 220.2 (M + H) | 0.45 min |
| 7 | Et | CH$_3$ | Et | 220.2 (M + H) | 0.48 min |

Pyrrolidine 1

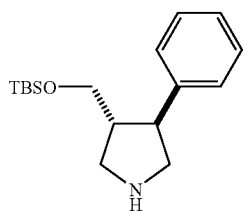

3-(R)-(tert-Butyldimethylsilyloxymethyl)-4-(S)-phenyl pyrrolidine

Step A: 3-((E)-Cinnamoyl)-4-(S)-benzyl oxazolidin-2-one

A solution of 222 g (1.5 mol) of trans-cinnamic acid and 250 mL (1.77 mol) of TEA in 3 L of THF at −78° C. was treated with 200 mL of trimethylacetyl chloride maintaining the internal temperature at less than −65° C. The resulting mixture was warmed to 0° C., then cooled to −78° C.

In a separate flask, a solution of 4-(S)-benzyl-oxazolidin-2-one in 2.05 L of THF at −20° C. was treated with 660 mL of 2.5 M n-butyllithium in hexanes over 45 min. The resulting turbid mixture was cooled to −78° C. and then transferred via cannula to the flask containing the mixed anhydride. The resulting mixture was allowed to warm to it and was stirred for 20 h. The reaction was quenched with 300 mL of sat'd NH$_4$Cl; the resulting mixture was partitioned between EtOAc and H$_2$O and the layers were separated. The organic layer was dried over MgSO$_4$. The aqueous layer was extracted with 2×EtOAc; the extracts were dried and all of the organic extracts were combined. Partial concentration in vacuo caused precipitation of a solid; the mixture was diluted with hexanes and allowed to stand at rt for 1.5 h. The precipitate was filtered and dried to afford the title compound: $^1$H NMR (500 MHz) δ 2.86 (dd, J=13.5, 9.5, 1H), (3.38, J=13.5, 3.5, 1H), 4.20–4.27 (m, 2H), 4.78–4.83 (m, 1H), 7.24–7.42 (5H), 7.63–7.65 (m, 1H), 7.92 (app d, J=2.5, 1H).

Step B: 3-(1-Benzyl-4-(S)-phenylpyrrolidine-3-(R)-carbonyl)-4-(S)-benzyl oxazolidin-2-one and 3-(1-benzyl-4-(R)-phenyl-pyrrolidine-3-(S)-carbonyl)-4-(S)-benzyl oxazolidin-2-one A solution of 402 g (1.3 mol) of 3-((E)-cinnamoyl)-4-(S)-benzyl oxazolidin-2-one (from Step A) and 474 g (2.0 mol) of N-methoxymethyl-N-trimethylsilylmethyl benzyl amine in 4 L of CH$_2$Cl$_2$ at −10° C. was treated with 6 mL of trifluoroacetic acid. The resulting mixture was stirred cold for 4 h and then was treated with an additional 4 mL of trifluoroacetic acid. The reaction mixture was warmed to rt and stirred for 20 h. The reaction was quenched with 2 L of sat'd NaHCO$_3$ and the layers were separated. The organic layer was washed with 1 L of sat'd NaCl and concentrated. Chromatography on 10 kg of silica gel using 4:1 v/v hexanes/EtOAc (24 L), then 7:3 v/v hexanes/EtOAc (36 L), then 3:2 v/v hexanes/EtOAc (32 L) afforded 3-(1-benzyl-4-(S)-phenylpyrrolidine-3-(R)-carbonyl)-4-(S)-benzyl oxazolidin-2-one and 3-(1-benzyl-4-(R)-phenylpyrrolidine-3-(S)-carbonyl)-4-(S)-benzyl oxazolidin-2-one. For 3-(1-benzyl-4-(S)-phenylpyrrolidine-3-(R)-carbonyl)-4-(S)-benzyl oxazolidin-2-one: $^1$H NMR (500 MHz) δ 2.66 (t, J=8.0, 1H), 2.78 (dd, J=13.0, 9.0, 1H), 2.87 (dd, J=9.0, 4.5, 1H), 3.21–3.27 (m, 2H), 3.64 (d, J=11.5, 1H), 3.77 (d, J=11.5, 1H), 4.10–4.15 (m, 2H), 4.61–4.65 (m, 1H), 7.16–7.38 (15H). For 3-(1-benzyl-4-(R)-phenylpyrrolidine-3-(S)-carbonyl)-4-(S)-benzyl oxazolidin-2-one: $^1$H NMR (500 MHz) δ 2.69–2.76 (m, 2H), 2.82 (dd, J=9.5, 5.5, 1H), 3.14–3.22 (3H), 3.64 (d, J=13.0, 1H), 3.74 (d, J=13.0, 1H), 4.07–4.12 (m, 2H), 4.16 (t, J=9.0, 1H), 4.26–4.30 (m, 1H), 4.65–4.69 (m, 1H), 7.03–7.40 (15H).

Step C: 1-Benzyl-3-(R)-hydroxymethyl-4-(S)-phenylpyrrolidine

A solution of 3-(1-benzyl-4-(S)-phenylpyrrolidine-3-(R)-carbonyl)-4-(S)-benzyl oxazolidin-2-one (from Step B) in 2.5 L of THF at 10° C. was treated with 1.18 L of 1.0 M lithium aluminum hydride solution in THF over a period of 2 h. The resulting mixture was warmed to rt and stirred for 20 h. The reaction was quenched by adding 40 mL of H$_2$O, then 40 mL of 2.0 N NaOH, then 115 mL of H$_2$O and then was stirred at rt for 1.5 h. The mixture was filtered and the filtrate was concentrated. Chromatography on 4 kg of silica using 4:1 hexanes/acetone (14 L), then 7:3 hexanes/acetone as the eluant to afford the title compound: $^1$H NMR (400 MHz) δ 2.38–2.46 (m, 2H), 2.78–2.88 (3H), 3.20–3.26 (2H), 3.65 (dd, J=12.0, 4.0, 1H), 3.66 (app s, 2H), 3.74 (dd, J=12.0, 4.0, 1H), 7.18–7.34 (10H); ESI-MS 268 (M+H); HPLC A: 2.35 min.

Step D: 1-Benzyl-3-(R)-(tert-Butyldimethylsilyloxymethyl)-4-(S)-phenyl pyrrolidine A solution of 82.0 g (0.31 mol) of 1-benzyl-3-(R)-hydroxymethyl-4-(S)-phenyl pyrrolidine (from Step C) and 46.5 g (0.36 mol) of N,N-diisopropylethylamine in 1 L of CH$_2$Cl$_2$ was treated with 54.2 g (0.36 mol) of tert-butyldimethylsilyl chloride and the resulting mixture was stirred at rt for 20 h. The reaction was quenched with 750 mL of sat'd NaHCO$_3$ and the layers were separated, The organic layer was combined with 150 g of silica gel and aged for 45 min. The mixture was filtered and the filtrate was concentrated to afford the title compound.

Step E: 3-(R)-(tert-Butyldimethylsilyloxymethyl)-4-(S)-phenylpyrrolidine

A mixture of 117 g (0.31 mol) of 1-benzyl-3-(R)-(tert-butyldimethylsilyloxymethyl)-4-(S)-phenyl pyrrolidine (from Step D), 31.5 g (0.50 mol) ammonium formate, 20.0 g of 20% palladium hydroxide on carbon in 1.5 L of MeOH was heated at 55° C. for 2.5 h. The mixture was cooled and filtered through a pad of Celite. The filtrate was concentrated. The residue was dissolved in 1 L of CH$_2$Cl$_2$, washed with 300 mL of 10% NH$_4$OH solution, 200 mL of sat'd NaCl, dried over MgSO$_4$ and concentrated to afford the title compound: $^1$H NMR (400 MHz) δ −0.09 (s, 3H), −0.08 (s, 3H), 0.77 (s, 9H), 2.25–2.30 (m, 1H), 2.84–2.96 (4H), 3.18 (dd, J=11.2, 3.2, 1H), 3.29–3.36 (m, 1H), 3.44 (dd, J=10.0, 6.0), 3.56 (dd, J=10.0, 4.4, 1H); ESI-MS 292 (M+H); HPLC A: 3.44 min.

Pyrrolidine 2

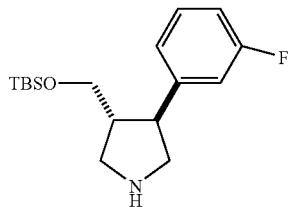

3-(R)-(tert-Butyldimethylsilyloxymethyl)-4-(S)-(3-fluoro)phenylpyrrolidine

The title compound was prepared using procedures analogous to those described to prepare Pyrrolidine 1, except that trans-(3-fluoro)cinnamic acid was substituted for trans-cinnamic acid in Step A. For the title compound: $^1$H NMR (400 MHz) δ 0.013 (s, 3H), 0.016 (s, 3H), 0.87 (s, 9H), 2.09 (br s, 1H), 2.30–2.37 (m, 1H), 2.88–2.90 (3H), 2.23 (dd, J=8.0, 11.2, 1H), 3.39 (dd, J=6.8, 10.0. 1H), 3.56 (dd, J=6.0, 10.0, 1H), 3.64 (dd, J=5.2, 10.0), 6.86–6.91 (m, 1H), 6.95 (dt, J=12.0, 2.4, 1H), 7.01 (d, J=7.6, 1H), 7.22–7.27 (m, 1H); ESI-MS 310 (M+H); HPLC A: 3.05 min.

EXAMPLE 1

3-{[(3S,4S)-3-[(4-{1,3-Diethyl-4-methyl-(1H)-pyrazol-5-yl}piperidin-1-yl)methy]-4-(3-fluorophenyl)pyrrolidin-1-yl]methyl}-bicyclo[3.1.0]hexane)-3-endo-carboxylic acid Step A: 1-Benzyl-3-(R)-formyl-4-(S)-(3-fluorophenyl)pyrrolidine The title compound was prepared from 1-benzyl-3-(R)-hydroxymethyl-4-(S)-(3-fluorophenyl)pyrrolidine (from Pyrrolidine 2, Step C) using a procedure analogous to that described in Example 2, Step C.

Step B: 1-Benzyl-3-{[(3S,4S)-3-[(4-{1,3-diethyl-4-methyl-(1H)-pyrazol-5-yl}piperidin-1-yl)methyl]-4-(3-fluorophenyl)pyrrolidine A solution of 2.83 g (10.0 mmol) of 1-benzyl-3-(R)-formyl-4-(S)-(3-fluorophenyl)pyrrolidine (from Example 1, Step A), 2.94 g (10.0 mmol) of Piperidine 8, 2.80 mL (20.0 mmol) of triethylamine and 4.24 g (20.0 mmol) of sodium triacetoxyborohydride in 75 mL of acetonitrile was stirred at rt for 2 h. The mixture was concentrated. The residue was partitioned between 300 mL of ether and 100 mL of 1.0 N NaOH and the layers were separated. The organic layer was dried over MgSO$_4$ and concentrated. Flash chromatography on 150 g of silica gel using 40:1:0.1 v/v/v CH$_2$Cl$_2$/MeOH/NH$_4$OH as the eluant afforded the title compound. $^1$H NMR (400 MHz) δ 1.21 (t, J=7.2, 3H), 1.34 (t, J=6.8, 3H), 1.47–1.54 (m, 1H), 1.60–1.68 (m, 1H), 1.77–1.85 (3H), 1.96–2.01 (2H), 2.03 (s, 3H), 2.41–2.57 (7H), 2.66–2.74 (2H), 2.93–3.05 (4H), 3.68 (q, J=13.2, 2H), 4.05 (q, J=7.2, 2H), 6.85–7.40 (9H); ESI-MS 489 (M+H); LC-1: 1.87 min.

Step C: 3-{[(3S,4S)-3-[(4-{1,3-Diethyl-4-methyl-(1H)-pyrazol-5-yl}piperidin-1-yl)methyl]-4-(3-fluorophenyl)pyrrolidine A mixture of 4.65 g (9.5 mmol) of 1-benzyl-3-{[(3S,4S)-3-[(4-{1,3-diethyl-4-methyl-1H-pyrazol-5-yl}piperidin-1-yl)methyl]-4-(3-fluorophenyl) pyrrolidine (from Example 1, Step B), 6.30 g (0.1 mol) of ammonium formate and 1.00 g of 20% palladium hydroxide on carbon in 50 mL of MeOH was heated at 65° C. After 1 h, second portions of ammonium formate and catalyst were added and stirring was continued for 20 min. The mixture was cooled and filtered through a pad of Celite. The filtrate was concentrated. The residue was partitioned between 150 mL of CH$_2$Cl$_2$ and 100 mL of 30% aqueous NH$_4$OH and the layers were separated. The organic layer was dried over MgSO$_4$. The aqueous layer was extracted with 2×150 mL of CH$_2$Cl$_2$; the extracts were dried and all of the extracts were combined and concentrated. Flash chromatography on 125 g of silica gel using CH$_2$Cl$_2$, then 20:1:0.1 v/v CH$_2$Cl$_2$/MeOH/NH$_4$OH as the eluant afforded the title compound. ESI-MS 399 (M+H); LC-1: 1.41 min.

Step D: 3-{[(3S,4S)-3-[(4-{1,3-Diethyl-4-methyl-1H-pyrazol-5-yl}piperidin-1-yl)methyl]-4-(3-fluorophenyl)pyrrolidin-1-yl]methyl}-bicyclo[3.1.0]hexane)-3-endo-carboxylic acid, benzyl ester A solution of 100 mg (0.25 mmol) of 3-{[(3S,4S)-3-[(4-{1,3-diethyl-4-methyl-1H-pyrazol-5-yl}piperidin-1-yl)methyl]-4-(3-fluorophenyl)pyrrolidine (from Example 1, Step C) and 61 mg (0.24 mmol) of 3-(3-formyl-bicyclo[3.1.0]hexane)-endo-carboxylic acid, benzyl ester (Prepared as Aldehyde 9 above) in 2 mL of CH$_2$Cl$_2$ was treated with 80 mg (0.37 mmol) of sodium triacetoxyborohydride. After 45 minutes at rt the reaction was partitioned between 50 mL of CH$_2$Cl$_2$ and 50 mL of 1 N NaHCO$_3$ and the layers were separated. The aqueous layer was extracted with 50 mL of CH$_2$Cl$_2$. The combined organic phases were washed with 100 mL of brine, dried over Na$_2$SO$_4$ and concentrated. The residue was purified by flash chromatography using 9:1 v/v of hexanes/acetone as the eluant to afford the title compound as a white foam: R$_F$: 0.33 (4:1 v/v hexanes/acetone); $^1$H-NMR (500 MHz) δ −0.02 (m, 1H), 0.37 (m, 1H), 1.21 (t, J=7.6, 3H), 1.24–1.31 (m, 2H), 1.34 (t, J=7.2, 3H), 1.52–2.01 (m, 8H), 2.04 (s, 3H), 2.25–2.32 (m, 4H), 2.53–2.92 (m, 13H), 4.06 (q, J=7.2, 2H), 5.16 (ABq, J=12.4, 2H), 6.85 (m, 1H), 7.02–7.06 (m, 2H), 7.19 (m, 1H), 7.27–7.39 (m, 5H).

Step E: 3-{[(3S,4S)-3-[(4-{1,3-Diethyl-4-methyl-1H-pyrazol-5-yl}piperidin-1-yl)methyl]-4-(3-fluorophenyl)pyrrolidin-1-yl]methyl}-bicyclo[3.1.0]hexane)-3-endo-carboxylic acid A mixture of 139 mg (0.22 mmol) of 3-{[(3S,4S)-3-[(4-{1,3-diethyl-4-methyl-1H-pyrazol-5-yl}piperidin-1-yl)methyl]-4-(3-fluorophenyl)pyrrolidin-1-yl]methyl}-bicyclo [3.1.0]hexane)-3-endo-carboxylic acid, benzyl ester (from Example 1, Step D) and 36 mg of 10% palladium on carbon in 3 mL of MeOH was hydrogenated at rt under a balloon of hydrogen for 1.25 hours. The reaction was filtered and concentrated. The residue was purified by flash chromatography using a gradient of 98/2 v/v CH$_2$Cl$_2$/MeOH and 90:10:1/v/v CH$_2$Cl$_2$/MeOH/NH$_4$OH as the gradient to afford the title compound: R$_F$: 0.42 (90:10:1 v/v CH$_2$Cl$_2$/MeOH/NH$_4$OH); $^1$H-NMR (500 MHz, CD$_3$OD) δ 0.37–0.42 (m, 2H), 1.13 (t, J=7.6, 3H), 1.25 (t, J=7.2, 3H), 1.29–1.31 (m, 2H), 1.53 (m, 1H), 1.62 (m, 1H), 1.76–1.85 (m, 3H), 1.95–2.07 (m, 6H), 2.45–2.84 (m, 9H), 3.01 (m, 1H), 3.16–3.30 (m, 5H), 3.57–3.64 (m, 2H), 4.01 (q, J=7.2, 2H), 6.97 (m, 1H), 7.17–7.20 (m, 2H), 7.34 (m, 1H); ESI-MS 537.4 (M+H); HPLC LC 2: 1.84 min.

EXAMPLE 2

1-{[(3S,4S)-3-{[4-(2-Ethyl-4,5,6,7-tetrahydropyrazolo[1,5-a]pyridin-3-yl)piperidin-1-yl]methyl}-4-(3-fluorophenyl)pyrrolidin-1-yl]methyl}cyclohexanecarboxylic acid Step A: 1-{[(3R,4S)-3-(tert-Butyldimethylsilyloxymethyl)4-(3-fluorophenyl)pyrrolidin-1-yl]methyl}cyclohexanecarboxylic acid, benzyl ester A solution of 8.3 g (26.9 mmol) 3-(R)-(tert-butyldimethylsilyloxymethyl)-4-(S)-(3-fluoro)phenylpyrrolidine (Prepared as Pyrrolidine 2 above) in 100 mL of $CH_2Cl_2$ and 6.0 g (24.4 mmol) of 1-formyl-cyclohexane carboxylic acid, benzyl ester (Prepared as Aldehyde 4 above) at 0° C. was treated with 7.8 g (36.7 mmol) of sodium triacetoxyborohydride. The resulting mixture was warmed to rt and stirred for 20 h. The reaction was partitioned between 200 mL EtOAc and 100 mL of saturated $NaHCO_3$ and the layers were separated. The organic layer was dried over $MgSO_4$. The mixture was filtered and the filtrate was concentrated. Purification by Biotage Flash 40 using a 40 M cartridge and 95:5 hexanes/ethyl acetate (1 L) as the eluant to afford the title compound: $^1$H NMR (500 MHz, CDCl3) δ 0.00–0.01 (6H), 0.86 (s, 9H), 1.24–3.54 (20H), 5.14 (ABq, J=12.3, 2H), 6.83–7.38 (9H).

Step B: 1-{[(3R,4S)-3-(Hydroxymethyl)-4-(3-fluorophenyl)pyrrolidin-1-yl]methyl}cyclohexanecarboxylic acid, benzyl ester A solution of 8.1 g (15.0 mmol) 1-{[(3R,4S)-3-(tert-butyldimethylsilyloxymethyl)-4-(3-fluorophenyl)pyrrolidin-1-yl]methyl}cyclohexanecarboxylic acid, benzyl ester (from Step A) in 150 mL of THF at 0° C. was treated with 45 mL of 1.0 M tetrabutylammonium fluoride solution in THF. The resulting mixture was warmed to rt and stirred for 20 h. The reaction mixture was partitioned between 200 mL of ether and 100 mL of 50% sat'd $NaHCO_3$ and the layers were separated. The organic layer was dried over $MgSO_4$ and concentrated. Purification by Biotage Flash 40 using a 40 M cartridge and 0.5 L to 1.0 L of 9:1 to 2:1 v/v hexane/ethyl acetate as the eluant afforded the title compound: $^1$H NMR (500 MHz, CDCl3) δ 1.23–3.68 (20H), 5.18 (ABq, J=12.3, 2H), 6.88–7.01 (3H), 7.21–7.40 (6H).

Step C: 1-{[(3R,4S)-3-Formyl-4-(3-fluorophenyl)pyrrolidin-1-yl]methyl}cyclohexanecarboxylic acid, benzyl ester A solution of 2.1 mL (24.2 mmol) of oxalyl chloride in 110 mL of $CH_2Cl_2$ at –78° C. was treated with 2.6 mL (36.8 mmol) of DMSO maintaining the temperature at less than –60° C. The resulting mixture was stirred cold for 5 min. A solution of 4.5 g (10.5 mmol) of 1-{[(3R,4S)-3-(hydroxymethyl)-4-(3-fluorophenyl)pyrrolidin-1-yl]methyl}cyclohexanecarboxylic acid, benzyl ester (from Step B) in 10 mL of $CH_2Cl_2$ was added maintaining the temperature at less than –60° C. The resulting mixture was stirred cold for 60 min. The mixture was treated with 15 mL (84.0 mmol) of N,N-diisopropylethylamine maintaining the temperature at less than –60° C. The reaction was warmed to 0° C., stirred for 20 min and quenched with 20 mL 0.5 $\underline{N}$ $KHSO_4$. The mixture was partitioned between 250 mL of $CH_2Cl_2$ and 100 mL of $H_2O$ and the layers were separated. The aqueous layer was extracted with 250 mL of $CH_2Cl_2$. The combined organic phases were dried over $MgSO_4$ and concentrated. Purification by Biotage Flash 40 using a 40 M cartridge and 1.0 L each of 95:5 to 90:10 v/v hexane/ethyl acetate as the eluant afforded the title compound: $^1$H NMR (500 MHz, CDCl3) δ 1.24–3.48 (18H), 5.16 (ABq, J=12.2, 2H), 6.90–7.02 (3H), 7.22–7.39 (6H), 9.59 (s, 1H).

Step D: 1-{[(3S,4S)-3-[{4-(2-Ethyl-4,5,6,7-tetrahydropyrazolo[1,5-a]pyridin-3-yl)piperidin-1-yl]methyl}-4-(3-fluorophenyl)pyrrolidin-1-yl]methyl}cyclohexanecarboxylic acid, benzyl ester The title compound was prepared from 1-{[(3R,4S)-3-formyl-4-(3-fluorophenyl)pyrrolidin-1-yl]methyl}cyclohexanecarboxylic acid, benzyl ester (from Step C) and 4-(2-ethyl-4,5,6,7-tetrahydropyrazolo[1,5-a]pyridin-3-yl)-piperidine, hydrochloride salt (Prepared as Piperidine 9 above) using a procedure analogous to that described in Example 1, Step D. $^1$H NMR (500 MHz, CDCl3) δ 1.22 (t, 3H, J=7.6 Hz), 1.23–1.50 (m, 6H), 1.50–1.70 (br m, 5H), 1.70–2.00 (m, 8H), 2.17 (br d, 2H, J=12.3 Hz), 2.20–2.40 (m, 5H), 2.57 (q, 2H, J=7.3), 2.61–2.96 (m, 9H), 4.07 (t, 2H, J=6.0 Hz), 5.16 (m, 2H), 6.85 (dt, 1H, J=1.8, 8.5 Hz), 7.02–7.10 (m, 2H), 7.20 (q, 1H, J=6.5 Hz), 7.25–7.40 (m, 5H).

Step E: 1-{[(3S,4S)-3-{[4-(2-Ethyl-4,5,6,7-tetrahydropyrazolo[1,5-a]pyridin-3-yl)piperidin-1-yl]methyl}-4-(3-fluorophenyl)pyrrolidin-1-yl]methyl}cyclohexanecarboxylic acid The title compound was prepared from 1-{[(3S,4S)-3-{[4-(2-ethyl-4,5,6,7-tetrahydropyrazolo[1,5-a]pyridin-3-yl)piperidin-1-yl]methyl}-4-(3-fluorophenyl)pyrrolidin-1-yl]methyl}cyclohexanecarboxylic acid, benzyl ester (from Step D) using a procedure analogous to that described in Example 1, Step E. $^1$H NMR (500 MHz, $CD_3OD$) δ 1.14 (t, 3H, J=7.5 Hz), 1.30–1.90 (m, 15H), 1.90–2.10 (m, 6H), 2.35–2.45 (m, 1H), 2.45–2.60 (4H), 2.65–2.80 (m, 3H), 2.85 (d, 1H, J=11.9 Hz), 3.01 (d, 1H, J=11.1 Hz), 3.10–3.25 (m, 4H), 3.59–3.64 (m, 2H), 3.97 (t, 2H, 6.1 Hz), 6.98–7.02 (m, 1H), 7.16–7.20 (m, 2H), 7.34–7.38 (m, 1H). ESI-MS 551 (M+H); HPLC A 1.68 min.

EXAMPLE 3

1-{[(3S,4S)-3-{[(1,3-Diethyl-5-methyl-(1H)-pyrazol-4-yl)piperidin-1-yl]methyl}-4-(3-fluorophenyl)pyrrolidin-1-yl]methyl}cyclohexanecarboxylic acid Step A: 1-{[(3S,4S)-3-{[(1,3-Diethyl-5-methyl-(1H)-pyrazol-4-yl)piperidin-1-yl]methyl}-4-(3-fluorophenyl)pyrrolidin 1-yl]methyl}cyclohexanecarboxylic acid, benzyl ester The title compound was prepared from 1-{[(3R,4S)-3-formyl-4-(3-fluorophenyl)pyrrolidin-1-yl]methyl}cyclohexanecarboxylic acid, benzyl ester (from Example 2, Step C) and 4-(1,3-Diethyl-5-methyl-(1H)-pyrazol-4-yl)piperidine, hydrochloride salt (Prepared as Piperidine 10 above) using a procedure analogous to that described in Example 1, Step D. $^1$H NMR (500 MHz, CDCl3) δ 1.21 (t, 3H, J=7.6 Hz), 1.26–1.35 (m, 3H), 1.36 (t, 3H, J=7.3 Hz), 1.38–1.48 (m, 3H), 1.55–1.90 (m, 7H), 1.93 (dt, 1H, J=1.6, 11.1 Hz), 2.17 (br d, 2H, J=13.7 Hz), 2.22 (s, 3H), 2.28–2.39 (m, 5H), 2.59 (q, 2H, J=7.5 Hz), 2.63–2.70 (m, 4H), 2.83–2.93 (m, 3H), 2.95 (t, 1H, J=7.1 Hz), 4.02 (q, 2H, J=7.3 Hz), 5.17 (m, 2H), 6.85 (dt, 1H, J=2.3, 8.5 Hz), 7.05–7.09 (m, 2H), 7.20 (q, 1H, J=6.2 Hz), 7.28–7.39 (m, 5H).

Step B: 1-{[(3S,4S)-3-{[(1,3-Diethyl-5-methyl-(1H)-pyrazol-4-yl)piperidin-1-yl]methyl}-4-(3-fluorophenyl)pyrrolidin-1-yl]methyl}cyclohexanecarboxylic acid The title compound was prepared from 1-{[(3S,4S)-3-{[(1,3-diethyl-5-methyl-(1H)-pyrazol-4-yl)piperidin-1-yl]methyl}-4-(3-fluorophenyl)pyrrolidin-1-yl]methyl}cyclohexanecarboxylic acid, benzyl ester (from Step A) using a procedure analogous to that described in Example 1, Step G. ¹H NMR (500 MHz, CD₃OD) δ 1.14 (t, 3H, J=7.5 Hz), 1.28 (t, 3H, J=7.1 Hz), 1.28–2.15 (m, 17H), 2.21 (s, 3H), 2.30–2.61 (m, 5H), 2.68–2.80 (m, 1H), 2.86 (d, 1H, J=10.7 Hz), 3.02 (d, 1H, J=10.3 Hz), 3.10–3.30 (m, 4H), 3.64 (m, 2H), 4.00 (q, 2H, J=7.1 Hz), 7.00 (m, 1H), 7.17–7.21 (m, 2H), 7.36 (m, 1H). ESI-MS 539 (M+H); HPLC A 1.65 min.

EXAMPLES 4–5

Examples 4–5 were prepared using procedures analogous to those described in Examples 1 and 2 using Aldehyde 1 or 2 and the appropriate piperidine.

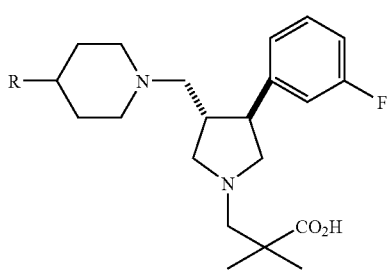

| EXAMPLE # | R | HPLC Method | HPLC RT (min) | ESI-MS (M + H) |
|---|---|---|---|---|
| 4 | 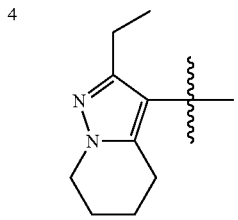 | LC-1 | 1.36 | 511.5 |

¹H NMR(500 MHz, CDCl₃) δ 1.19–3.35(36H), 4.04–4.07(2H), 6.90–7.34(4H)

| 5 | 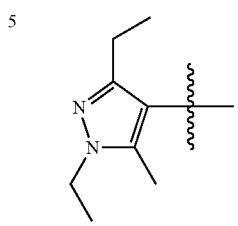 | | | |

¹HNMR(500 MHz, CD₃OD) δ 1.14(t, J=7.6, 3H), 1.23–1.29(m, 9H), 1.48–1.58(m, 2H), 1.69–1.88(m, 2H), 1.96–2.08(m, 2H), 2.21(s, 3H), 2.36–2.59(m, 5H), 2.78–2.89(m, 2H), 3.00–3.02(m, 1H), 3.16–3.39(m, 5H), 3.69–3.73(m, 2H), 3.99(q, J=7.2, 2H), 7.00–7.03(m, 1H), 7.18–7.22(m, 2H), 7.35–7.40(m, 1H)

EXAMPLES 6–9

Examples 6–9 were prepared using procedures analogous to those described in Examples 1 and 2 using Aldehyde 3 and the appropriate piperidine.

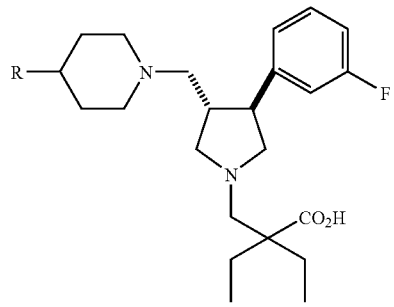

| EXAMPLE # | R | HPLC Method | HPLC RT (min) | ESI-MS (M + H) |
|---|---|---|---|---|
| 6 | 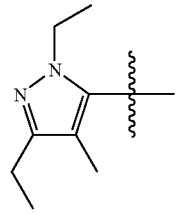 | LC-1 | 1.5 | 527.5 |

¹HNMR (500 MHz, CD₃OD) δ 0.88–0.93(m, 6H), 1.13(t, J=7.7, 3H), 1.22–1.29(m, 4H), 1.54–1.56(m, 1H), 1.61–1.75(m, 4H),1.79–1.86(m, 1H), 1.93–2.07(m, 6H), 2.43–2.56(m, 4H), 2.63–2.68(m, 1H), 2.75–2.85(m, 2H), 3.01–3.02(m, 1H), 3.19–3.37(m, 5H), 3.64–3.69(m, 2H), 4.02(q, J=7.2, 2H), 6.99–7.03(m, 1H), 7.17–7.22(m, 2H), 7.35–7.39(m, 1H)

| 7 | 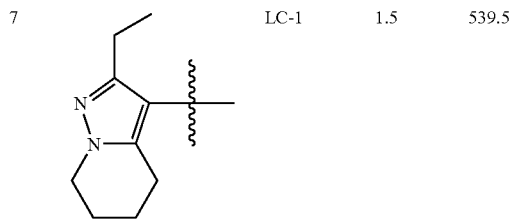 | LC-1 | 1.5 | 539.5 |

¹H NMR(500 MHz, CD₃OD) δ 0.88–0.93(m, 6H), 1.14(t, J=7.6, 3H), 1.49–1.51(m, 1H), 1.57–1.74(m, 6H), 1.79–1.85(m, 3H), 1.95–2.08(m, 4H), 2.36–2.41(m, 1H), 2.44–2.58(m, 4H), 2.71–2.78(m, 3H), 2.82–2.85(m, 1H), 2.99–3.01(m, 1H), 3.19–3.34(m, 5H), 3.62–3.66(m, 2H), 3.97(t, J=6.2, 2H), 6.98–7.02(m, 1H), 7.17–7.21(m, 2H), 7.34–7.39(m, 1H)

-continued

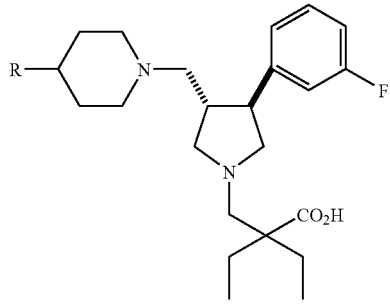

| EXAMPLE # | R | HPLC Method | HPLC RT (min) | ESI-MS (M + H) |
|---|---|---|---|---|
| 8 | 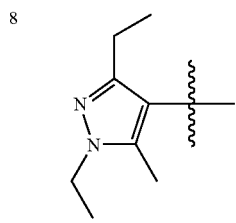 | LC-1 | 1.5 | 527.5 |

$^1$H NMR(500 MHz, CD$_3$OD) δ 0.88–0.93(m, 6H), 1.14(t, J=7.6, 3H), 1.28(t, J=7.2, 3H), 1.49–1.52(m, 1H), 1.57–1.75(m, 6H), 1.83–1.87(m, 1H), 1.97–2.10(m, 2H), 2.21(s, 3H), 2.37–2.59(m, 5H), 2.74–2.78(m, 1H), 2.84–2.86(m, 1H), 3.01–3.03(m, 1H), 3.19–3.34(m, 5H), 3.63–3.66(m, 2H), 4.00(q, J=7.2, 2H), 6.99–7.03(m, 1H), 7.17–7.21(m, 2H), 7.35–7.39(m, 1H)

-continued

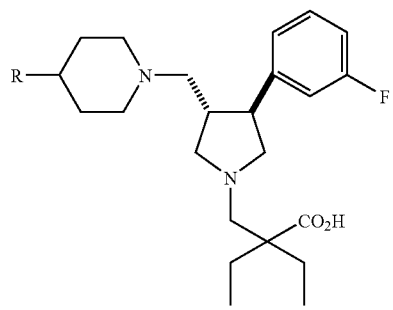

| EXAMPLE # | R | HPLC Method | HPLC RT (min) | ESI-MS (M + H) |
|---|---|---|---|---|
| 9 | 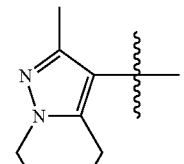 | LC-1 | 1.63 | 527.6 |

EXAMPLES 10–14

Examples 10–14 were prepared using procedures analogous to those described in Examples 1 and 2 using Aldehyde 5 and the appropriate piperidine. Racemic analogs were prepared using procedures analogous to those described in Example 1 substituting the appropriate Piperidine and Aldehyde. The intermediates required in Step B were prepared from the appropriate commercially available substituted benzaldeydes in a three step sequence: 1. Wittig reaction with N-methoxy-N-methyl-2-(triphenylphosphoranylidene) acetamide in toluene; 2. Azomethine ylide cyclization using a procedure analogous to that descibed in Pyrroldine 1, Step B; 3. DIBAL-H reduction (CH$_2$Cl$_2$, −78° C.).

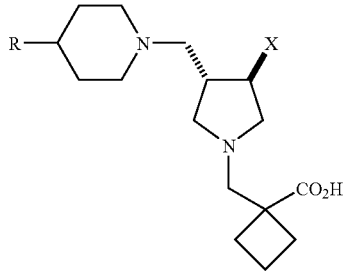

| Example # | R | X | HPLC Method | HPLC RT (min) | ESI-MS (M + H) |
|---|---|---|---|---|---|
| 10 | 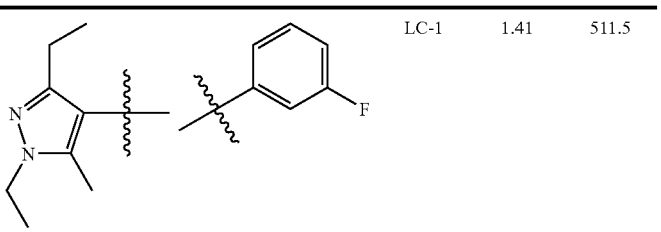 | | LC-1 | 1.41 | 511.5 |

-continued
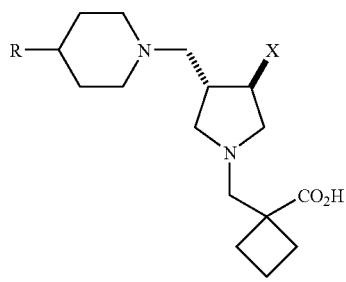
| Example # | R | X | HPLC Method | HPLC RT (min) | ESI-MS (M + H) |
|---|---|---|---|---|---|
| 11 | ethyl-methyl-pyrazole | 3-fluorophenyl | LC-1 | 1.41 | 511.5 |
| 12 | ethyl-tetrahydropyrazolopyridine | 3-fluorophenyl | LC-1 | 1.28 | 523.5 |
¹H NMR(500 MHz, CDCl₃) δ 0.87–3.31(36H), 4.04–4.07(2H), 6.91–7.30(4H)
| 13 (+/−) | ethyl-tetrahydropyrazolopyridine | 3,5-difluorophenyl | LC-1 | 1.41 | 541.5 |
| 14 (+/−) | ethyl-tetrahydropyrazolopyridine | 3,4-difluorophenyl | LC-1 | 1.47 | 541.5 |
¹H NMR(500 MHz, CDCl₃) δ 0.86–3.28(36H), 4.05–4.07(2H), 6.98–7.15(3H)

EXAMPLES 15–23
Examples 15–23 were prepared using procedures analogous to those described in Examples 1 and 2 using Aldehyde 6 and the appropriate piperidine.
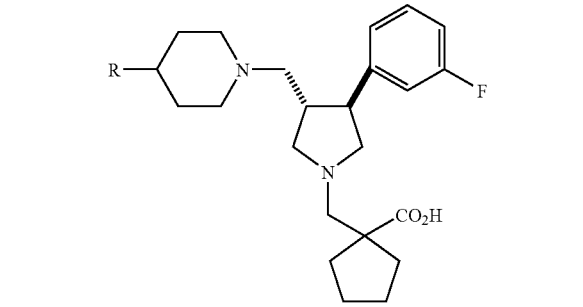
| EXAMPLE # | R | HPLC Method | HPLC RT (min) | ESI-MS (M + H) |
|---|---|---|---|---|
| 15 | 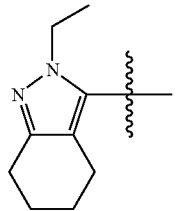 | LC-1 | 1.81 | 537.4 |
$^1$H NMR(500 MHz, CDCl$_3$) δ 1.26–3.37(38H), 4.01(q, J=7.4 Hz, 2H), 6.92–7.31(4H)
| 16 | 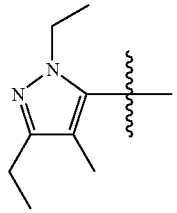 | LC-1 | 1.97 | 525.3 |
$^1$H NMR(500 MHz, CDCl$_3$) δ 0.87–3.37(40H), 4.02 (q, J=7.4, 2H), 6.91–7.33(4H)
| 17 | 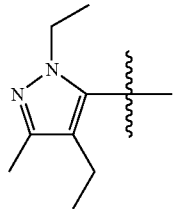 | LC-1 | 1.76 | 525.2 |
| 18 | 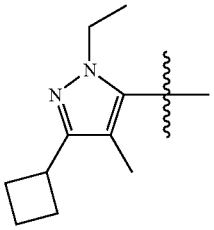 | LC-1 | 2.00 | 551.5 |
-continued
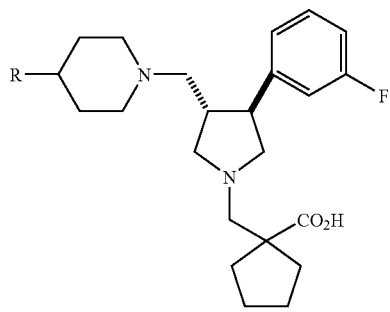
| EXAMPLE # | R | HPLC Method | HPLC RT (min) | ESI-MS (M + H) |
|---|---|---|---|---|
| 19 | 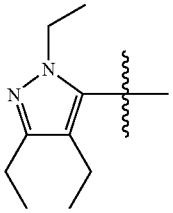 | LC-1 | 1.65 | 539.5 |
$^1$H NMR(500 MHz, CDCl$_3$) δ 1.06–3.38(40H), 4.03(q, J=7.1, 14.4 Hz, 2H), 6.91–7.31(4H)
| 20 | 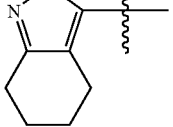 | LC-2 | 2.35 | 522.71 |
| 21 | 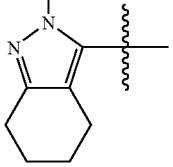 | LC-2 | 2.64 | 591.3 |
| 22 | 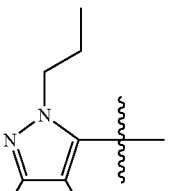 | LC-1 | 1.7 | 551.5 |
| 23 | 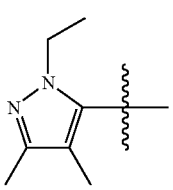 | LC-1 | 1.60 | 511.3 |

EXAMPLES 24–47
Examples 24–47 were prepared using procedures analogous to those described in Examples 1 and 2 using Aldehyde 4 and the appropriate piperidine.
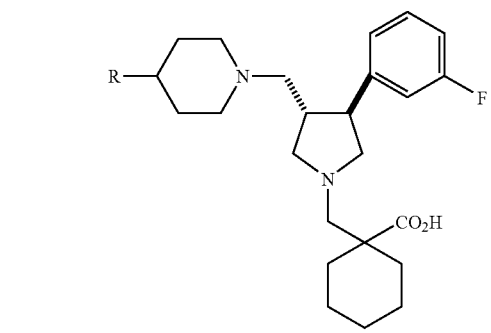
| EXAMPLE # | R | HPLC Method | HPLC RT (min) | ESI-MS (M + H) |
|---|---|---|---|---|
| 24 | 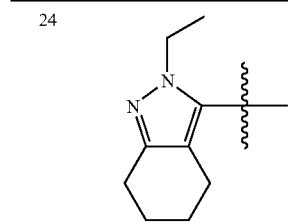 | LC-1 | 1.81 | 551.4 |
$^1$H NMR(500 MHz, CDCl$_3$) δ 0.87–3.37(40H), 4.01(q, J=7.4 Hz, 2H), 6.91–7.31(4H)
| 25 | | LC-1 | 2.32 | 569.3 |
| 26 | | LC-1 | 2.16 | 539.4 |
$^1$H NMR (500 MHz, CDCl$_3$) δ 0.87–3.37(40H), 4.02(q, J=7.4 Hz, 2H), 6.90–7.30(4H)
| 27 | | LC-1 | 1.76 | 601.3 |
-continued
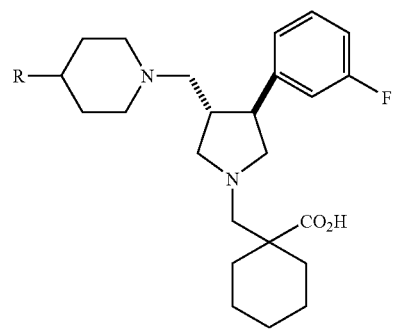
| EXAMPLE # | R | HPLC Method | HPLC RT (min) | ESI-MS (M + H) |
|---|---|---|---|---|
| 28 | 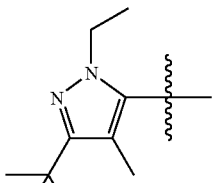 | LC-1 | 1.84 | 567.5 |
| 29 | 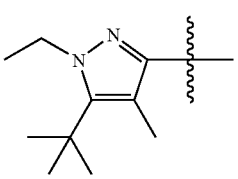 | LC-1 | 2.32 | 567.5 |
| 30 | 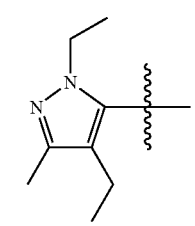 | LC-1 | 1.79 | 539.4 |
| 31 | 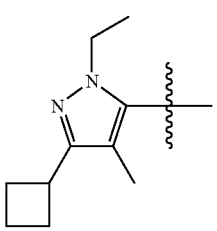 | LC-1 | 2.11 | 565.5 |
| 32 | 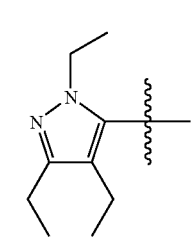 | LC-1 | 1.73 | 553.6 |

-continued

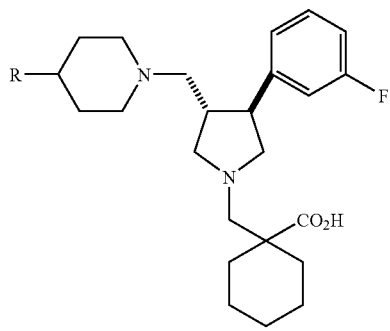

| EXAMPLE # | R | HPLC Method | HPLC RT (min) | ESI-MS (M + H) |
|---|---|---|---|---|
| 33 | (1-ethyl-3-isopropyl-4-methyl-pyrazol-5-yl) | LC-1 | 1.73 | 553.6 |
| 34 | (2-(2,2,2-trifluoroethyl)-4,5,6,7-tetrahydro-2H-indazol-3-yl) | LC-2 | 2.28 | 605.4 |
| 35 | (2-methyl-4,5,6,7-tetrahydro-2H-indazol-3-yl) | LC-2 | 2.65 | 537.5 |
| 36 | (2-propyl-4,5,6,7-tetrahydro-2H-indazol-3-yl) | LC-1 | 1.8 | 565.5 |
| 37 | (1-ethyl-4-methoxy-3-methyl-pyrazol-5-yl) | LC-1 | 1.7 | 541.4 |

-continued

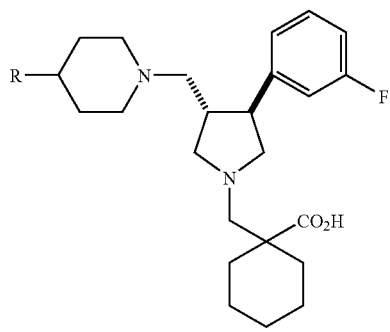

| EXAMPLE # | R | HPLC Method | HPLC RT (min) | ESI-MS (M + H) |
|---|---|---|---|---|
| 38 | (1-ethyl-3-methoxy-4-methyl-pyrazol-5-yl) | LC-2 | 2.0 | 541.5 |
| 39 | (1,3-dimethoxy-4-methyl-pyrazol-5-yl) | LG-1 | 1.8 | 541.5 |

$^1$ H NMR(500 MHz, CD$_3$OD) δ 1.25(t, J=7.2, 3H), 1.33–1.66(m, 10H), 1.89–2.06(m, 5H), 2.12(s, 3H), 2.12–2.17(m, 1H), 2.30–2.35(m,1H), 2.46–2.50(m, 1H), 260–2.64(m, 1H), 2.70–2.74(m, 1H), 2.87–2.90(m, 1H), 3.03–3.05(m, 1H), 3.11–3.31(m, 5H), 3.56–3.60 (m, 2H), 3.80(s, 3H), 3.91(q, J=7.2, 2H), 7.0–7.02 (m, 1H), 7.15–7.19(m, 2H), 7.34–7.38(m, 1H)

| | | | | |
|---|---|---|---|---|
| 40 | (2-ethyl-4,5,6,7-tetrahydro-2H-pyrano[4,3-c]pyrazol-3-yl) | LC-1 | 1.81 | 553.5 |
| 41 | (1-ethyl-3,4-dimethyl-pyrazol-5-yl) | LC-1 | 1.73 | 525.3 |
| 42 | (3-cyclopropyl-1-ethyl-4-methyl-pyrazol-5-yl) | LC-1 | 2.05 | 551.5 |

113
-continued

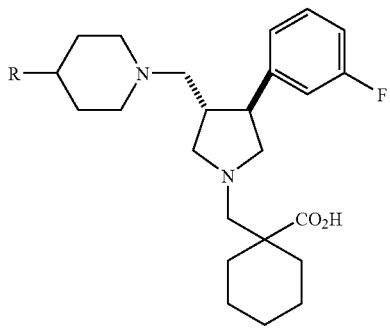

| EXAMPLE # | R | HPLC Method | HPLC RT (min) | ESI-MS (M + H) |
|---|---|---|---|---|
| 43 | (ethyl-cyclopenta-pyrazolyl) | LC-1 | 1.65 | 537.4 |
| 44 | (methoxy-ethyl-methyl-pyrazolyl) | LC-1 | 1.55 | 541.5 |
| 45 | (ethyl-hydroxymethyl-methyl-pyrazolyl) | LC-1 | 1.49 | 541.5 |
| 46 | (ethyl-methoxymethyl-methyl-pyrazolyl) | LC-1 | 1.71 | 555.5 |
| 47 | (methoxy-tetrahydropyrazolopyridinyl) | LC-1 | 1.79 | 553.7 |

$^1$H NMR(500 MHz, CD$_3$OD) δ 1.33–1.65(m, 10H), 1.76–2.14(m, 10H), 2.31(m, 1H), 2.46(m, 1H), 2.58–2.63(m, 3H), 2.71(m, 1H), 2.86(m, 1H), 3.02(m, 1H), 3.11–3.31(m, 5H), 3.55–3.60(m, 2H), 3.78(s, 3H), 3.84–3.86(m, 2H), 6.99(m, 1H), 7.14–7.19(m, 2H), 7.35(m, 1H)

EXAMPLES 48–51

Examples 48–51 were prepared using procedures analogous to those described in Examples 1 and 2 using Aldehyde 4, Piperidine 8 and the appropriate pyrrolidine. Racemic analogs were prepared using procedures analogous to those described in Example 1 substituting the appropriate Piperidine and Aldehyde. The intermediates required in Step B were prepared from the appropriate commercially available substituted benzaldeydes in a three step sequence: 1. Wittig reaction with N-methoxy-N-methyl-2-(triphenylphosphoranylidene) acetamide in toluene; 2. Azomethine ylide cyclization using a procedure analogous to that descibed in Pyrroldine 1, Step B; 3. DIBAL-H reduction (CH$_2$Cl$_2$, −78° C.).

| EXAMPLE # | X | HPLC Method | HPLC RT (min) | ESI-MS (M + H) |
|---|---|---|---|---|
| 48 (+/−) | 3-CF$_3$-phenyl | LC-1 | 1.92 | 589.5 |
| 49 (+/−) | 3,5-difluorophenyl | LC-1 | 1.55 | 557.6 |
| 50 (+/−) | 3,4-difluorophenyl | LC-1 | 1.55 | 557.6 |
| 51 (+/−) | 3-CH$_3$-phenyl | LC-1 | 1.76 | 535.6 |

EXAMPLE 52

Example 52 was prepared using procedures analogous to those described in Examples 1 and 2 using Aldehyde 7, Pyrrolidine 2 and Piperidine 8.

| EXAMPLE # | HPLC Method | HPLC RT (min) | ESI-MS (M + H) |
|---|---|---|---|
| 52 | LC-1 | 1.28 | 541.5 |

$^1$H NMR(500 MHz, CDCl$_3$) δ 1.17–3.83(36H), 4.02(q, J=7.1 Hz, 2H), 6.91–7.30(4H)

EXAMPLES 53–54

Examples 53–54 were prepared using procedures analogous to those described in Example 1 using Aldehyde 9 and the appropriate piperidine. Diastereomerically pure Example 53 was prepared using analogous procedures to those described for Pyrrolidines 1 and 2.

| EXAMPLE # | R | X | HPLC Method | HPLC RT (min) | ESI-MS (M + H) |
|---|---|---|---|---|---|
| 53 | | F | LC-1 | 1.60 | 567.6 |

$^1$H NMR(500 MHz, CDCl$_3$) δ 0.36–3.27(38H), 4.04–4.07(2H), 6.62–6.89(3H)

| EXAMPLE # | R | X | HPLC Method | HPLC RT (min) | ESI-MS (M + H) |
|---|---|---|---|---|---|
| 54 | | H | LC-1 | 1.6 | 537.5 |

$^1$H NMR(500 MHz, CD$_3$OD) δ 0.36–0.43(m, 2H), 1.14(t, J=7.6, 3H), 1.26–1.30(m, 5H), 1.49–1.60(m, 2H), 1.72–1.91(m, 4H), 2.04–2.14(m, 2H), 2.21(s, 3H), 2.38–2.63(m, 7H), 2.67–2.71(m, 1H), 2.87–2.89(m, 1H), 3.03–3.22(m, 6H), 3.50–3.57(m, 2H), 3.98(q, J=7.2, 2H), 6.96–7.00(m, 1H), 7.16–7.20(m, 2H), 7.32–7.36(m, 1H)

EXAMPLE 55

Example 55 was prepared using procedures analogous to those described in Example 1 using Aldehyde 8 and Piperidine 8.

| EXAMPLE # | HPLC Method | HPLC RT (min) | ESI-MS (M + H) |
|---|---|---|---|
| 55 | LC-2 | 1.79 | 537.4 |

$^1$H-NMR(500 MHz, CD$_3$OD) δ 0.12(m, 1H), 0.80(m, 1H), 1.12(t, J=7.5, 3H), 1.25(t, J=7.3, 3H),

-continued

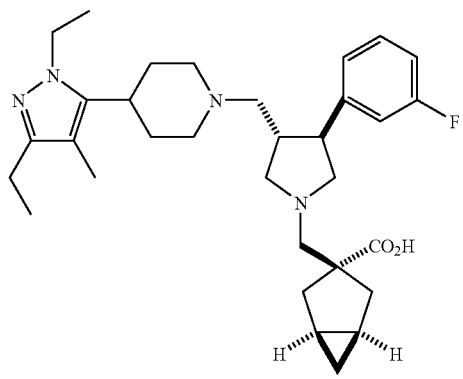

| EXAMPLE # | HPLC Method | HPLC RT (min) | ESI-MS (M + H) |
|---|---|---|---|
| | 1.42–1.63(m, 6H), 1.80(m, 1H), 1.94–2.05(m, 6H), 2.42–2.83(m, 9H), 3.00(m, 1H), 3.15–3.34(m, 5H), 3.60–3.66(m, 2H), 4.01(q, J=7.3, 2H), 6.99(m, 1H), 7.17–7.20(m, 2H), 7.35(m, 1H) | | |

EXAMPLES 56–63

Examples 56–63 were prepared using procedures analogous to those described in Examples 2 and 3 using Aldehydes 4 or 6, Pyrrolidine 2 and the appropriate piperidine.

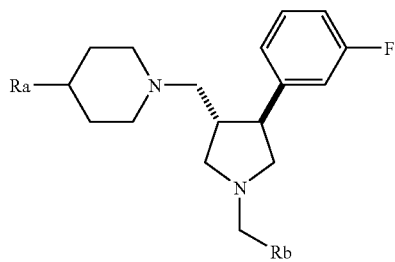

| EXAMPLE # | Ra | Rb | MS m/Z(M + 1) (HPLC A) |
|---|---|---|---|
| 56 | (pyrazolo-azepine) | cyclopentyl-CO2H | 537 (1.57 min) |
| 57 | (diethylpyrazole) | cyclohexyl-CO2H | 553 (1.73 min) |
| 58 | (1,3,5-trimethylpyrazol-4-yl) | cyclopentyl-CO2H | 497 (1.2 min) |
| 59 | (1-ethyl-5-methyl-3-methylpyrazol-4-yl) | cyclohexyl-CO2H | 525 (1.60 min) |
| 60 | (1,3,5-trimethylpyrazol-4-yl) | cyclohexyl-CO2H | 511 (1.3 min) |
| 61 | (1-ethyl-3,5-dimethylpyrazol-4-yl) | cyclopentyl-CO2H | 511 (1.49 min) |
| 62 | (1,3-diethyl-5-methylpyrazol-4-yl) | cyclopentyl-CO2H | 525 (1.5 min) |
| 63 | (1-ethyl-3-ethyl-5-methylpyrazol-4-yl) | cyclopentyl-CO2H | 525 (1.4 min) |

EXAMPLES 64–65

Examples 64–65 were prepared using procedures analogous to those described in Examples 2 and 3 using Aldehyde 6, Pyrrolidine 2 and the appropriate piperidine.

| EXAMPLE # | Ra | Rb | MS m/Z(M + 1) (HPLC A) |
|---|---|---|---|
| 64 | 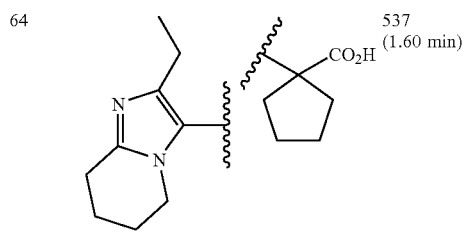 | | 537 (1.60 min) |
| 65 | 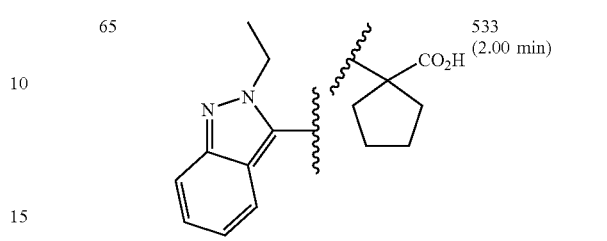 | | 533 (2.00 min) |

EXAMPLES 66–71

Examples 66–71 were prepared using procedures analogous to those described in Examples 1 and 2 using Aldehyde 4, Pyrrolidine 2 and the appropriate piperidine, which were prepared using procedures analogous to that described for Piperidine 9.

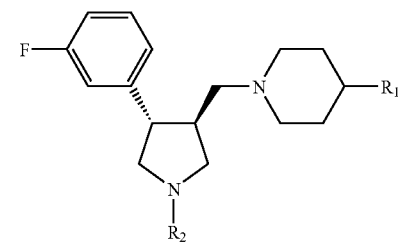

| EXAMPLE# | R$_1$ | R$_2$ | ESI-MS M/z(M + H) |
|---|---|---|---|
| 66 | 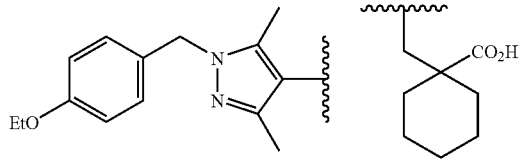 | | 631.4 |
| 67 | 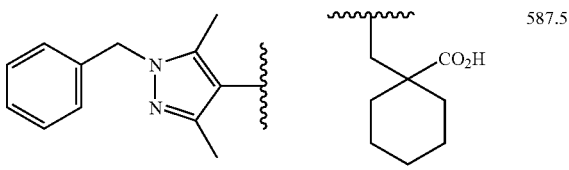 | | 587.5 |
| 68 | 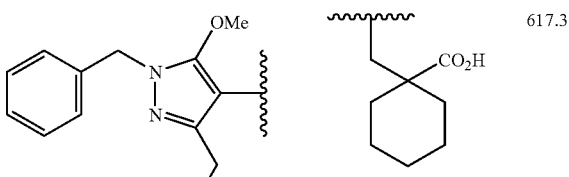 | | 617.3 |

(mixture of regioisomers)

-continued
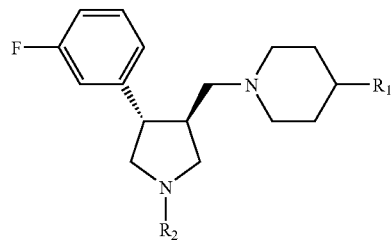
| EXAMPLE# | R₁ | R₂ | ESI-MS M/z(M + H) |
|---|---|---|---|
| 69 | 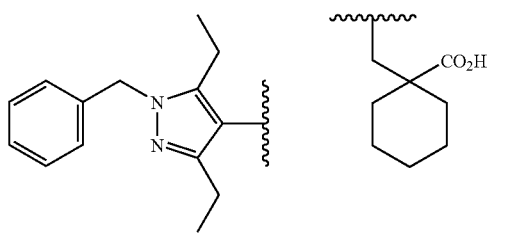 | | 615.5 |
| 70 | 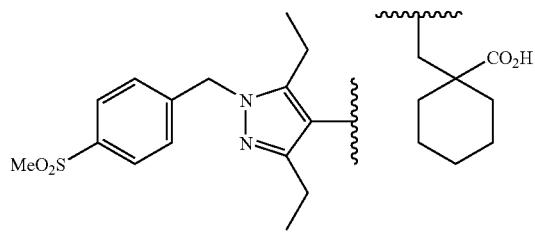 | | 693.4 |
| 71 | 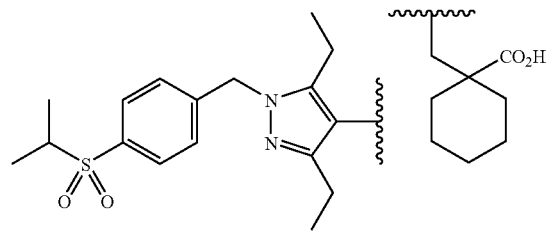 | | 721.5 |

EXAMPLE 72

1-(((3S,4S)-3-((4-(3-Methoxy-1-methyl-5-(trifluoromethyl)-(1H)-pyrazol-4-yl)piperidin-1-yl)methyl)-4-(3-fluorophenyl)pyrrolidin-1-yl)methyl)cyclohexanecarboxylic acid

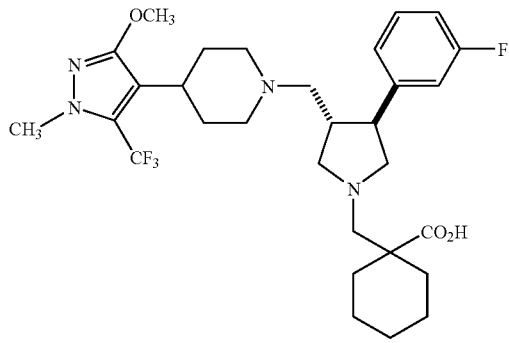

The title compound was prepared using procedures analogous to those described in Example 2 using Piperidine 35 in Step D. $^1$H NMR (500 MHz, CD$_3$OD) δ 7.37 (q, J=8, 1H), 7.22–7.12 (m, 2H), 7.00 (td, J=8, 2, 1H), 3.86 (s, 3H), 3.76 (s, 3H), 3.68–3.57 (m, 3H), 3.36–3.15 (m, 5H), 3.00 (d, J=11, 1H), 2.83 (d, J=11, 1H), 2.78–2.68 (m, 1H), 2.64–2.56 (m, 1H), 2.55 (dd, J=13, 10, 1H), 2.43 (dd, J=13, 5, 1H), 2.10–1.88 (m, 6H), 1.71–1.31 (m, 9H); ESI-MS 581.5 (M+H); HPLC A: 2.0 min.

EXAMPLE 73

1-(((3S,4S)-3-((4-(5-Methoxy-1-methyl-3-(trifluoromethyl)-(1H)-pyrazol-4-yl)piperidin-1-yl)methyl)-4-(3-fluorophenyl)pyrrolidin-1-yl)methyl)cyclohexanecarboxylic acid

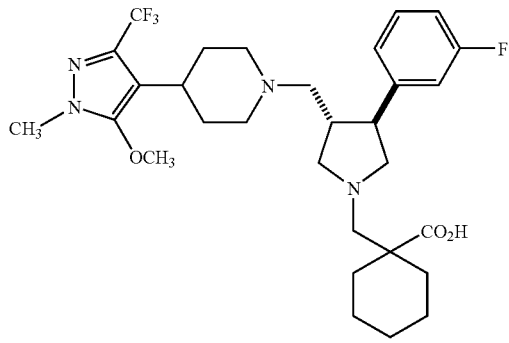

The title compound was prepared using procedures analogous to those described in Example 2 using Piperidine 36 in Step D. $^1$H NMR (500 MHz, CD$_3$OD) δ 7.37 (q, J=8, 1H), 7.22–7.12 (m, 2H), 7.01 (td, J=8, 2, 1H), 3.90 (s, 3H), 3.72 (s, 3H), 3.69–3.56 (m, 3H), 3.38–3.16 (m, 5H), 3.01 (d, J=11, 1H), 2.84 (d, J=11, 1H), 2.79–2.70 m, 1H), 2.57–2.48 (m, 2H), 2.44 (dd, J=13, 5, 1H), 2.12–1.82 (m, 5H), 1.78 (qd, J=12, 3, 1H), 1.72–1.31 (m, 9H); ESI-MS 581.5 (M+H); HPLC A: 1.9 min.

EXAMPLE 74

1-(((3S,4S)-3-(((1α,5α,6α)-6-(3,5-Diethyl-1-methyl-(1H)-pyrazol-4-yl)-3-azabicyclo[3.1.0]hexan-3-yl)methyl)-4-(3-fluorophenyl)pyrrolidin-1-yl)methyl)cyclohexanecarboxylic acid

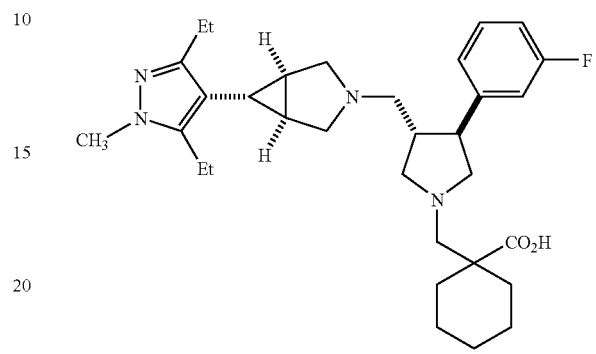

The title compound was prepared using procedures analogous to those described in Example 2 using Bicyclic Amine 1 in Step D. $^1$H NMR (500 MHz, CD$_3$OD) δ 7.34 (td, J=8, 7, 1H), 7.18–7.11 (m, 2H), 6.96 (td, J=8, 3, 1H), 3.67 (dd, J=11, 8, 1H), 3.65 (s, 3H), 3.62 (dd, J=11, 8, 1H), 3.36–3.30 (m, 1H), 3.28–3.14 (m, 5H), 2.90 (d, J=9, 1H), 2.72–2.54 (m, 3H), 2.62 (q, J=7, 2H), 2.52 (q, J=7, 2H), 2.37 (dd, J=9, 4, 1H), 2.33 (dd, J=9, 4, 1H), 2.06–1.98 (m, 2H), 1.72–1.27 (m, 11H), 1.16 (t, J=7, 3H), 1.13 (t, J=7, 3H); ESI-MS 537.5 (M+H); HPLC A: 1.7 min.

EXAMPLES 75–80

Examples 75–80 were prepared using procedures analogous to those described in Example 2 using Bicyclic Amines 2–7 in Step D.

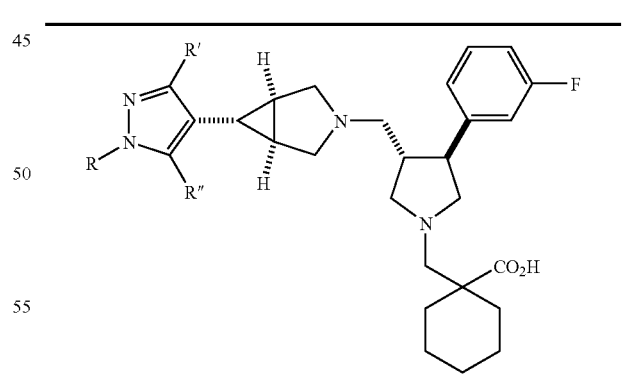

| EXAMPLE# | R | R' | R" | ESI-MS | HPLC A |
|---|---|---|---|---|---|
| 75 | Et | Et | Et | 551.6(M + H) | 1.8 min |
| 76 | i-Bu | Et | Et | 579.6(M + H) | 1.9 min |
| 77 | CH$_3$ | Et | CH$_3$ | 523.5(M + H) | 1.7 min |
| 78 | CH$_3$ | CH$_3$ | Et | 523.5(M + H) | 1.9 min |
| 79 | Et | Et | CH$_3$ | 537.6(M + H) | 1.7 min |
| 80 | Et | CH$_3$ | Et | 537.5(M + H) | 1.7 min |

EXAMPLE 81

2-{[(3R,4S)-3-[(4-(1,3-Diethyl-5-methylpyrazol-4-yl)piperidin-1-yl)ethyl)]-4-(3-fluorophenyl)pyrrolidin-1-yl]methyl}-2-methylpropionic acid Step A: 1-tert-Butoxycarbonyl-3-(R)-(tert-butyldimethylsilyloxymethyl)-4-(S)-(3-fluorophenyl)pyrrolidine A solution of 7.0 g (22.7 mmol) 3-(R)-(tert-butyldimethylsilyloxymethyl)-4-(S)-(3-fluoro)phenylpyrrolidine (Prepared as Pyrrolidine 2 above) in 75 mL of CH$_2$Cl$_2$ at 0° C. was treated with 7.5 mL (43.1 mmol) of N,N-diisopropylethylamine and 8.9 g (40.8 mmol) of di-tert-butyl dicarbonate. The resulting mixture was warmed to rt and stirred for 20 h. The reaction was partitioned between 200 mL Et$_2$O and 100 mL of H$_2$O and the layers were separated. The organic layer was dried over MgSO$_4$. The mixture was filtered and the filtrate was concentrated. Chromatography on 175 g of silica using 9:1 hexanes/diethyl ether (3 L) as the eluant to afford the title compound: $^1$H NMR (500 MHz, CDCl$_3$) δ 0.86–0.87 (6H), 1.53 (s, 9H), 2.40 (1H), 3.16–3.86 (7H), 6.91–7.32 (4H).

Step B: 1-tert-Butoxycarbonyl-3-(R)-(hydroxymethyl)-4-(S)-(3-fluorophenyl) pyrrolidine A solution of 9.3 g (22.7 mmol) 1-tert-butoxycarbonyl-3-(R)-(tert-butyldimethylsilyloxymethyl)-4-(S)-(3-fluoro)phenylpyrrolidine (from Step A) in 50 mL of THF at 0° C. was treated with 29 mL of 1.0 M tetrabutylammonium fluoride solution in THF. The resulting mixture was warmed to rt and stirred for 20 h. The reaction mixture was partitioned between 200 mL of ether and 100 mL of 50% sat'd NaHCO$_3$ and the layers were separated. The organic layer was dried over MgSO$_4$ and concentrated. Purification by Biotage Flash 75 using a 75 L cartridge and 6.0 L of 9:1 v/v heptane/ethyl acetate as the eluant afforded the title compound: $^1$H NMR (500 MHz, CDCl$_3$) δ 1.47 (9H), 2.48 (1H), 3.10–3.89 (7H), 6.92–7.33 (4H).

Step C: 1-tert-Butoxycarbonyl-3-(R)-(formyl)-4-(S)-(3-fluorophenyl)pyrrolidine

A solution of 4.3 mL (49.8 mmol) of oxalyl chloride in 90 mL of CH$_2$Cl$_2$ at −78° C. was treated with 5.4 mL (75.7 mmol) of DMSO maintaining the temperature at less than −60° C. The resulting mixture was stirred cold for 5 min. A solution of 6.4 g (21.6 mmol) of 1-tert-butoxycarbonyl-3-(R)-(hydroxymethyl)-4-(S)-(3-fluoro)phenylpyrrolidine (from Step B) in 10 mL of CH$_2$Cl$_2$ was added maintaining the temperature at less than −60° C. The resulting mixture was stirred cold for 60 min. The mixture was treated with 30 mL (173.1 mmol) of N,N-diisopropylethylamine maintaining the temperature at less than −60° C. The reaction was warmed to 0° C., stirred for 20 min and quenched with 20 mL 0.5 N KHSO$_4$. The mixture was partitioned between 250 mL of CH$_2$Cl$_2$ and 100 mL of H$_2$O and the layers were separated. The aqueous layer was extracted with 250 mL of CH$_2$Cl$_2$. The combined organic phases were dried over MgSO$_4$ and concentrated. Purification by Biotage Flash 75 using 75 L cartridge and 6.0 L of 9:1 v/v heptane/ethyl acetate as the eluant afforded the title compound: $^1$H NMR (500 MHz, CDCl$_3$) δ 1.48 (s, 9H), 2.48 (1H), 3.17–3.89 (6H), 6.96–7.35 (4H), 9.67 (s, 1H).

Step D: 1-tert-Butoxycarbonyl-3-(R)-(1-(R/S)-cyano-1-(R/S)-(4-(1,3-diethyl-5-methylpyrazol-4-yl)piperidin-1-yl)methyl)-4-(S)-(3-fluorophenyl)pyrrolidine A mixture of 880 mg (3.0 mmol) of 1-tert-butoxycarbonyl-3-(R)-(formyl)-4-(S)-(3-fluorophenyl)pyrrolidine (from Step C), 669 mg (3.0 mmol) of Piperidine 1.0, 0.60 mL (4.5 mmol) of trimethylsilylcyanide and 480 mg (4.5 mmol) of lithium perchlorate in 15 mL of THF was heated at reflux for 2.5 h. The mixture was cooled to rt and partitioned between 100 mL of ether and 50 mL of 1.0 N NaOH. The organic layer was separated, dried over MgSO4 and concentrated. Chromatography on a Biotage 40M using 4:1 v/v hexanes/EtOAc as the eluant afforded the title compound.

Step E: 1-tert-Butoxycarbonyl-3-(R)-(1-(R)-(4-(1,3-diethyl-5-methylpyrazol-4-yl)piperidin-1-yl)ethyl)-4-(S)-(3-fluorophenyl)pyrrolidine A solution of 910 mg (1.7 mmol) of 1-tert-butoxycarbonyl-3-(R)-(1-(R/S)-cyano-1-(R/S)-(4-(1,3-diethyl-5-methylpyrazol-4-yl)piperidin-1-yl)methyl)-4-(S)-(3-fluorophenyl)pyrrolidine (from Step D) at 0° C. was treated with 8.0 mL of 1.4 M methylmagnesium bromide solution in THF/toluene. The resulting mixture was warmed to rt and stirred for 20 h. The reaction was quenched with 50 mL of sat'd NH$_4$Cl/50 g ice and the quenched mixture was extracted with 2×100 mL of ether. The extracts were dried over MgSO$_4$, combined and concentrated. Chromatography on a Biotage 40 M using 2:1 v/v hexanes/EtOAc afforded the title compound contaminated with ~5% of its α-(S) diastereomer. Preparative HPLC (Chiralcel OD 2×25 cm column, 92:8 v/v hexanes/iPrOH, 9.0 mL/min, 210 nM) afforded the pure title compound (Retention time=13.8 min).

Step F: 3-(R)-(1-(R)-(4-(1,3-Diethyl-5-methylpyrazol-4-yl)piperidin-1-yl)ethyl)-4-(S)-(3-fluorophenyl)pyrrolidine The title compound was prepared from 1-tert-butoxycarbonyl-3-(R)-(1-(R)-(4-(1,3-diethyl-5-methylpyrazol-4-yl)piperidin-1-yl)ethyl)-4-(S)-(3-fluorophenyl)pyrrolidine (from Step E) using a procedure analogous to that described for Piperidine 8, Step F. $^1$H NMR (500 MHz) δ 0.94 (d, J=6.4, 3H), 1.08 (m, 1H), 1.19 (t, J=7.5, 3H), 1.35 (t, J=7.2, 3H), 1.56 (m, 1H), 1.79 (m, 1H), 1.92 (m, 1H), 2.10–2.25 (m, 5H), 2.33 (m, 1H), 2.45–2.88 (m, 8H), 3.19–3.39 (m, 3H), 4.01 (q, J=7.2, 2H), 6.83 (m, 1H), 7.04 (m, 1H), 7.10 (m, 1H), 7.22 (m, 1H).

Step G: 2-{[(3R,4S)-3-[(4-(1,3-Diethyl-5-methylpyrazol-4-yl)piperidin-1-yl)ethyl)]4-(3-fluorophenyl)pyrrolidin-1-yl]methyl}-2-methylpropionic acid, benzyl ester The title compound was prepared from 3-(R)-(1-(R)-(4-(1,3-diethyl-5-methylpyrazol-4-yl)piperidin-1-yl)ethyl)-4-(S)-(3-fluorophenyl)pyrrolidine (from Step F) and Aldehyde 2 using a procedure analogous to that described in Example 1, Step D. $^1$H NMR (500 MHz) δ 0.81 (d, J=6.4, 3H), 1.20–1.39 (m, 16H), 1.60 (m, 1H), 1.87 (m, 1H), 2.15–2.26 (m, 6H), 2.44–2.76 (m, 9H), 2.95 (m, 1H), 3.17 (m, 1H), 4.02 (q, J=7.2, 2H), 5.13 (ABq, J=12.4, 2H), 6.81 (m, 1H), 7.12–7.18 (m, 3H), 7.27–7.40 (m, 6H).

Step H: 2-{[(3R,4S)-3-[(4-(1,3-Diethyl-5-methylpyrazol-4-yl)piperidin-1-yl)ethyl)]-4-(3-fluorophenyl)pyrrolidin-1-yl]methyl}-2-methylpropionic acid The title compound was prepared from 2-{[(3R,4S)-3-[(4-(1,3-diethyl-5-methylpyrazol-4-yl)piperidin-1-yl)ethyl)]-4-(3-fluorophenyl)pyrrolidin-1-yl]methyl}-2-methylpropionic acid, benzyl ester (from Step G) using a procedure analogous that described in Example 1, Step E. $^1$H NMR (500 MHz, CD$_3$OD) δ 0.96–1.03 (m, 4H), 1.11–1.17 (m, 4H), 1.22–1.28 (m, 9H), 1.51–1.53 (m, 1H), 1.72–1.80 (m, 1H), 2.01–2.06 (m, 1H), 2.16 (s, 3H), 2.21–2.27 (m, 1H), 2.31–2.33 (m, 1H), 2.45–2.54 (m, 3H), 2.68–2.79 (m, 3H), 3.13–3.26 (m, 4H), 3.47–3.52 (m, 1H), 3.58–3.69 (m, 2H), 3.98 (q, J=7.2, 2H), 6.95–6.99 (m, 1H), 7.19–7.26 (m, 2H), 7.33–7.38 (m, 1H). ESI-MS 513.5 (M+H); HPLC LC 1:1.6 min.

EXAMPLES 82–86

The compounds in Examples 82–86 were prepared using procedures analogous to those described in Example 81 substituting the appropriate Piperidine in Step D and Aldehyde in Step G. In cases where the diastereomers obtained in Step E were not separable using flash chromatography on silica gel, they were separated by preparative HPLC (Chiralcel® OD 2×25 cm column, 90:10 v/v hexanes/iPrOH eluant).

| EXAMPLE# | Piperidine | Aldehyde | HPLC Method | HPLC RT (min) | ESI-MS (M + H) |
|---|---|---|---|---|---|
| 82 | 8 | 6 | LC-1 | 1.55 | 539.5 |

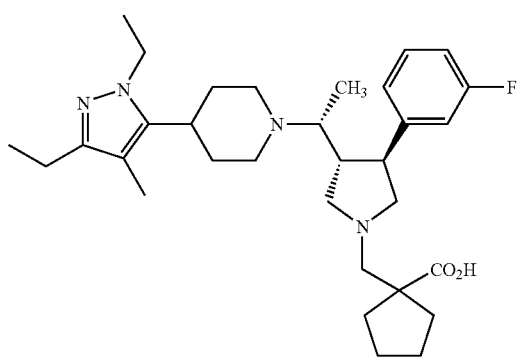

$^1$H NMR(500 MHz, CDCl$_3$): δ0.94(d, J=6.4 Hz, 3H), 0.87–3.45 (40H), 3.99(q, J=7.1 Hz, 2H), 6.86–7.28(4H)

| 83 | 8 | 4 | LC-1 | 1.63 | 553.6 |

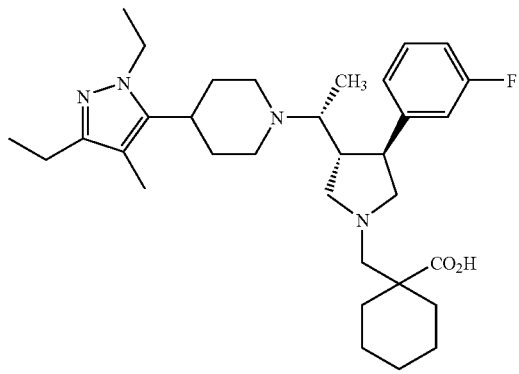

$^1$H NMR(500 MHz, CDCl$_3$): δ0.94(d, J=6.4 Hz, 3H), 0.87–3.43 (42H), 3.99(q, J=7.1 Hz, 2H), 6.85–7.28(4H)

-continued

| EXAMPLE# | Piperidine | Aldehyde | HPLC Method | HPLC RT (min) | ESI-MS (M + H) |
|---|---|---|---|---|---|
| 84 | 8 | 3 | LC-1 | 1.6 | 541.6 |

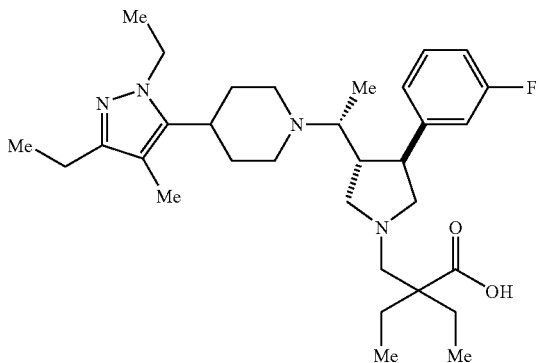

$^1$H NMR(500 MHz, CD$_3$OD)δ0.88–0.91(m, 6H), 1.01(d, 3H), 1.09–1.15(m, 4H), 1.20–1.26(m, 4H), 1.58–1.72(m, 5H), 1.89–1.95(m, 4H), 2.01–2.04(m, 1H), 2.30–2.33(m, 1H), 2.47–2.58(m, 4H), 2.67–2.81(m, 3H), 3.13–3.31(m, 4H), 3.47–3.63(m, 3H), 3.97(q, J=7.2, 2H), 6.94–6.98(m, 1H), 7.19–7.26(m, 2H), 7.33–7.37(m, 1H)

| 85 | 10 | 5 | LC-1 | 1.39 | 525.5 |

$^1$H NMR(500 MHz, CDCl$_3$): δ0.61(d, 6.1 Hz, 3H), 0.86–3.45 (38H), 4.00(q, J=7.1 Hz, 2H), 6.85–7.27(4H)

| 86 | 10 | 9 | LC-1 | 1.6 | 551.6 |

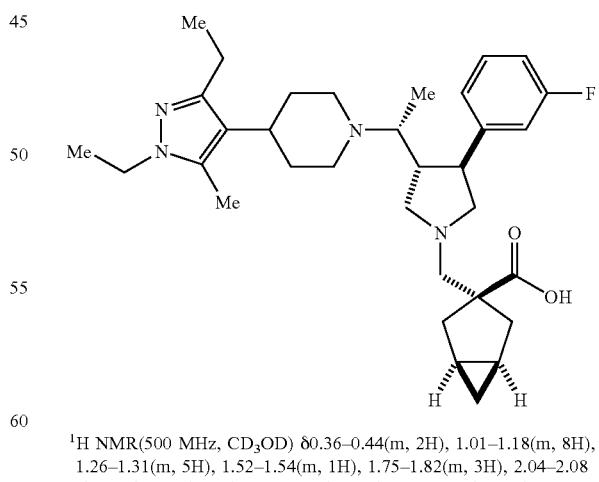

$^1$H NMR(500 MHz, CD$_3$OD) δ0.36–0.44(m, 2H), 1.01–1.18(m, 8H), 1.26–1.31(m, 5H), 1.52–1.54(m, 1H), 1.75–1.82(m, 3H), 2.04–2.08 (m, 1H), 2.17(s, 3H), 2.23–2.32(m, 2H), 2.43–2.55(m, 5H), 2.66–2.74(m, 2H, 2.79–2.82(m, 1H), 3.09–3.16(m, 4H), 3.41–3.47(m, 2H), 3.54–3.58(m, 1H), 3.98(q, J=7.2, 2H), 6.92–6.96(m, 1H), 7.19–7.25(m, 2H), 7.31–7.35(m, 1H)

EXAMPLES 87–92

Examples 87–92 were prepared using procedures analogous to those described in Examples 1 and 2 using Aldehyde 4, Pyrrolidine 2 and the appropriate piperidine, which were prepared using procedures analogous to that described for Piperidine 9.

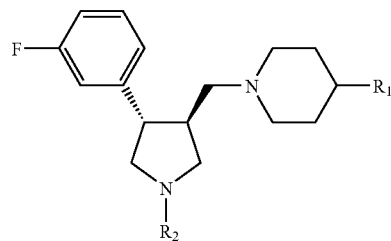

| EXAMPLE# | R₁ | R₂ | ESI-MS M/z(M + H) |
|---|---|---|---|
| 87 | cyclopropylmethyl-5-methyl-3-ethyl-pyrazol-4-yl | 1-carboxycyclohexyl-methyl | 565.4 |
| 88 | cyclopropylmethyl-5-ethyl-3-methyl-pyrazol-4-yl | 1-carboxycyclohexyl-methyl | 565.4 |
| 89 | cyclopropylmethyl-5-methyl-3-ethyl-pyrazol-4-yl | 1-carboxycyclopentyl-methyl | 551.4 |
| 90 | cyclopropylmethyl-5-ethyl-3-methyl-pyrazol-4-yl | 1-carboxycyclopentyl-methyl | 551.4 |
| 91 | cyclopropylmethyl-5-methyl-3-ethyl-pyrazol-4-yl | bicyclic-CO₂H | 563.2 |
| 92 | (4-methylsulfonylphenyl)methyl-5-methyl-3-ethyl-pyrazol-4-yl | 1-carboxycyclohexyl-methyl | 678.5 |

EXAMPLES 93–103

Examples 93–103 were prepared according to the general procedure given in Example 1 and 2, employing the appropriate aldehydes and piperidines containing substituted pyrazoles.

| EXAMPLE # | Ra | Rb | Rc | MS m/Z (M + 1) |
|---|---|---|---|---|
| 93 | 3-vinyl-1-ethyl-5-methylpyrazol-4-yl | H | 1-carboxycyclohexyl | 537 |
| 94 | 2-ethyl-pyrrolo-pyrazole | H | 1-carboxycyclohexyl | 537 |
| 95 | 2-ethyl-pyrrolo-pyrazole | H | 1-carboxycyclopentyl | 523 |
| 96 | 2-cyclopropyl-pyrrolo-pyrazole | H | 1-carboxycyclohexyl | 535 |
| 97 | 2-cyclopropyl-pyrrolo-pyrazole | H | 1-carboxycyclohexyl | 549 |
| 98 | 2-cyclopropyl-tetrahydro-pyrazolo-pyridine | H | 1-carboxycyclopentyl | 549 |
| 99 | 2-cyclopropyl-tetrahydro-pyrazolo-pyridine | H | 1-carboxycyclohexyl | 563 |
| 100 | 2-methyl-tetrahydro-pyrazolo-pyridine | H | 1-carboxycyclohexyl | 537 |
| 101 | 2-methyl-tetrahydro-pyrazolo-pyridine | H | 1-carboxycyclopentyl | 523 |
| 102 | 2-methyl-tetrahydro-pyrazolo-pyridine | H | 2-carboxyprop-2-yl | 497 |
| 103 | 2-methyl-tetrahydro-pyrazolo-pyridine | OH | 1-carboxycyclohexyl | 553 |

EXAMPLES 104–114

The compounds in 104–114 were prepared using procedures analogous to those described in Example 81 substituting the appropriate Piperidine in Step D and Aldehyde in Step G.

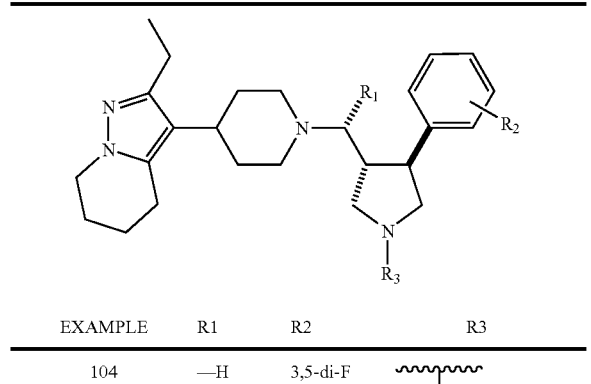

| EXAMPLE | R1 | R2 | R3 |
|---|---|---|---|
| 104 | —H | 3,5-di-F | 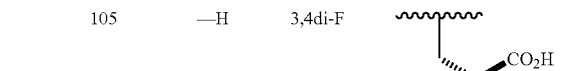 |

HPLC Method: LC-1   HPLC RT: 1.60 min   ESI-MS(M + H): 567.5

| | | | |
|---|---|---|---|
| 105 | —H | 3,4-di-F |  |

HPLC Method: LC-1   HPLC RT: 1.65 min   ESI-MS(M + H): 567.5

| | | | |
|---|---|---|---|
| 106 | —CH$_3$ | 3-F |  |

HPLC Method: LC-1   HPLC RT: 1.70 min   ESI-MS(M + H): 563.5

| | | | |
|---|---|---|---|
| 107 | —CH$_3$ | 3-F |  |

HPLC Method: LC-1   HPLC RT: 1.60 min   ESI-MS(M + H): 537.5

| | | | |
|---|---|---|---|
| 108 | —CH$_3$ | 3,5-di-F | |

HPLC Method: LC-1   HPLC RT: 1.80 min   ESI-MS(M + H): 581.4

-continued

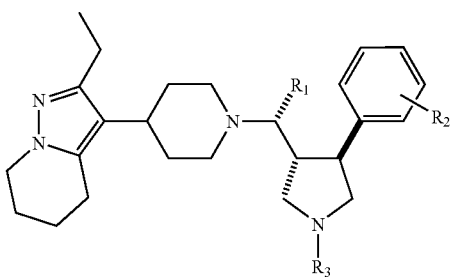

| EXAMPLE | R1 | R2 | R3 |
|---|---|---|---|
| 109 | —CH$_3$ | 3,5-di-F | 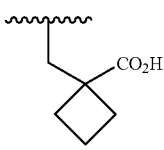 |

HPLC Method: LC-1   HPLC RT: 1.68 min   ESI-MS(M + H): 555.5

| | | | |
|---|---|---|---|
| 110 | —CH$_3$ | 3,5-di-F | 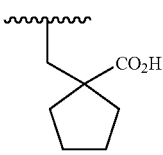 |

HPLC Method: LC-1   HPLC RT: 1.76 min   ESI-MS(M + H): 569.5

| | | | |
|---|---|---|---|
| 111 | —H | 3,5-di-F | 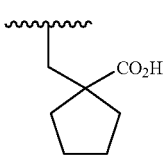 |

HPLC Method: LC-1   HPLC RT: 1.70 min   ESI-MS(M + H): 555.5

| | | | |
|---|---|---|---|
| 112 | —H | 3,4-di-F | 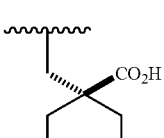 |

HPLC Method: LC-1   HPLC RT: 1.80 min   ESI-MS(M + H): 567.5

| | | | |
|---|---|---|---|
| 113 | —CH$_3$ | 3,4-di-F | 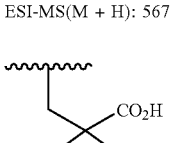 |

HPLC Method: LC-1   HPLC RT: 1.70 min   ESI-MS(M + H): 569.5

-continued

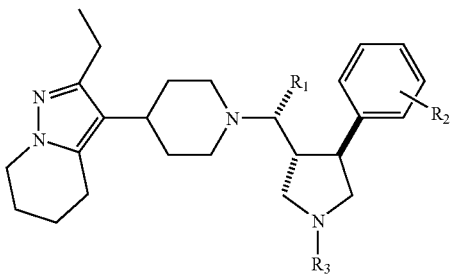

| EXAMPLE | R1 | R2 | R3 |
|---|---|---|---|
| 114 | —CH₃ | 3,4-di-F | ![cyclobutyl-CH2-CO2H] |

HPLC Method: LC-1   HPLC RT: 1.70 min   ESI-MS(M + H): 555.5

EXAMPLES 115–118

The compounds in Examples 115–118 were prepared using procedures analogous to those described in Example 81 substituting the appropriate Piperidine in Step D and Aldehyde in Step G.

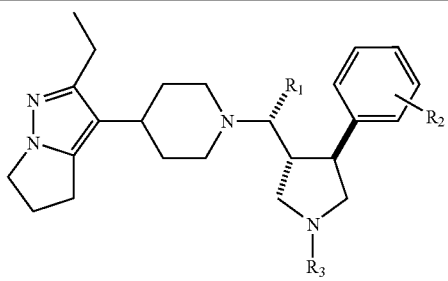

| EXAMPLE | R1 | R2 | R3 |
|---|---|---|---|
| 115 | —H | 3,5-di-F | ![bicyclic-CO2H] |

HPLC Method: LC-1   HPLC RT: 1.90 min   ESI-MS(M + H): 553.5

| 116 | —CH | 3-F | ![gem-dimethyl-CO2H] |

HPLC Method: LC-1   HPLC RT: 1.50 min   ESI-MS(M + H): 511

| 117 | —CH₃ | 3-F | ![cyclobutyl-CO2H] |

HPLC Method: LC-1   HPLC RT: 1.50 min   ESI-MS(M + H): 523

-continued

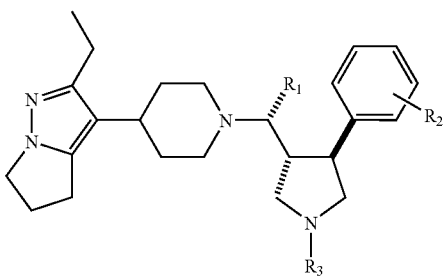

| EXAMPLE | R1 | R2 | R3 |
|---|---|---|---|
| 118 | —CH₃ | 3-F | ![cyclopentyl-CO2H] |

HPLC Method: LC-1   HPLC RT: 1.60 min   ESI-MS(M + H): 537

EXAMPLE 119

Example 119 was prepared using procedures analogous to those described in Example 81 substituting the appropriate Piperidine in Step D and Aldehyde in Step G.

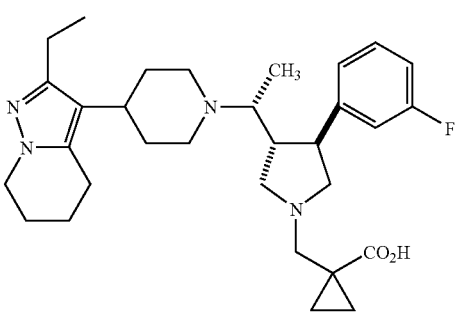

| Example # | ESI | HPLC RT(LC1) |
|---|---|---|
| 119 | 523.4 | 1.5 min |

¹H NMR(500 MHz, CD₃OD): δ0.71–0.89(m, 3H), 1.00(d, J=6.5, 3H), 1.11(t, J=7.5, 3H), 1.20–1.23(m, 2H), 1.51(m, 1H), 1.65–1.98(m, 6H), 2.16–2.27(m, 2H), 2.43–2.84(m, 9H), 3.25–3.34(m, 4H), 3.53–3.76(m, 3H), 3.95(t, J=6.1, 2H), 6.98(m, 1H), 7.19–7.25(m, 2H), 7.36(m, 1H)

EXAMPLES 120–123

Examples 120–123 were prepared using procedures analogous to those described in Example 2 using the appropriate piperidines, pyrrolidines and aldehydes.

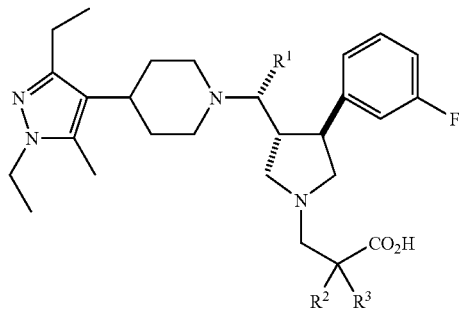

| Example # | R¹ | R² | R³ | ESI | HPLC RT (LC1) |
|---|---|---|---|---|---|
| 120 (Diastereomer 1) | H | CH₃ | CH₂CH₃ | 513.5 | 1.60 min |

$^1$H NMR(500 MHz, CD$_3$OD): δ 0.91(t, J=7.4 , 3H), 1.14(t, J=7.5, 3H), 1.20(s, 3H), 1.28(t, J=7.2, 3H), 1.48–1.59(m, 3H), 1.67–1.75(m, 2H), 1.84(dq, J=3.6, 9.2, 1H), 1.99(dt, J=2.2, 11.7, 1H), 2.06(dt, J=2.3, 11.7, 1H), 2.21.(s, 3H), 2.39 itt, J= 3.7, 12.6, 1H), 2.44–2.59(m, 4H), 2.75–2.80(m, 1H), 2.84(d, J=11.5, IH), 3.01(d, J= 11.0, 1H), 3.08(m, 1H), 3.24–3.37(m, 4H), 3.65–3.69(m, 2H), 4.00(q, J=7.3, 2H), 7.01(dt, J=2.3, 8.4, 1H), 7.17–7.21(m, 2H), 7.37(m, 1H)

| 121 (Diastereomer 2) | H | CH₂CH₃ | CH₃ | — | — |

$^1$H NMR(500 MHz, CD$_3$OD): δ 0.92(t, J=7.5, 3H), 1.14(t, J=7.6, 3H), 1.24(s, 3H), 1.28(t, J=7.3, 3H), 1.48–1.58(m, 2H), 1.62(q, J=7.4, 2H), 1.72(dq, J=3.8, 12.7, 1H), 1.84(dq, J=3.8, 12.7, 1H), 1.97(dt, J=2.2, 11.7, 1H), 2.04(dt, J=3.1, 11.7, 1H), 2.21.(s, 3H), 2.35–2.46(m, 2H), 2.51–2.57(m, 3H), 2.78(m, 1H), 2.83(d, J= 11.2, 1H), 3.00(d, J=11.4, 1H), 3.05(m, 1H), 3.21–3.38(m, 4H), 3.67–3.70(m, 2H), 4.00(g, J=7.2, 2H), 7.01(dt, J=2.7, 8.6, 1H), 7.17–7.21(m, 2H), 7.37(m, 1H)

| 122 | H | CH₃ | CH₂CF₃ | 567.5 | 1.73 min |

$^1$H NMR(500 MHz, CD$_3$OD): δ 1.15(dt, J=1.2, 7.6, 3H), 1.28(t, J=7.2, 3H), 1.33 (d, J=4.8, 3H), 1.62–1.70(m, 2H), 1.91–2.01(m, 2H), 2.23(d, J=2.1, 3H), 2.33–2.83 (m, 9H), 2.83–3.01(m, 4H), 3.01–3.21(m, 3H), 3.21–3.45(m, 3H), 4.00(q, J=7.2, 2H), 6.96(m, 1H), 7.14–7.19(m, 2H), 7.33(m, 1H)

| 123 | CH₃ | CH₃ | CH₂CF₃ | 581.5 | 1.76 min |

$^1$H NMR(500 MHz, CD$_3$OD): δ 1.14(dt, J=2.1, 7.5 Hz, 3H), 1.18(t, J=6.1,3H), 1.27(t, J=7.2, 3H), 1.33(d, J=8.2, 3H), 1.35–1.58(m, 2H), 1.64(m, 1H), 2.20(d, J= 3.5, 3H), 2.38–2.81(m, 10H), 2.85–3.11(m, 5H), 3.17–3.35(m, 3H), 3.99(q, J= 7.1, 2H), 6.93(m, 1H), 7.18–7.24(m, 2H), 7.30(m, 1H)

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I:

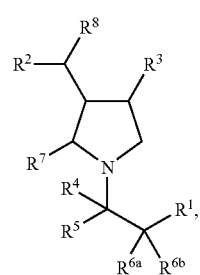

(I)

wherein:

R$^1$ is:
(1) —CO$_2$H,
(2) —NO$_2$, (3) -tetrazolyl,
(4) -hydroxyisoxazole,
(5) —SO$_2$NHCO—(C$_{0-3}$ alkyl)—R$^a$, or
(6) —P(O)(OH)(OR$^a$);
   wherein R$^a$ is independently selected from hydrogen, C$_{1-6}$ alkyl, C$_{5-6}$ cycloalkyl, benzyl and phenyl, where any one of which except hydrogen is optionally substituted with 1–3 substituents where the substituents are independently selected from halo, C$_{1-3}$ alkyl, —O—C$_{1-3}$ alkyl, and —CF$_3$, R$^2$ is:

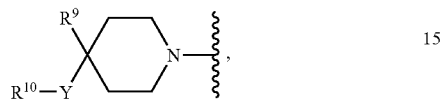

wherein "⁓" denotes the point of attachment;
R$^9$ is selected from:
(1) hydrogen,
(2) C$_{1-6}$ alkyl, which is unsubstituted or substituted with 1–4 substituents where the substituents are independently selected from hydroxy, cyano, and halo,
(3) cyano,
(4) hydroxy, and
(5) halo; and Y is:
(1) a direct single bond;
(2) —C$_{1-10}$ alkyl- or —(C$_{0-6}$ alkyl)C$_{3-6}$cycloalkyl(C$_{0-6}$ alkyl)-, either of which is optionally substituted with 1–7 substituents independently selected from:
   (a) halo,
   (b) hydroxy,
   (c) —O—C$_{1-3}$ alkyl,
   (d) —CF$_3$,
   (e) —(C$_{1-3}$ alkyl)hydroxy, and
   (f) ethylenedioxy;
(3) —(C$_{0-6}$ alkyl)-Z$^1$-(C$_{0-6}$ alkyl)-, wherein each alkyl is optionally substituted with 1–7 substituents independently selected from:
   (a) halo,
   (b) hydroxy,
   (c) —O—C$_{1-3}$ alkyl, and
   (d) —CF$_3$;
   and where Z$^1$ is selected from —SO$_2$—, —N(R$^u$)—, —N(R$^u$)C(=CHR$^s$)N(R$^u$)—, —N(R$^u$)C(=NR$^s$)N(R$^u$)—, —S—, —O—, —SO—, —SO$_2$N(R$^u$)—, —N(R$^u$)SO$_2$—, and —PO$_2$—;
   R$_u$ is hydrogen, C$_{1-6}$ alkyl, C$_{2-6}$ alkenyl, benzyl, phenyl, (CO)C$_{1-6}$ alkyl, —SO$_2$—C$_{1-6}$ alkyl, —SO$_2$-phenyl, —SO$_2$-heterocycle, or C$_{1-6}$ alkyl-C$_{3-6}$ cycloalkyl; wherein any of which except hydrogen is optionally substituted with 1–3 substituents independently selected from halo, C$_{1-3}$ alkyl, —O—C$_{1-3}$ alkyl, and —CF$_3$;
   R$^s$ is hydrogen, C$_{1-4}$ alkyl, —NO$_2$ or —CN;
(4) —(C$_{0-6}$ alkyl)-Z$^2$-(C$_{0-6}$ alkyl)-, wherein each alkyl is optionally substituted with 1–7 substituents independently selected from:
   (a) halo,
   (b) hydroxy,
   (c) —O—C$_{1-3}$ alkyl, and
   (d) —CF$_3$;

and where:
Z$^2$ is selected from —C(=O)—, —C(=O)O—, —OC(=O)—, —C(=O)NR$^v$—, —NR$^v$C(=O)—, —OC(=O)NR$^v$—, —NR$^v$C(=O)O—, and —NR$^w$C(=O)NR$^v$—;
R$^v$ is hydrogen, C$_{1-6}$ alkyl, C$_{2-6}$ alkenyl, C$_{2-6}$ alkynyl, benzyl, phenyl, or C$_{1-6}$ alkyl-C$_{3-6}$ cycloalkyl; wherein any of which except hydrogen is optionally substituted with 1–3 substituents independently selected from halo, C$_{1-3}$ alkyl, —O—C$_{1-3}$ alkyl, and —CF$_3$; and
R$^w$ is hydrogen or C$_{1-6}$ alkyl;

R$^{10}$ is:
(1) a heterocycle selected from pyrazolyl and imidazolyl, wherein the pyrazolyl or imidazolyl is substituted with three of R$^d$, wherein each R$^d$ is independently selected from the group consisting of:
   (a) halo,
   (b) cyano,
   (c) hydroxy,
   (d) C$_{1-6}$ alkyl, which is unsubstituted or substituted with 1–5 of R$^e$ where R$^e$ is independently selected from halo, cyano, hydroxy, —O—C$_{1-16}$ alkyl, —C$_{3-6}$ cycloalkyl, —CO$_2$H, —CO$_2$—(C$_{1-6}$ alkyl), —CF$_3$, —SO$_2$R$^a$, —NR$^a$R$^b$ (where R$^a$ is independently as defined above and R$^b$ is independently selected from the definitions of R$^a$), phenyl, naphthyl, biphenyl, and heterocycle;
   wherein phenyl, naphthyl, biphenyl, or heterocycle is unsubstituted or substituted with 1–7 of R$^f$ where R$^f$ is independently selected from halo, cyano, hydroxy, C$_{1-6}$ alkyl, C$_{1-6}$ haloalkyl, —O—C$_{1-6}$ alkyl, —O—C$_{1-6}$ haloalkyl, —CO$_2$H, —CO$_2$(C$_{1-6}$ alkyl), —NR$^a$R$^b$, —(C$_{1-6}$ alkyl)-NR$^a$R$^b$, —SO$_2$R$^a$, —N(R$^a$)SO$_2$R$^{b6}$, —N(R$^a$)COR$^b$, —(C$_{1-6}$ alkyl)hydroxy, —O—C$_{3-6}$ cycloalkyl, benzyloxy, phenoxy, and —NO$_2$,
   (e) —O—C$_{1-6}$ alkyl, which is unsubstituted or substituted with 1–5 of R$^e$,
   (f) —O-phenyl, which is unsubstituted or substituted with 1–5 of R$^f$,
   (g) —O-heterocycle, which is unsubstituted or substituted with 1–5 of R$^f$,
   (h) —NO$_2$,
   (i) phenyl,
   (j) —CO$_2$R$^a$,
   (k) tetrazolyl,
   (l) —NR$^a$R$^b$,
   (m) —NR$^a$—COR$^b$,
   (n) —NR$^a$—CO$_2$R$^b$,
   (o) —CO—NR$^a$R$^b$,
   (p) —OCO—NR$^a$R$^b$,
   (q) —NR$^a$CO—NR$^a$R$^b$,
   (r) —S(O)$_m$—R$^a$, wherein m is an integer selected from 0, 1, and 2,
   (s) —S(O)$_2$—NR$^a$R$^b$,
   (t) —NR$^a$S(O)$_2$—R$^b$,
   (u) —NR$^a$S(O)$_2$—NR$^a$R$^b$,
   (v) C$_{2-6}$ alkenyl,
   (w) furanyl, which is unsubstituted or substituted with benzyl which is unsubstituted or substituted with 1–7 of R$^f$ wherein R$^f$ is independently as defined above,
   (x) —C$_{3-6}$ cycloalkyl, and
   (y) —O—C$_{3-6}$ cycloalkyl; or (2) a heterocycle selected from:

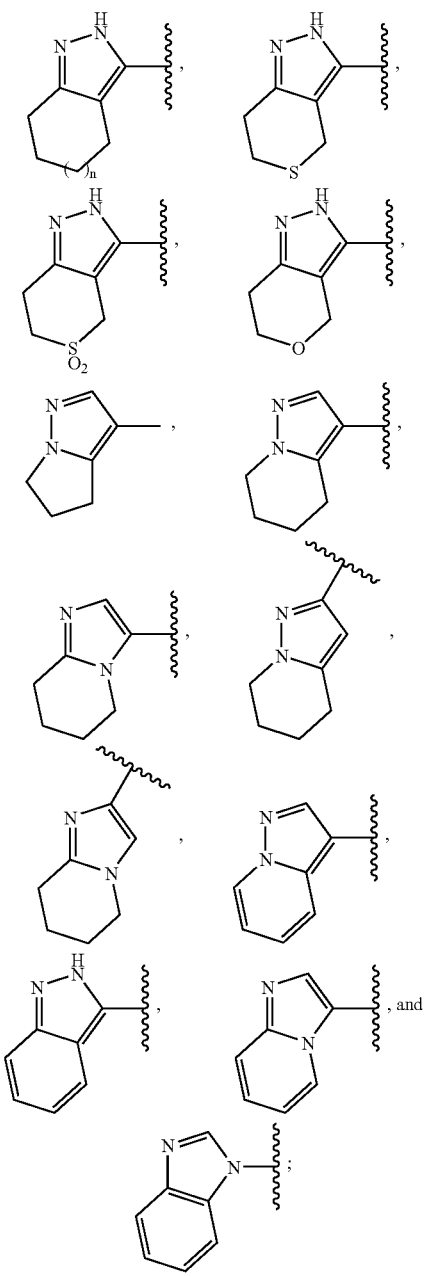

wherein n is an integer equal to zero or 1, and
the heterocycle is mono-substituted in the pyrazolyl or imidazolyl ring with any one of $R^d$ as defined above, and is either unsubstituted in the other ring or is substituted with 1 or more substituents where each substituent is independently selected from (a) to (y) of $R^d$ as defined above;

$R^3$ is phenyl, naphthyl, or heterocycle, any one of which is unsubstituted or substituted with 1–7 substituents where the substituents are independently selected from:
(a) halo,
(b) $C_{1-4}$ alkyl,
(c) $C_{1-4}$ haloalkyl,
(d) hydroxy,
(e) —O—$C_{1-4}$ alkyl,
(f) —O—$C_{1-4}$ haloalkyl,
(g) —$CO_2R^a$,
(h) —$NR^aR^b$, and
(i) —$CONR^aR^b$;

$R^4$ is hydrogen, $C_{1-10}$ alkyl, $C_{3-8}$ cycloalkyl, —($C_{1-3}$ alkyl)-$C_{3-8}$ cycloalkyl, —($C_{0-2}$ alkyl)-($C_{3-8}$ cycloalkylidenyl)-($C_{1-2}$ alkyl), $C_{2-10}$ alkenyl, $C_{2-10}$ alkynyl, cyclohexenyl, phenyl, —($C_{1-6}$ alkyl)-phenyl, naphthyl, dihydronaphthyl, tetrahydronaphthyl, octahydronaphthyl, biphenyl, or heterocycle; wherein any one of which except for hydrogen is unsubstituted or substituted with 1–7 of $R^d$ where $R^d$ is independently as defined above;

$R^5$ is hydrogen or $C_{1-6}$ alkyl, wherein the alkyl is unsubstituted or substituted with 1–7 substituents where the substituents are independently selected from:
(a) halo,
(b) —$CF_3$,
(c) hydroxy,
(d) $C_{1-3}$ alkyl,
(e) —O—$C_{1-3}$ alkyl,
(f) —$CO_2R^a$,
(g) —$NR^aR^b$, and
(h) —$CONR^aR^b$;

or alternatively $R^4$ and $R^5$ together with the carbon atom to which they are attached form a $C_{3-8}$ cycloalkyl ring which may be unsubstituted or substituted with 1–7 of $R^d$;

$R^{6a}$ and $R^{6b}$ are each independently $C_{1-6}$ alkyl, $C_{2-6}$ alkenyl, $C_{2-6}$ alkynyl, $C_{3-8}$ cycloalkyl, phenyl, naphthyl, or heterocycle; wherein any one of which is unsubstituted or substituted with 1–7 substituents where the substituents are independently selected from:
(a) halo,
(b) $C_{1-4}$ haloalkyl,
(c) hydroxy,
(d) $C_{1-4}$ alkyl,
(e) —O—$C_{1-4}$alkyl,
(f) —O—$C_{1-4}$ haloalkyl,
(g) $C_{3-8}$ cycloalkyl,
(h) —$CO_2R^a$,
(i) —$NR^aR^b$, and
(j) —$CONR^aR^b$;

or alternatively $R^{6a}$ and $R^{6b}$ together with the carbon atom to which they are attached form:
(a) a 3- to 8-membered saturated carbocyclic ring, in which one of the ring carbons is optionally a member of a 3- to 8-membered spiro ring containing carbon atoms and optionally 1 or 2 heteroatoms independently selected from nitrogen, oxygen and sulfur;
(b) a 4- to 8-membered monocyclic heterocycle containing from 1 to 3 heteroatoms independently selected from nitrogen, oxygen and sulfur, in which one of the ring carbons is optionally a member of a 3- to 8-membered spiro ring containing carbon atoms and optionally 1 or 2 heteroatoms independently selected from nitrogen, oxygen and sulfur;
(c) a 5- to 8-membered saturated carbocyclic ring to which is fused a $C_{3-8}$ cycloalkyl, or
(d) a 5- to 8-membered heterocyclic ring containing from 1 to 3 heteroatoms selected from nitrogen, oxygen and sulfur, to which is fused a $C_{3-8}$ cycloalkyl,
wherein the ring system of (a), (b), (c) or (d) is optionally substituted with from 1 to 3 substituents selected from halo, $C_{1-4}$ alkyl, $C_{1-4}$ haloalkyl, —O—$C_{1-4}$ alkyl, —O—$C_{1-4}$ haloalkyl, and hydroxy;

$R^7$ is hydrogen or $C_{1-6}$ alkyl; and
$R^8$ is hydrogen or $C_{1-6}$ alkyl;
or a pharmaceutically acceptable salt thereof.

2. The compound according to claim 1 wherein $R^1$ is:
   (1) —$CO_2H$,
   (2) —$P(O)(OH)_2$, or
   (3) -tetrazolyl;
or a pharmaceutically acceptable salt thereof.

3. The compound according to claim 1 wherein $R^1$ is:
   (1) —$CO_2H$, or
   (2) -tetrazolyl;
or a pharmaceutically acceptable salt thereof.

4. The compound according to claim 1 wherein $R^1$ is —$CO_2H$;
or a pharmaceutically acceptable salt thereof.

5. The compound according to claim 1, wherein $R^2$ is:

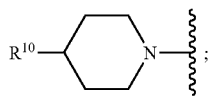

or a pharmaceutically acceptable salt thereof.

6. The compound according to claim 1 wherein $R^3$ is phenyl, thienyl, pyrazolyl, thiazolyl, thiadiazolyl, furanyl, oxadiazolyl, pyrazinyl, pyrimidinyl, or pyridyl, any one of which is unsubstituted or substituted with 1–5 substituents where the substituents are independently selected from:
   (a) halo,
   (b) —$CF_3$,
   (c) hydroxy,
   (d) $C_{1-3}$ alkyl, and
   (e) —O—$C_{1-3}$ alkyl;
or a pharmaceutically acceptable salt thereof.

7. The compound according to claim 1 wherein $R^3$ is phenyl or thienyl, either of which is unsubstituted or substituted with 1–5 substituents where the substituents are independently selected from:
   (a) halo,
   (b) —$CF_3$,
   (c) hydroxy, and
   (d) $C_{1-3}$ alkyl;
or a pharmaceutically acceptable salt thereof.

8. The compound according to claim 1 wherein $R^3$ is phenyl or thienyl, wherein the phenyl is optionally substituted with 1–5 substituents independently selected from fluoro and chloro;
or a pharmaceutically acceptable salt thereof.

9. The compound according to claim 1 wherein $R^4$ and $R^5$ are both hydrogen;
or a pharmaceutically acceptable salt thereof.

10. The compound according to claim 1, wherein $R^{6a}$ and $R^{6b}$ are each independently $C_{1-6}$ alkyl or $C_{3-6}$ cycloalkyl, either of which is unsubstituted or substituted with 1–7 substituents independently selected from:
    (a) halo,
    (b) —$CF_3$,
    (c) hydroxy, and
    (d) —O—$C_{1-13}$ alkyl;
or $R^{6a}$ and $R^{6b}$ together with the carbon atom to which they are attached form:
    (a) a 3- to 6-membered saturated carbocyclic ring,
    (b) a 4- to 6-membered saturated heterocyclic ring containing one oxygen atom, or
    (c) a 5- or 6-membered saturated carbocyclic ring to which is fused a $C_{3-6}$ cycloalkyl;

wherein the ring system of (a), (b), or (c) is optionally substituted with from 1 to 3 substituents selected from halo, $C_{1-4}$ alkyl, $C_{1-4}$ haloalkyl, —O—$C_{1-4}$ alkyl, —O—$C_{1-4}$ haloalkyl, or hydroxy;
or a pharmaceutically acceptable salt thereof.

11. The compound according to claim 1, wherein $R^{6a}$ and $R^{6b}$ are each $C_{1-3}$ alkyl;
or one of $R^{6a}$ and $R^{6b}$ is $C_{1-3}$ alkyl, and the other of $R^{6a}$ and $R^{6b}$ is $C_{3-6}$ cycloalkyl;
or $R^{6a}$ and $R^{6b}$ together with the carbon atom to which they are attached form cyclopropylidenyl, cyclobutylidenyl, cyclopentylidenyl, cyclohexylidenyl, bicyclo[3.1.0]cyclohexylidenyl, tetrahydropyranylidenyl, or tetrahydrofuranylidenyl;
or a pharmaceutically acceptable salt thereof.

12. The compound according to claim 1, wherein $R^7$ is hydrogen;
or a pharmaceutically acceptable salt thereof.

13. The compound according to claim 1, wherein $R^8$ is hydrogen or methyl;
or a pharmaceutically acceptable salt thereof.

14. The compound according to claim 1 wherein $R^9$ is hydrogen, fluoro, hydroxy or $C_{1-6}$ alkyl;
or a pharmaceutically acceptable salt thereof.

15. The compound according to claim 1 wherein $R^9$ is hydrogen;
or a pharmaceutically acceptable salt thereof.

16. The compound according to claim 1, wherein Y is a direct single bond;
or a pharmaceutically acceptable salt thereof.

17. The compound according to claim 1, wherein $R^{10}$ is:
    (1) a heterocycle selected from pyrazolyl and imidazolyl, wherein the pyrazolyl or imidazolyl is substituted with three substituents independently selected from the group consisting of:
        (a) halo,
        (b) cyano,
        (c) hydroxy,
        (d) $C_{1-6}$ alkyl, which is unsubstituted or substituted with 1–5 of $R^e$ where $R^e$ is independently selected from halo, cyano, hydroxy, —O—$C_{1-6}$ alkyl, —$C_{3-5}$ cycloalkyl, —$CO_2H$, —$CO_2(C_{1-6}$ alkyl), —$CF_3$, —$SO_2R^a$, —$NR^aR^b$,
            where $R^a$ and $R^b$ are independently selected from hydrogen, $C_{1-6}$ alkyl, $C_{5-6}$ cycloalkyl, benzyl or phenyl, which is unsubstituted or substituted with 1–3 substituents where the substituents are independently selected from halo, $C_{1-3}$ alkyl, —O—$C_{1-3}$ alkyl, $C_{1-3}$ fluoroalkyl, and —O—$C_{1-3}$ fluoroalkyl,
            phenyl, naphthyl, biphenyl, and heterocycle,
            wherein the phenyl, naphthyl, biphenyl or heterocycle is unsubstituted or substituted with 1–7 of $R^f$ where $R^f$ is independently selected from halo, cyano, hydroxy, $C_{1-4}$ alkyl, —O—$C_{1-4}$ alkyl, —O—$C_{3-5}$ cycloalkyl, —$CO_2H$, —$CO_2(C_{1-6}$ alkyl), —$CF_3$, —$OCF_3$, —$SO_2R^a$, —$N(R^a)SO_2R^b$ and —$NR^aR^b$,
        (e) —O—$C_{1-6}$ alkyl, which is unsubstituted or substituted with 1–5 of $R^e$,
        (f) —$NO_2$,
        (g) phenyl,
        (h) —$CO_2R^a$,
        (i) tetrazolyl,
        (j) —$NR^aR^b$,
        (k) —$NR^a$—$COR^b$,
        (l) —$NR^a$—$CO_2R^b$, (m) —CO—NR$^a$R$^b$,
(n) —OCO—NR$^a$R$^b$,
(o) —NR$^a$CO—NR$^a$R$^b$,
(p) —S(O)$_m$—R$^a$, wherein m is an integer selected from 0, 1, and 2,
(q) —S(O)$_2$—NR$^a$R$^b$,
(r) —NR$^a$S(O)$_2$—R$^b$,
(s) —NR$^a$S(O)$_2$—NR$^a$R$^b$,
(t) —C$_{2-3}$ alkenyl,
(u) —C$_{3-6}$ cycloalkyl, and
(v) —O—C$_{3-6}$ cycloalkyl; or
(2) a heterocycle selected from:

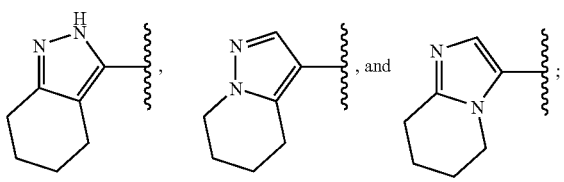

wherein the heterocycle is mono-substituted in the pyrazolyl or imidazolyl ring with any one of R$^d$ as defined above, and is either unsubstituted in the other ring or substituted with 1 to 3 substituents independently selected from:
(a) halo,
(b) C$_{1-4}$ alkyl,
(c) C$_{1-4}$ haloalkyl,
(d) —OH,
(e) —O—C$_{1-4}$ alkyl,
(f) —O—C$_{1-4}$ haloalkyl, and
(g) —CN;
or a pharmaceutically acceptable salt thereof.

18. The compound according to claim 1, wherein R$^{10}$ is:
(1) pyrazolyl substituted with three substituents independently selected from the group consisting of:
(a) fluoro,
(b) chloro,
(c) C$_{1-6}$ alkyl,
(d) —CH$_2$-phenyl, wherein the phenyl is unsubstituted or substituted with 1 or 2 substituents independently selected from chloro, fluoro, —CN, —C$_{1-3}$ alkyl, —O—C$_{1-3}$ alkyl, —O-cyclopropyl, —O-cyclobutyl, —CF$_3$, —OCF$_3$, —SO$_2$—(C$_{1-3}$ alkyl), and —N(H)SO$_2$—(C$_{1-3}$ alkyl),
(e) —CH$_2$CH$_2$-phenyl, and
(f) phenyl; or
(2) a heterocycle selected from:

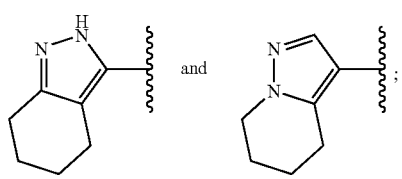

wherein the heterocycle is mono-substituted in the pyrazolyl ring with any one of R$^d$ as defined above, and is either unsubstituted in the other ring or substituted with 1 to 3 substituents independently selected from:
(a) fluoro,
(b) chloro,
(b) C$_{1-4}$ alkyl,
(c) —CF$_3$,
(d) —OH,
(e) —O—C$_{1-4}$ alkyl,
(f) —OCF$_3$, and
(g) —CN;
or a pharmaceutically acceptable salt thereof.

19. The compound according to claim 1 which is of the stereochemical configuration:

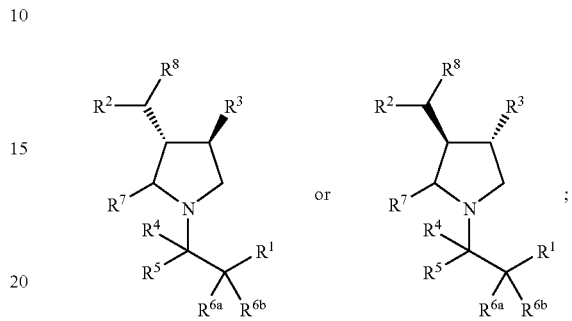

or a pharmaceutically acceptable salt thereof.

20. The compound of claim 1, which is a compound of formula (II):

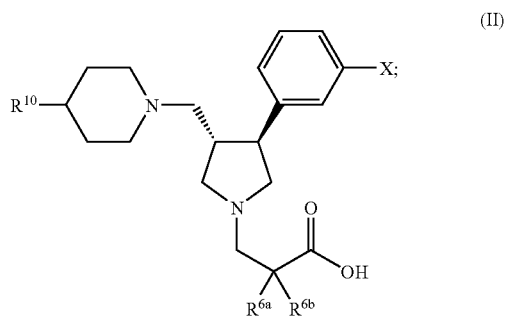

(II)

wherein
R$^{6a}$ and R$^{6b}$ are each C$_{1-3}$ alkyl;
or one of R$^{6a}$ and R$^{6b}$ is C$_{1-3}$ alkyl, and the other of R$^{6a}$ and R$^{6b}$ is C$_{3-6}$ cycloalkyl;
or R$^{6a}$ and R$^{6b}$ together with the carbon atom to which they are attached form:

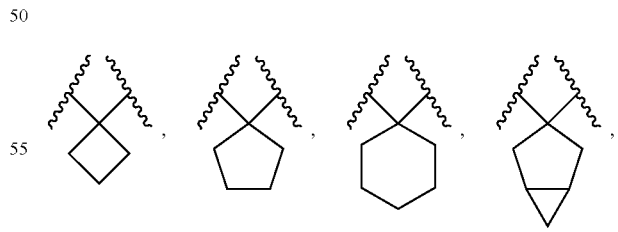

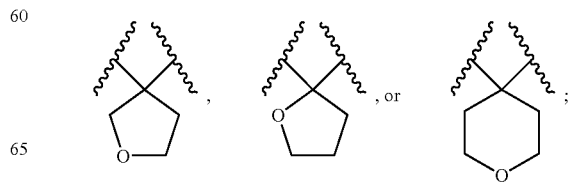

$R^{10}$ is:

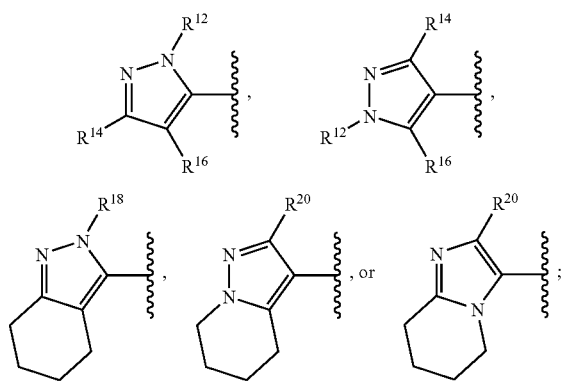

$R^{12}$ is $C_{1-3}$ alkyl, $C_{1-3}$ fluoroalkyl, or —$CH_2$-phenyl wherein the phenyl is optionally substituted with 1 or 2 substituents independently selected from chloro, fluoro, —CN, —$C_{1-3}$ alkyl, —O—$C_{1-3}$ alkyl, —O-cyclopropyl, —O-cyclobutyl, —$CF_3$, —$OCF_3$, —$SO_2$—($C_{1-3}$ alkyl), and —$NHSO_2$—($C_{1-3}$ alkyl);

each of $R^{14}$ and $R^{16}$ is independently —$C_{1-3}$ alkyl, $C_{1-3}$ fluoroalkyl, —O—$C_{1-3}$ alkyl, —O—$C_{1-3}$ fluoroalkyl, cyclopropyl, cyclobutyl, or —$CH_2$-phenyl wherein the phenyl is optionally substituted with 1 or 2 substituents independently selected from chloro, fluoro, —CN, —$C_{1-3}$ alkyl, —O—$C_{1-3}$ alkyl, —O-cyclopropyl, —O-cyclobutyl, —$CF_3$, —$OCF_3$, and —$SO_2$—($C_{1-3}$ alkyl);

$R^{18}$ is $C_{1-3}$ alkyl;

$R^{20}$ is —$C_{1-3}$ alkyl; and

X is hydrogen or fluoro;

or a pharmaceutically acceptable salt thereof.

21. The compound according to claim 20, wherein $R^{10}$ is:

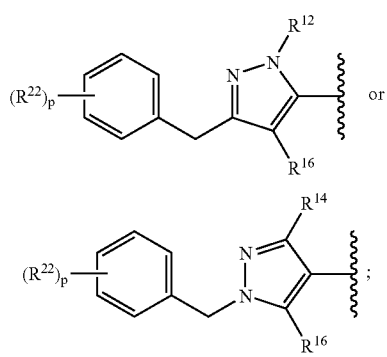

$R^{12}$ is methyl or ethyl;

$R^{14}$ is methyl or ethyl;

$R^{16}$ is halo, methyl, or ethyl;

each $R^{22}$ is independently chloro, fluoro, —CN, —$C_{1-3}$ alkyl, —O—$C_{1-3}$ alkyl, —O-cyclopropyl, —O-cyclobutyl, —$CF_3$, —$OCF_3$, or —$SO_2$—($C_{1-3}$ alkyl); and p is an integer from zero to 3;

or a pharmaceutically acceptable salt thereof.

22. The compound according to claim 20, wherein $R^{10}$ is:

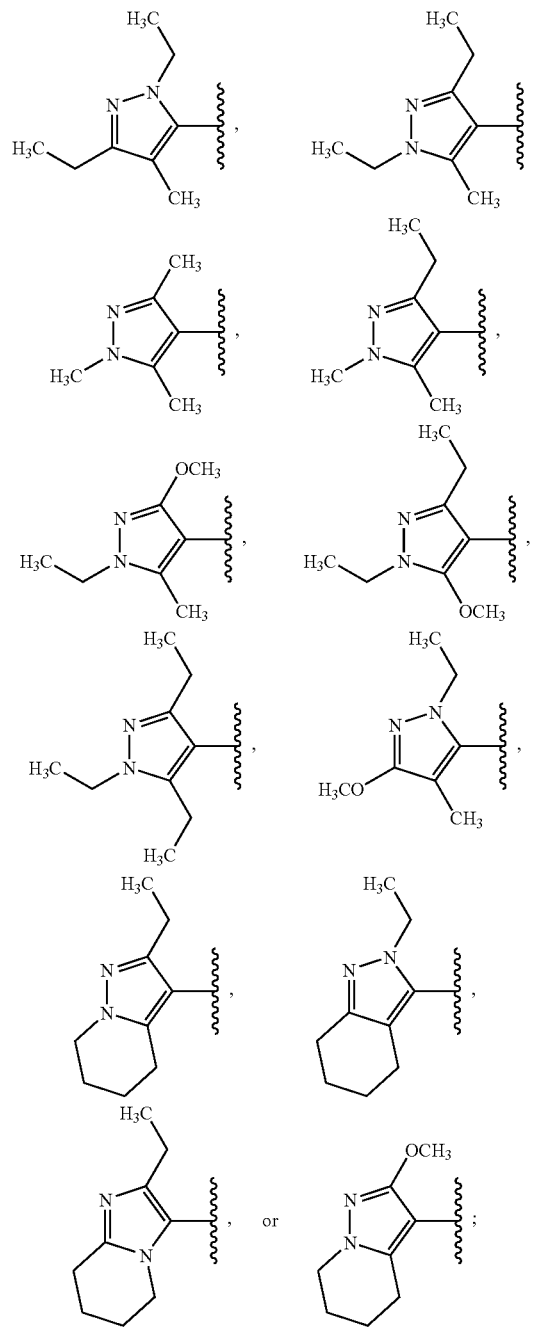

or a pharmaceutically acceptable salt thereof.

23. The compound according to claim 22, wherein $R^{10}$ is:

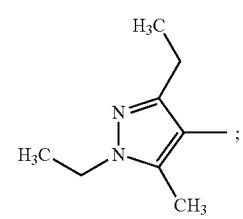

or a pharmaceutically acceptable salt thereof.

24. The compound according to claim 22, wherein R[10] is:

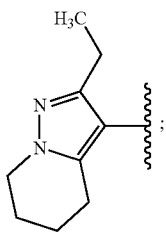

or a pharmaceutically acceptable salt thereof.

25. The compound according to claim 1, which is a compound selected from the group consisting of:

1-{[(3S,4S)-3-{[4-(2-ethyl-4,5,6,7-tetrahydropyrazolo[1,5-a]pyridin-3-yl)piperidin-1-yl]methyl}-4-(3-fluorophenyl)pyrrolidin-1-yl]methyl}cyclopentanecarboxylic acid;

1-{[(3S,4S)-3-{[4-(2-ethyl-4,5,6,7-tetrahydropyrazolo[1,5-a]pyridin-3-yl)piperidin-1-yl]methyl}-4-(3-fluorophenyl)pyrrolidin-1-yl]methyl}cyclohexanecarboxylic acid;

1-{[(3R,4S)-3-{(1R)-1-[4-(1,3-diethyl-5-methyl-1H-pyrazol-4-yl)piperidin 1-yl]ethyl}-4-(3-fluorophenyl)pyrrolidin-1-yl]methyl}cyclobutanecarboxylic acid;

(1R,5R)-3-[((3S,4S)-3-(3,5-difluorophenyl)-4-{[4-(2-ethyl-4,5,6,7-tetrahydropyrazolo[1,5-a]pyridin-3-yl)piperidin-1-yl]methyl}pyrrolidin-1-yl)methyl]bicyclo[3.1.0]hexane-3-carboxylic acid;

3-[(3R,4S)-3-{(1R)-1-[4-(2-ethyl-4,5,6,7-tetrahydropyrazolo[1,5-a]pyridin-3-yl)piperidin-1-yl]ethyl}-4-(3-fluorophenyl)pyrrolidin-1-yl]-2,2-dimethylpropanoic acid;

1-{[(3R,4S)-3{(1R)-1-[4-(1,3-diethyl-4-methyl-1H-pyrazol-5-yl)piperidin-1-yl]ethyl}-4-(3-fluorophenyl)pyrrolidin-1-yl]methyl}cyclopentanecarboxylic acid;

1-{[(3R,4S)-3-{(1R)-1-[4-(1,3-diethyl-4-methyl-1H-pyrazol-5-yl)piperidin-1-yl]ethyl}-4-(3-fluorophenyl)pyrrolidin-1-yl]methyl}cyclohexanecarboxylic acid;

1-{[(3S,4S)-3-{[4-(2-ethyl-4,5,6,7-tetrahydropyrazolo[1,5-a]pyridin-3-yl)piperidin-1-yl]methyl}-4-(3-fluorophenyl)pyrrolidin-1-yl]methyl}cyclobutanecarboxylic acid;

1-{[(3S,4S)-3-{[4-(1,3-diethyl-4-methyl-1H-pyrazol-5-yl)piperidin-1-yl]methyl}-4-(3-fluorophenyl)pyrrolidin-1-yl]methyl}cyclohexanecarboxylic acid;

1-{[(3S,4S)-3-{[4-(1,3-diethyl-4-methyl-1H-pyrazol-5-yl)piperidin-1-yl]methyl}-4-(3-fluorophenyl)pyrrolidin-1-yl]methyl}cyclopentanecarboxylic acid;

1-{[(3S,4S)-3-{[4-(2-ethyl-4,5,6,7-tetrahydro-2H-indazol-3-yl)piperidin-1-yl]methyl}-4-(3-fluorophenyl)pyrrolidin-1-yl]methyl}cyclopentanecarboxylic acid;

1-{[(3S,4S)-3-{[4-(2-ethyl-4,5,6,7-tetrahydro-2H-indazol-3-yl)piperidin-1-yl]methyl}-4-(3-fluorophenyl)pyrrolidin-1-yl]methyl}cyclohexanecarboxylic acid;

2-ethyl-2-{[(3S,4S)-3-{[4-(2-ethyl-4,5,6,7-tetrahydropyrazolo[1,5-a]pyridin-3-yl)piperidin-1-yl]methyl}-4-(3-fluorophenyl)pyrrolidin-1-yl]methyl}butanoic acid;

2-{[(3S,4S)-3-{[4-(1,3-diethyl-5-methyl-1H-pyrazol-4-yl)piperidin-1-yl]methyl}-4-(3-fluorophenyl)pyrrolidin-1-yl]methyl}-2-ethylbutanoic acid;

(1R,5S)-3-{[(3S,4S)-3-{[4-(1,3-diethyl-4-methyl-1H-pyrazol-5-yl)piperidin-1-yl]methyl}-4-(3-fluorophenyl)pyrrolidin-1-yl]methyl}bicyclo[3.1.0]hexane-3-carboxylic acid;

(1R,5S)-3-{[(3S,4S)-3-{[4-(1,3-diethyl-5-methyl-1H-pyrazol-4-yl)piperidin-1-yl]methyl}-4-(3-fluorophenyl)pyrrolidin-1-yl]methyl}bicyclo[3.1.0]hexane-3-carboxylic acid;

3-[(3S,4S)-3-{[4-(1,3-diethyl-5-methyl-1H-pyrazol-4-yl)piperidin-1-yl]methyl}-4-(3-fluorophenyl)pyrrolidin-1-yl]-2,2-dimethylpropanoic acid;

(1R,5S)-3-{[(3R,4S)-3-{(1R)-1-[4-(1,3-diethyl-5-methyl-1H-pyrazol-4-yl)piperidin-1-yl]ethyl}-4-(3-fluorophenyl)pyrrolidin-1-yl]methyl}bicyclo[3.1.0]hexane-3-carboxylic acid;

3-[(3R,4S)-3-{(1R)-1-[4-(1,3-diethyl-5-methyl-1H-pyrazol-4-yl)piperidin-1-yl]ethyl}-4-(3-fluorophenyl)pyrrolidin-1-yl]-2,2-dimethylpropanoic acid;

(1R,5R)-3-{[(3S,4S)-3-{[4-(2-ethyl-4,5,6,7-tetrahydropyrazolo[1,5-a]pyridin-3-yl)piperidin-1-yl]methyl}-4-(3-fluorophenyl)pyrrolidin-1-yl]methyl}bicyclo[3.1.0]hexane-3-carboxylic acid;

and pharmaceutically acceptable salts thereof.

26. The compound according to claim 1, which is a compound selecetd from the group consising of:

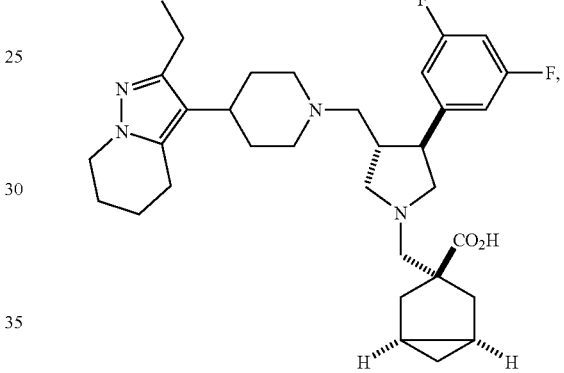

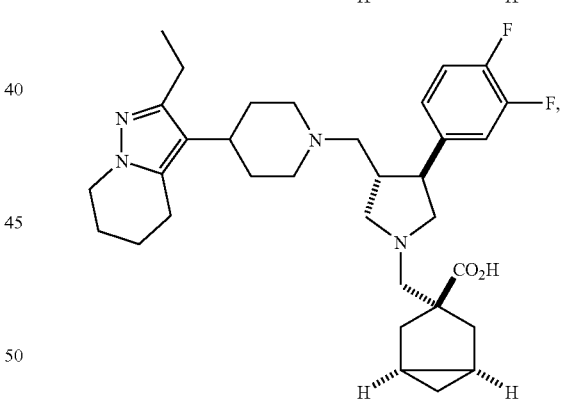

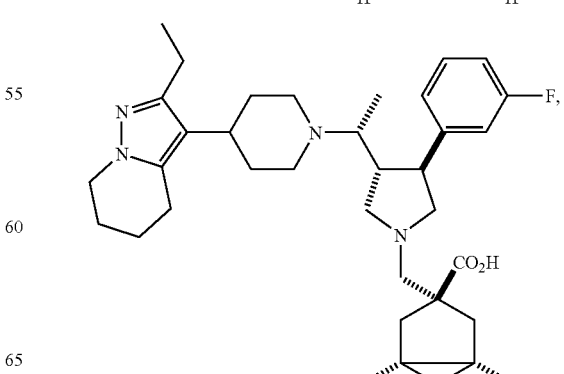

-continued
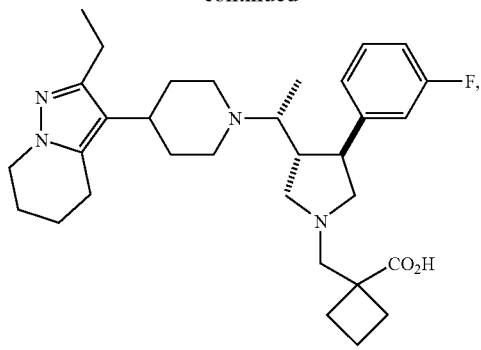
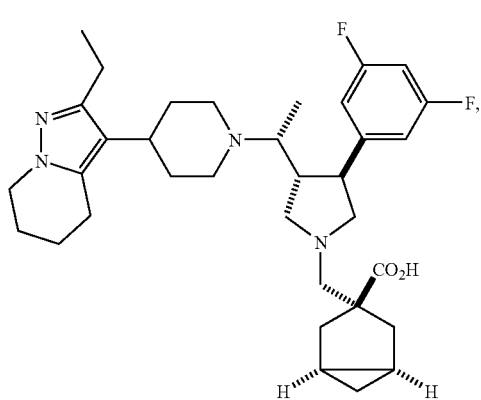
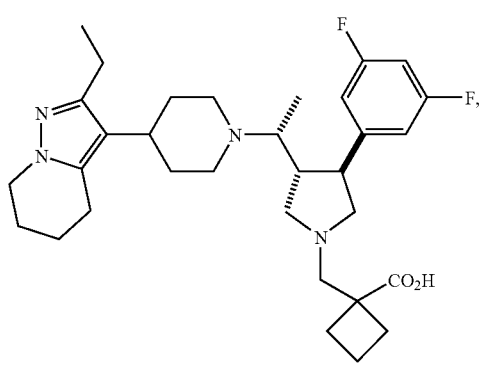
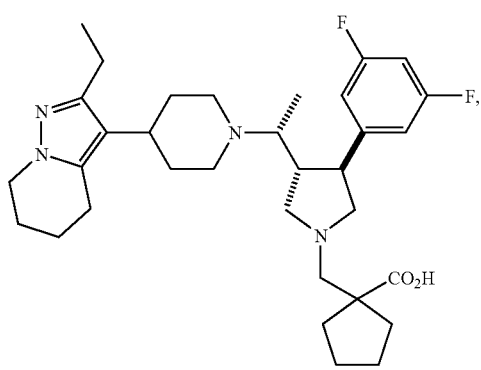
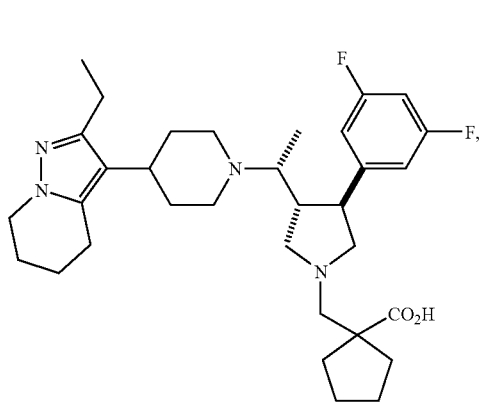
and pharmaceutically acceptable salts thereof.
27. A pharmaceutical composition which comprises an inert carrier and an effective amount of a compound according to claim 1 or a pharmaceutically acceptable salt thereof.
* * * * *